US010246503B2

(12) United States Patent
Qian et al.

(10) Patent No.: US 10,246,503 B2
(45) Date of Patent: Apr. 2, 2019

(54) METHOD OF IMPROVING THE PHARMACOKINETIC PROFILE OF A THERAPEUTIC POLYPEPTIDE AND THE USE THEREOF

(71) Applicant: BEIJING ANXINHUAIDE BIOTECH. CO., LTD, Beijing (CN)

(72) Inventors: Xinguo Qian, Beijing (CN); Wei Hong, Shijiazhuang (CN); Xiaoyu Ma, Beijing (CN)

(73) Assignee: BEIJING ANXINHUAIDE BIOTECH. CO., LTD., Beijing (CN)

( * ) Notice: Subject to any disclaimer, the term of this patent is extended or adjusted under 35 U.S.C. 154(b) by 174 days.

(21) Appl. No.: 14/655,282

(22) PCT Filed: Dec. 19, 2013

(86) PCT No.: PCT/CN2013/001602
§ 371 (c)(1),
(2) Date: Jun. 24, 2015

(87) PCT Pub. No.: WO2014/101287
PCT Pub. Date: Jul. 3, 2014

(65) Prior Publication Data
US 2016/0194370 A1    Jul. 7, 2016

(30) Foreign Application Priority Data
Dec. 24, 2012   (WO) ................ PCT/CN2012/001723

(51) Int. Cl.
C07K 14/605   (2006.01)
A61K 38/26    (2006.01)
C07K 14/635   (2006.01)
C07K 14/705   (2006.01)
C07K 14/715   (2006.01)
C07K 14/78    (2006.01)
C07K 14/71    (2006.01)
A61K 38/17    (2006.01)
A61K 38/18    (2006.01)
A61K 38/19    (2006.01)
A61K 38/21    (2006.01)
A61K 38/27    (2006.01)
A61K 38/29    (2006.01)

(52) U.S. Cl.
CPC ............ C07K 14/605 (2013.01); A61K 38/26 (2013.01); C07K 14/635 (2013.01); C07K 14/70578 (2013.01); C07K 14/71 (2013.01); C07K 14/7151 (2013.01); C07K 14/7156 (2013.01); C07K 14/78 (2013.01); A61K 38/179 (2013.01); A61K 38/1816 (2013.01); A61K 38/193 (2013.01); A61K 38/21 (2013.01); A61K 38/27 (2013.01); A61K 38/29 (2013.01); C07K 2319/31 (2013.01)

(58) Field of Classification Search
CPC ................ C07K 14/605; C07K 14/635; C07K 14/70578; C07K 14/71; C07K 14/7151; C07K 14/7156; C07K 14/78; A61K 38/26
See application file for complete search history.

(56) References Cited

U.S. PATENT DOCUMENTS

| 5,961,973 | A   |   | 10/1999 | Crea |                   |
|-----------|-----|---|---------|------|-------------------|
| 7,528,242 | B2  | * | 5/2009  | Anderson | ........ C07K 14/43595 |
|           |     |   |         |          | 435/183           |
| 7,846,445 | B2  | * | 12/2010 | Schellenberger | .... C07K 14/001 |
|           |     |   |         |          | 424/178.1         |
| 7,855,279 | B2  | * | 12/2010 | Schellenberger | ........ C07K 7/06 |
|           |     |   |         |          | 530/300           |
| 8,492,530 | B2  | * | 7/2013  | Schellenberger | ........ C07K 7/06 |
|           |     |   |         |          | 435/4             |
| 8,673,860 | B2  | * | 3/2014  | Schellenberger | .... C07K 14/001 |
|           |     |   |         |          | 514/1.1           |
| 8,933,197 | B2  | * | 1/2015  | Stemmer | ............... C07K 14/535 |
|           |     |   |         |          | 530/324           |
| 9,249,211 | B2  | * | 2/2016  | Schellenberger | .. C07K 14/8125 |
| 9,371,369 | B2  | * | 6/2016  | Schellenberger | .... C07K 14/001 |
| 9,376,672 | B2  | * | 6/2016  | Schellenberger | ............ |
|           |     |   |         |          | C12Y 304/2102     |
| 9,758,776 | B2  | * | 9/2017  | Schellenberger | ...... C12N 9/644 |
| 2009/0092582 | A1 | * | 4/2009 | Bogin | .................. C07K 14/535 |
|           |     |   |         |          | 424/85.5          |

(Continued)

FOREIGN PATENT DOCUMENTS

EP   2441776 A1 * 4/2012 ............. C07K 14/78
EP   24411776     4/2012

OTHER PUBLICATIONS

Kloczkowski et al., (Proteins. Nov. 1, 2002;49(2):154-66).*

(Continued)

Primary Examiner — Gyan Chandra
(74) Attorney, Agent, or Firm — Christensen O'Connor; Johnson Kindness PLLC

(57) ABSTRACT

The present invention provides a fusion protein comprising a therapeutic polypeptide fused to one or more flexible unstructured polypeptides and a trimeric scaffold protein. The flexible unstructured polypeptide sequence within the fusion protein is exhibited as one or more pCloud sequences derived from human fibrinogen alpha chain, and may be flanked by a proteinous connecting moiety of human origin. Also provided are pharmaceutical compositions comprising the fusion protein, nucleic acid molecules encoding the fusion protein, vectors containing the nucleic acids, host cells transformed with the vectors, and methods of making the fusion proteins of the invention, and use thereof.

7 Claims, 12 Drawing Sheets
Specification includes a Sequence Listing.

(56) References Cited

U.S. PATENT DOCUMENTS

2012/0230947 A1* 9/2012 Schellenberger ........ C07K 7/06
424/85.2
2015/0037359 A1* 2/2015 Schellenberger .... C07K 5/0205
424/178.1

OTHER PUBLICATIONS

Iwai et al., (Mol Med. Sep.-Dec. 2003; 9(9-12): 209-219).*
Ohashi et al., "An experimental study of GFP-based FRET, with the application to intrinsically unstructured proteins", Protein Science, Jul. 2007, vol. 16, No. 7, pp. 1429-1438.
Liu et al., "The mechanical properties of single fibrin fibers", Journals of Thrombosis and Haemostasis, May 2010, vol. 8, No. 5, pp. 1030-1036.

* cited by examiner

```
          10         20         30         40         50         60
MFSMRIVCLV LSVVGTAWTA DSGEGDFLAE GGGVRGPRVV ERHQSACKDS DWPFCSDEDW 70         80         90        100        110        120
NYKCPSGCRM KGLIDEVNQD FTNRINKLKN SLFEYQKNNK DSHSLTTNIM EILRGDFSSA 130        140        150        160        170        180
NNRDNTYNRV SEDLRSRIEV LKRKVIEKVQ HIQLLQKNVR AQLVDMKRLE VDIDIKIRSC 190        200        210        220        230        240
RGSCSRALAR EVDLKDYEDQ QKQLEQVIAK DLLPSRDRQH LPLIKMKPVP DLVPGNFKSQ 250        260        270        280        290        300
LQKVPPEWKA LTDMPQMRME LERPGGNEIT RGGSTSYGTG SETESPRNPS SAGSWNSGSS 310        320        330        340        350        360
GPGSTGNRNP GSSGTGGTAT WKPGSSGPGS TGSWNSGSSG TGSTGNQNPG SPRPGSTGTW 370        380        390        400        410        420
NPGSSERGSA GHWTSESSVS GSTGQWHSES GSFRPDSPGS GNARPNNPDW GTFEEVSGNV 430        440        450        460        470        480
SPGTRREYHT EKLVTSKGDK ELRTGKEKVT SGSTTTTRRS CSKTVTKTVI GPDGHKEVTK 490        500        510        520        530        540
EVVTSEDGSD CPEAMDLGTL SGIGTLDGFR HRHPDEAAFF DTASTGKTFP GFFSPMLGEF 550        560        570        580        590        600
VSETESRGSE SGIFTNTKES SSHHPGIAEF PSRGKSSSYS KQFTSSTSYN RGDSTFESKS 610        620        630        640        650        660
YKMADEAGSE ADHEGTHSTK RGHAKSRPVR DCDDVLQTHP SGTQSGIFNI KLPGSSKIFS 670        680        690        700        710        720
VYCDQETSLG GWLLIQQRMD GSLNFNRTWQ DYKRGFGSLN DEGEGEFWLG NDYLHLLTQR 730        740        750        760        770        780
GSVLRVELED WAGNEAYAEY HFRVGSEAEG YALQVSSYEG TAGDALIEGS VEEGAEYTSH 790        800        810        820        830        840
NNMQFSTFDR DADQWEENCA EVYGGGWWYN NCQAANLNGI YYPGGSYDPR NNSPYEIENG 850        860
VVWVSFRGAD YSLRAVRMKI RPLVTQ
```

Fig. 2

METHOD OF IMPROVING THE PHARMACOKINETIC PROFILE OF A THERAPEUTIC POLYPEPTIDE AND THE USE THEREOF

FIELD OF THE INVENTION

The present invention relates generally to a fusion protein with therapeutic efficacy. In particular, the present invention relates to a method of improving the half life of a therapeutic polypeptide by fusing with one or more flexible un-structured polypeptide sequences and a trimeric scaffold protein and the use thereof.

BACKGROUND OF THE INVENTION

Many therapeutic polypeptides suffer from short terminal in vivo half life and poor thermal stability when injected into a subject. Short plasma half life is commonly due to fast renal clearance as well as to enzymatic degradation occurring during systemic circulation. The long half life time is usually required for a therapeutic polypeptide to achieve its optimal efficacy. Increasing the in vivo residence times of the therapeutic polypeptides could decrease their dosing frequencies and make them more convenient for the patients to use.

PEGylation has been widely utilized to extend the half life of a therapeutic polypeptide (see review paper [1-4], patents 1-9). PEGylation changes the physical and chemical properties of the biomedical molecule, such as its conformation, electrostatic binding, and hydrophobicity, and results in an improvement in the pharmacokinetic behavior of the drug. In general, PEGylation improves drug solubility and decreases immunogenicity. PEGylation also increases drug stability and the retention time of the conjugates in blood. However, PEGylation has severe consequences for the biological activities of the protein. The activity of the PEGylated protein usually reduces by 20-50 fold [2, 5](patents 1-9). In addition, the site for PEGylation needs to be carefully decided to avoid interfering with the active site of the therapeutic polypeptide. For some short peptides such as GLP-1, PTH and Calcitonin, it would be difficult to choose the proper site for PEGylation without disturbing the biological activity of the peptides. Moreover, PEG is a heterogeneous mixture of related polymers, its conjugation to a therapeutic polypeptide results in numerous distinct species with similar molecular sizes and chemical properties. This complicates the purification and increases the production costs of the PEGylated products.

It has been reported that fusion of a therapeutic polypeptide with human IgG Fc fragment or human serum albumin (HSA) may significantly increase the half life of the therapeutic polypeptide [6-9] (patents 10, 11, 12). However, recombinant fusion protein with IgG Fc fragment or HSA needs to be produced from eukaryotic systems such as mammalian cell lines or yeast cells, which significantly increases the cost of the recombinant protein.

SUMMARY OF THE INVENTION

The present invention is directed to enhance the pharmaceutical properties, stability, solubility and safety of the therapeutic polypeptides. The present invention is particularly useful for improving the pharmacokinetic properties, such as in vivo terminal half-life, of a therapeutic polypeptide.

In one aspect, the present invention provides a fusion protein comprising a therapeutic polypeptide fused to a scaffold protein which forms a homo-trimer in solution. The fusion protein further comprises one or more flexible un-structured polypeptide sequences. In some embodiments, the fusion protein further comprises a proteinous connecting moiety (PCM) of human origin. In a particular embodiment, the proteinous connecting moiety is a proteinous sequence having an elongated shape, such as a human Fibronectin type III domain.

The flexible un-structured polypeptide sequence contains 1 to 3000 amino acid residues, wherein the sum of G, S, E, A, P and T constitutes more than 90% of the flexible un-structured polypeptide sequence; and the flexible un-structured polypeptide sequence has greater than 90% unstructured random coil formation as determined by GOR algorithm [10]. Fusing the therapeutic polypeptide with one or more flexible unstructured polypeptide sequences and the trimeric scaffold protein can significantly increase the apparent molecular weight of the fusion protein and improve the in vivo half life of the therapeutic polypeptide. Moreover, this method renders the therapeutic polypeptide with tri-valency, which may greatly enhance the potency and efficacy of the therapeutic polypeptide (reviewed in [11]). This novel method provided by the invention, termed as "Trident technology", can efficiently increase the hydrodynamic radius and/or the radius of gyration (Rg) of the polypeptide molecule to extend its half life in vivo. The flexible unstructured polypeptide sequences and the proteinous connecting moiety (PCM) within the fusion protein contribute significantly to increasing the apparent molecular weight of the fusion proteins.

In the present invention, the therapeutic polypeptide may be fused with one or more flexible unstructured polypeptides and the trimeric scaffold protein in a number of ways. In some embodiments, the fusion protein of the present invention may be configured, from N-terminus to C-terminus, using the following formula:

$$(\text{Linker})_m\text{-TP-}(\text{Linker})_n\text{-Scaffold-}(\text{Linker})_k \text{ or}$$

$$(\text{Linker})_m\text{-Scaffold-}(\text{Linker})_n\text{-TP-}(\text{Linker})_k$$

wherein:
(a) Linker is the flexible un-structured polypeptide linker above;
(b) TP is a therapeutic polypeptide;
(c) Scaffold indicates the scaffold protein which forms a homo-trimer in solution;
(d) m is either 0 or 1; and n is either 0 or 1, k is either 0 or 1, and m+n+k>=1. These digits indicate the number of presence of the designated polypeptides.

In some embodiments of the invention, the fusion protein may further contain a proteinous connecting moiety of human origin. The therapeutic polypeptide is connected with the flexible un-structured polypeptide sequence via the proteinous connecting moiety of human origin. The fusion protein exhibits an improved pharmacokinetic profile when administered to a subject compared with the therapeutic polypeptide by itself. The fusion protein may be configured, from N-terminus to C-terminus, according to the following formula:

$$(\text{Linker})_m\text{-TP-Loop-PCM-}(\text{Linker})_j\text{-Scaffold-}(\text{Linker})_k$$
or $$(\text{Linker})_m\text{-Scaffold-}(\text{Linker})_n\text{-PCM-Loop-TP-}(\text{Linker})_k$$

wherein:

(a) Linker is the flexible un-structured polypeptide linker characterized above;

(b) TP is the therapeutic polypeptide;

(c) Scaffold indicates the scaffold protein which forms a homo-trimer in solution;

(d) m is either 0 or 1; and n is either 0 or 1, j is either 0 or 1, k is either 0 or 1, and m+n+j+k>=1. These digits indicate the number of presence of the designated polypeptides.

(e) PCM is the proteinous connecting moiety of human origin; and (f) Loop is a flexible loop which refers to the protein sequence which has the variable lengths from 0 to 100 residues. These flexible loops are rich in glycine (G) and serine (S). These flexible loops may also contain glutamate (E), alanine (A), proline (P) and threonine (T). These flexible loops have greater than 95% unstructured random coil formation as determined by GOR algorithm.

In a preferred embodiment of the invention, the flexible un-structured linker is exhibited as one or more flexible un-structured pCloud polypeptides. The pCloud sequence is characterized in: (a) the total pCloud amino acid residues is at least 100 to about 3000 amino acid residues; (b) the pCloud polypeptide is generated by use of some or all of the fragments derived from human fibrinogen alpha chain (Table 1). In pCloud sequence, the fibrinogen fragments are flanked by flexible loops with various lengths. Therefore the pCloud polypeptide is primarily human originated and has low immunogenicity. (c) the pCloud polypeptide is rich in glycine (G), serine (S) and Glutamate (E). The pCloud polypeptide also contains alanine (A), proline (P), arginine (R) and threonine (T). The sum of G, S, E, A, P and T constitutes more than 90% of the pCloud sequence. (d) The pCloud sequence has greater than 90% unstructured random coil formation as determined by GOR algorithm [10]; and (e) the pCloud sequence does not contain any T-cell epitopes as predicted by TEPITOPE algorithm [12].

In some embodiments, the pCloud polypeptide represents a flexible unstructured polypeptide originated from human fibrinogen alpha chain. The fragments derived from human fibrinogen alpha chain (listed in Table 1) can be utilized as the building blocks to constitute the pCloud polypeptide. In the pCloud sequence, the human fibrinogen alpha chain fragments are flanked by flexible loops with variable lengths from 0 to 100 residues. Attaching one or more pCloud polypeptide to a therapeutic polypeptide may significantly increase the apparent molecular weight of the therapeutic polypeptide and improve the in vivo half life of the therapeutic polypeptide. The in vivo half life of the therapeutic polypeptide connected with the pCloud sequence can be adjusted by varying the length of the pCloud sequence. More importantly, the pCloud sequence is generated based on the human fibrinogen alpha chain, therefore, the pCloud polypeptide may not stimulate the immune responses from human patients when administrated.

In some embodiments, the scaffold protein of the invention is selected from the group consisting of human collagen noncollagenous (NC) domains which form stable homo-trimers in solution, proteins which form homo-trimers in solution with C1q-like molecular structures, proteins which form homo-trimers in solution with TNF-like molecular structures, and proteins with C-type lectin-like domains (CTLD) which form homo-trimers in solution. In some embodiments, the scaffold protein is selected from the group consisting of the NC1 domain within Multiplexin type of human Collagen, NC2 domain within FACIT type of collagen, human C1q A chain, C1q B chain, C1q C chain, cbln family members, human EMILIN-1, multimerin, ACRP30/adiponectin, adipolin, resistin, resistin-like molecule (RELM) hormone family members, human TNFalpha, TNF-beta, TRAIL, RANK ligand, Fas ligand, CD 30 ligand, CD40 ligand, CD27 ligand, OX40L, CD137, mannan-binding lectin (MBL), surfactant protein A (SP-A), surfactant protein D (SP-D), collectin liver 1 (CL-L1), collectin placenta 1 (CL-P1), conglutinin, collectin of 43 kDa (CL-43) and collectin of 46 kDa (CL-46), Langerin, Tetranectin and functional variants thereof. In the preferred embodiments, the NC1 domain within Multilexin type of human Collagen (such as collagen XV and XVIII) is selected as the scaffold protein in the present invention.

In some embodiments, the therapeutic polypeptide is selected from the group consisting of human glucagon-like peptide-1 (GLP-1), Exenatide, GLP-2, C-peptide, Calcitonin, human Parathyroid hormone (PTH), glucagon, G-CSF, GM-CSF, Interferon, interleukin factors, VEGF receptors, TNF alpha receptors, RANK, Growth hormone, Erythropoietin, blood-coagulation factors, single-chain Fv, single domain antibodies and functional variants thereof.

In some embodiments, the therapeutic polypeptide is connected with the pCloud sequence via a proteinous connecting moiety of human origin. In a particular embodiment, the proteinous connecting moiety is a proteinous sequence having an elongated shape, such as human Fibronectin type III domain.

In the particular embodiments of the invention, the fusion protein of the invention comprises, from N-terminus to C-terminus, a therapeutic polypeptide selected from the group consisting of GLP-1, GLP-1(A8G/G22E), GLP-1(A8G/G22E/R36S) and GLP-1(A8G/G22E/R36G); a flexible loop; a proteinous connecting moiety selected from the group consisting of Fn7, Fn8 and TNCfn3; a pCloud sequence; and a scaffold protein selected from the group consisting of COL18NC1, COL15NC1, COL19NC2, and ACRP30 C1q-like domain.

In a preferred embodiment of the invention, the fusion protein of the invention comprises, from N-terminus to C-terminus, GLP-1(A8G/G22E/R36G), a flexible loop, Fn8, a pCloud sequence, and COL18NC1.

In another preferred embodiment of the invention, the fusion protein of the invention comprises, from N-terminus to C-terminus, a first pCloud sequence, human growth hormone, a second pCloud sequence and COL18NC1.

The present invention also provides a polynucleotide sequence encoding the fusion protein, a pharmaceutical composition comprising the fusion protein and a pharmaceutically acceptable carrier, and an expression vector comprising the polynucleotide sequence and expression control elements.

In another aspect, the present invention provides a method of improving the pharmacokinetic property of a therapeutic polypeptide, comprising the steps of fusing the therapeutic polypeptide to one or more pCloud polypeptide and a trimeric scaffold protein. In some embodiments, the therapeutic polypeptide is connected with the pCloud sequence via a proteinous connecting moiety of human origin. The fusion protein of the present invention achieves a property characterized in that (a) the terminal half-life of the therapeutic polypeptide linked to the scaffold protein and one or more pCloud sequence is significantly longer as compared to the terminal half-life of the therapeutic polypeptide by itself; (b) stability and solubility under physiologic conditions of the therapeutic polypeptide linked to the scaffold protein and one or more pCloud sequence are improved as compared to the stability and solubility of the therapeutic polypeptide by itself.

BRIEF DESCRIPTION OF THE DRAWINGS

FIG. 2. The amino acid sequence of the mature human fibrinogen alpha chain (SEQ ID NO:88). The amino acid residue numbers of the fibrinogen alpha chain are listed. The 12 unstructured fragments containing primarily the residues glycine (G), serine (S) and Glutamate (E), proline (P), arginine (R) and threonine (T) are underlined. To further reduce the immunogenicity of these fragments, mutations Y277S, V379A and D396E were introduced. The residues Y277, V379 and D396 are in bold.

FIG. 9 shows the Intraperitoneal glucose tolerance test (IPGTT) results of GLP1(A8G/G22E/R36G)-Fn8-p246-COL18NC1 in SD rats. In this figure, GLP1(A8G/G22E/R36G)-Fn8-p246-COL18NC1 is labeled as p246.

DEFINITIONS

Figure 1A:
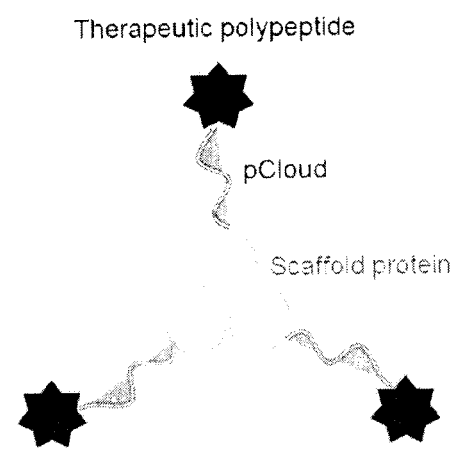
FIG. 1 shows the schematic drawings illustrating some mechanisms of the present invention. The therapeutic polypeptide is shown as a star in FIG. 1a and FIG. 1c and as a helix in FIG. 1b. a) The therapeutic polypeptide is connected directly to the pCloud polypeptide and the scaffold protein. b) The therapeutic polypeptide is fused with the pCloud polypeptide and the scaffold protein via a proteinous connecting moiety of human origin, preferably a proteinous sequence with an elongated shape. c) The therapeutic polypeptide and the pCloud polypeptide can be fused at the opposite terminus of the scaffold protein.

The terms "polypeptide", "peptide", and "protein" are used interchangeably herein to refer to polymers of amino acids of any length. The polymer may be linear or branched, it may comprise modified amino acids, and it may be interrupted by non-amino acids. The terms also encompass an amino acid polymer that has been modified, for example, by disulfide bond formation, glycosylation, lipidation, acetylation, phosphorylation, or any other manipulation, such as conjugation with a labeling component. The terms "flexible unstructured polypeptide", "flexible unstructured polypeptide sequence", and "flexible unstructured linker" "flexible unstructured polypeptide linker" are used interchangeably in this invention. The flexible un-structured polypeptide sequence contains 1 to 3000 amino acid residues, wherein the sum of G, S, E, A, P and T constitutes more than 90% of the flexible un-structured polypeptide sequence; and the flexible un-structured polypeptide sequence has greater than 90% unstructured random coil formation as determined by GOR algorithm [10].

The term "pCloud" polypeptide is characterized in: (a) the total pCloud amino acid residues is at least 100 to about 3000 amino acid residues; (b) the pCloud polypeptide sequence is generated by use of some or all of the fragments derived from human fibrinogen alpha chain. In pCloud sequence, the fibrinogen fragments are flanked by flexible loops with various lengths. Therefore pCloud is primarily human originated and has low immunogenicity when administered to human. (c) the pCloud sequence is rich in glycine (G), serine (S) and Glutamate (E). The pCloud also contains alanine (A), proline (P), arginine (R) and threonine (T). The sum of G, S, E, A, P and T constitutes more than 90% of the pCloud sequence. (d) The pCloud sequence has greater than 90% unstructured random coil formation as determined by GOR algorithm; and (e) the pCloud sequence does not contain any T-cell epitopes as predicted by TEPITOPE algorithm. Within the pCloud polypeptide, the human fibrinogen fragments are flanked by flexible loops with variable lengths from 0 to 100 residues.

The term "flexible loop" in this invention refers to the protein sequence which has the variable lengths from 0 to 100 residues. These flexible loops are rich in glycine (G) and serine (S). These flexible loops may also contain glutamate (E), alanine (A), proline (P) and threonine (T). These flexible loops have greater than 95% unstructured random coil formation as determined by GOR algorithm. The flexible loops are generally the flexible unstructured polypeptide linkers with shorter lengths and more flexibility. A skilled artisan will appreciate that the flexible loop may be utilized in the fusion protein as a spacer to provide flexibility.

A "fragment" is a truncated form of a native protein. The term "variant" or "functional variant" of a protein refers to a modified version of the native protein which comprises substitutions, deletions and/or additions of one or several amino acids, and which substantially retains the biological activity of the native protein. For example, a variant protein may share at least 70%, 75%, 80%, 85%, 90%, 95%, 96%, 97%, 98% or 99% amino acid sequence identity with the reference protein. Typically, conservative substitutions of amino acids are preferred which are well known to a skilled artisan. Deletions are preferably deletions of amino acids from regions not involved in the biological function of the protein. For example, GLP-1(A8G/G22E/R36G) is a functional variant of wild type GLP-1, which contains three substitutions of amino acids and which substantially retains or increases its biological activity as shown by the cAMP assay.

"Conjugated", "linked," "connected", "fused," and "fusion" are used interchangeably herein. These terms refer to the joining together of two more chemical elements or components, by whatever means including chemical conjugation or recombinant means. For example, two distinct proteins can be connected together by "in-frame fusion", which refers to the joining of two or more open reading frames (ORFs) to form a continuous longer ORF, in a manner that maintains the correct reading frame of the original ORFs. Thus, the resulting recombinant fusion protein is a single protein containing two or more segments that correspond to polypeptides encoded by the original ORFs (which segments are not normally so joined in nature). For another example, the two proteins can also be linked together by use of a chemical crosslinker, which results in a protein conjugate that contains two individual polypeptides connected by a crosslinker.

In the context of polypeptides, a "sequence" is an order of amino acids in a polypeptide in an amino to carboxyl terminus direction in which residues that neighbor each other in the sequence are contiguous in the primary structure of the polypeptide.

The terms "DNA", "polynucleotides", "nucleic acids", "nucleotides" and "oligonucleotides" are used interchangeably. They refer to a polymeric form of nucleotides of any length, either deoxyribonucleotides or ribonucleotides, or analogs thereof. Polynucleotides may have any three-dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component.

The term "functional variant" of a protein refers to a modified version of the native protein which comprises substitutions, deletions and/or additions of one or several amino acids, e.g., less than 15 amino acids, or preferably less than 10 or 5 amino acids, and which substantially retains the biological activity of the native protein. Typically, conservative substitutions of amino acids are preferred which are well known to a skilled artisan. Deletions are preferably deletions of amino acids from regions not involved in the biological function of the protein. For example, GLP-1 (A8G/G22E) and GLP-1(A8G/G22E/R36G) are the functional variants of wild type GLP-1, which contains two or three substitutions of amino acids and which substantially retains its biological activity such as increasing cAMP level.

DETAILED DESCRIPTION OF THE INVENTION

In one aspect of the present invention, there is provided a method to increase the half life of a therapeutic polypeptide by fusing the therapeutic polypeptide to one or more flexible un-structured polypeptide sequences and a scaffold protein. The scaffold protein can form a stable homo-trimer in solution. This method can efficiently increase the hydrodynamic radius and/or the radius of gyration (Rg) of the polypeptide molecule to extend its half life in vivo. Moreover, changing the length of the flexible unstructured polypeptide linker within the fusion protein can adjust the in vivo half life of the fusion protein in a tunable manner. In some embodiments, the fusion protein of the invention may further comprise a proteinous connecting moiety of human origin, preferably a proteinous sequence with an elongated shape. The proteinous connecting moiety can be connected to the therapeutic polypeptide via a flexible loop. The proteinous connecting moiety can be linked to the scaffold protein via a flexible, un-structured linker whose length is adjustable. This novel method provided by the invention, termed as "Trident technology", can efficiently improve the pharmacokinetics profile of the therapeutic polypeptide.

Figure 1B:
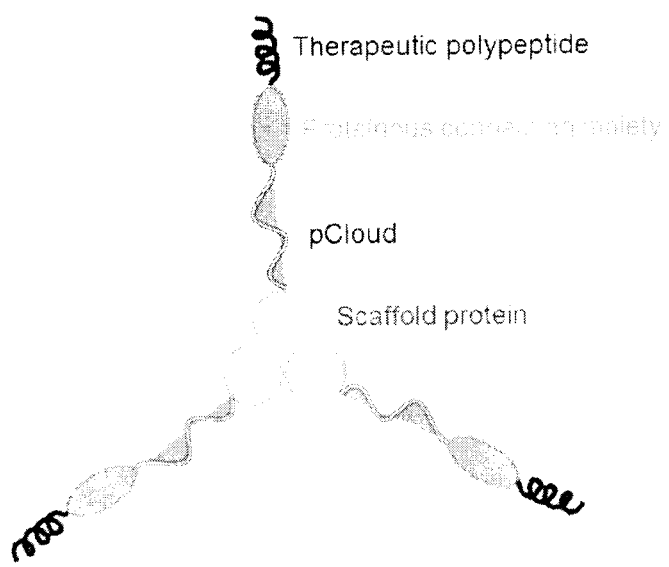
Figure 1C:
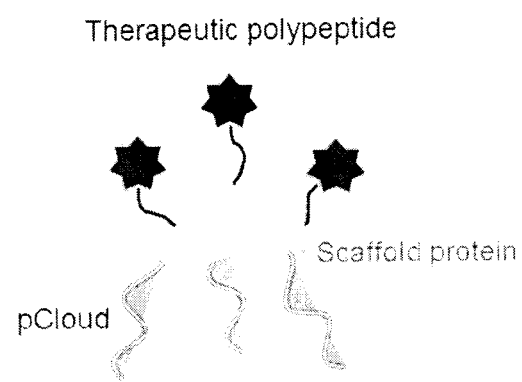

In a preferred embodiment of the invention, the flexible un-structured linker is exhibited as one or more un-structured pCloud polypeptides. Within the fusion protein, the therapeutic polypeptide, the pCloud polypeptides and the scaffold protein can be arranged in a number of manners. For example, in some embodiments, the therapeutic polypeptide is connected directly to the pCloud polypeptide and the scaffold protein (FIG. 1a). In some embodiments, the therapeutic polypeptide is fused with the pCloud polypeptide and the scaffold protein via a proteinous connecting moiety of human origin, preferably a proteinous sequence with an elongated shape (FIG. 1b). In some embodiments, the therapeutic polypeptide and the pCloud polypeptide can be fused at the opposite terminus of the scaffold protein (FIG. 1c).

In preferred embodiments of the present invention, the method of the invention may have several major advantages over the traditional PEGylation method or Fc/HSA fusion method. 1. In the method of the invention, PEGylation on the polypeptide molecule is not essential, therefore the biological activity of the therapeutic polypeptide is fully retained. 2. Because the scaffold protein forms a homotrimer, the fusion protein of the therapeutic polypeptide with the scaffold protein may greatly increase the apparent size of the fusion protein to slow down renal filtration. Moreover, the trimer formation also renders the fusion protein tri-valency. This may greatly increase the activity of the therapeutic protein. 3. The length of the flexible unstructured polypeptide linker within the fusion protein plays an important role in determining the in vivo half life of the fusion protein. The method of the invention provides a platform to fine tune the in vivo half life of a therapeutic polypeptide by varying the length of the flexible unstructured polypeptide linker within the fusion protein. 4. The scaffold protein and pCloud polypeptide is preferably generated from human proteins, usually from human extracellular proteins, therefore, no foreign protein sequences are introduced into the fusion protein. The immunogenicity of the fusion proteins generated using the method is low. 5. In many cases, the recombinant fusion protein of the present invention can be generated using *E. coli* expression system, which eliminates the need of the expensive chemical synthesis process for some therapeutic polypeptides or the need of using the eukaryotic expression systems.

The Flexible Unstructured Polypeptide Sequences

In this invention, the flexible unstructured polypeptide sequences within the fusion protein play critical roles in extending the half-life of the therapeutic polypeptide. The lengths of the flexible unstructured polypeptide sequences play important role in determining the hydrodynamic radius and/or the radius of gyration of the fusion protein. The primary sequences of the flexible unstructured polypeptide heavily affect the stability and solubility of the fusion protein.

The term "flexible un-structured polypeptide" refers to an amino acid sequence which is flexible in movement and which does not form any regular stable secondary and tertiary protein structures. The flexible un-structured polypeptide sequence contains 1 to 3000 amino acid residues, wherein the sum of G, S, E, A, P and T constitutes more than 90% of the flexible un-structured polypeptide sequence; and the flexible un-structured polypeptide sequence has greater than 90% unstructured random coil formation as determined by GOR algorithm [10].

If the therapeutic polypeptide is a relatively large protein (such as Interferon, Growth hormone, Erythropoietin, G-CSF, or TNFR2, usually a protein with more than 100 amino acid residues), it may be directly fused to the scaffold protein through a flexible, un-structured polypeptide linker. In some other cases, the therapeutic polypeptide might be a short peptide (such as GLP-1, Exenatide, GLP-2, C-peptide, Calcitonin or PTH, usually a peptide not more than 100 residues). To efficiently utilize our method, the fusion protein may further contain a proteinous connecting moiety of human origin, preferably a proteinous sequence with an elongated shape, such as the human Fibronectin type III domain. The therapeutic polypeptide and flexible unstructured polypeptide linker is connected by use of the proteinous connecting moiety. The proteinous connecting moiety can further increase the hydrodynamic radius and/or the radius of gyration (Rg) of the fusion protein. Moreover, the proteinous connecting moiety can stabilize the therapeutic polypeptide. In some embodiments, the proteinous connecting moiety may comprise a whole protein, a truncated version of a protein, a protein domain or domains in tandem, or protein fragments. A skilled artisan will appreciate that the proteinous connecting moiety may comprise some non-proteinous modifications which are not formed by amino acids, such as PEG.

The length of the flexible, unstructured linker may play an important role in determining the hydrodynamic radius and/or the radius of gyration (Rg) and the in vivo half life of the fusion protein. The flexible, unstructured polypeptide linker may contain sequences such as (G5S)n, (G4S)n, (G3S)n, (GS)n, (G2S2)n, (G3S3)n, (GS3)n where n is an integer, or other sequences that are rich in G, S, A, T or P. The length of the flexible linker may vary from 1 to 3000 amino acid residues, and particularly within the range of 5 to 500 amino acid residues. It has been reported that the un-structured stretches of polypeptides may act like PEG molecule and increase the hydrodynamic radius and/or the Rg of the protein molecule [13]. By use of our method, a relatively shorter flexible linker is needed to reach the desired Rg due to the trimer formation compared with the monomer. This may have great advantages for therapeutic proteins by reducing the immunogenicity.

In some embodiments of the invention, the fusion protein may consist of one or more flexible, un-structured polypeptide linkers. It will be appreciated by a skilled artisan that these flexible, un-structured linkers within the fusion protein may be the same or different.

Our data clearly showed that varying the length of the flexible, unstructured linker or linkers can efficiently change the hydrodynamic radius and/or Rg of the molecule and control the in vivo half life of the engineered protein molecule. Therefore, our method can generate a recombinant protein with tunable in vivo half life by varying the flexible, unstructured linker length within the fusion protein. This is advantageous compared with the traditional therapeutic IgG with fixed in vivo half life. In addition, our "Trident technology" may offer the fusion protein tri-valency for the ligand, in contrast, IgG only has bi-valency.

The pCloud Polypeptide

The present invention provides compositions comprising the "pCloud" polypeptide. In a preferred embodiment of the invention, the flexible un-structured linker is exhibited as one or more un-structured pCloud polypeptides. In some embodiments, pCloud polypeptides are generally extended polypeptides that have low degree or no secondary or tertiary structures under physiologic conditions.

The pCloud polypeptide is characterized in: (a) the total pCloud amino acid residues is at least 100 to about 3000 amino acid residues; (b) the pCloud polypeptide sequence is generated by use of some or all of the fragments derived from human fibrinogen alpha chain. In pCloud sequence, the fibrinogen fragments are flanked by flexible loops with various lengths. Therefore pCloud is primarily human originated and has low immunogenicity when administered to human. (c) the pCloud sequence is rich in glycine (G), serine (S) and Glutamate (E). The pCloud also contains alanine (A), proline (P), arginine (R) and threonine (T). The sum of G, S, E, A, P and T constitutes more than 90% of the pCloud sequence. (d) The pCloud sequence has greater than 90% unstructured random coil formation as determined by GOR algorithm; and (e) the pCloud sequence does not contain any T-cell epitopes as predicted by TEPITOPE algorithm.

It has been reported that fusing an unstructured polypeptide to the therapeutic polypeptide can significantly extend the in vivo half life of the therapeutic polypeptide (XTEN technology)[13]. However, in XTEN technology, the unstructured polypeptide is generated using artificial peptide fragments and it is not fused with a trimeric scaffold protein. These artificial peptides in XTEN technology represent foreign peptides to human body and it is likely that these foreign peptides may elicit immune responses within the patients when administrated. Because many therapeutic polypeptide, such as human Growth hormone and GLP-1 analogues, needs to be applied to the patients for an extended period, the foreign peptides introduced by the XTEN technology may represent a potential threat for the patients. In the present invention, a flexible unstructured "pCloud" polypeptide generated by use of human fibrinogen alpha chain sequences was demonstrated to efficiently extend the in vivo half life of therapeutic polypeptides. In addition, in the present invention, the pCloud polypeptide is further fused with a trimeric scaffold protein, which further enhances the pharmacokinetic profile of the therapeutic polypeptide.

In some embodiments of this invention, to constitute an unstructured pCloud polypeptide with low immunogenicity, we took advantage of the human fibrinogen alpha chain sequence. Human Fibrinogen (factor I) is a soluble, 340 kDa plasma glycoprotein, that is converted by thrombin into fibrin during blood clot formation [14-16]. Fibrinogen is synthesized in the liver by the hepatocytes. The normal concentration of fibrinogen in the human blood plasma is quite high (1.5-3 mg/ml), which strongly suggests that the human fibrinogen sequence may exhibit very low immunogenicity. Human fibrinogen is a hetero-hexamer that contains two sets of three different chains (α, β, and γ), linked to each other by disulfide bonds. Within the fibrinogen alpha (α) chain, an intrinsic unstructured region (residues 262-455) is present (FIG. 2). This unstructured region of fibrinogen contains minimum secondary structures as determined by GOR algorithm [10, 17]. 12 fragments within this fibrinogen unstructured region (residues 262-455) have been identified to contain primarily the residues glycine (G), serine (S) and Glutamate (E), proline (P), arginine (R) and threonine (T). In some embodiments of this invention, to further reduce the immunogenicity of these fragments, mutations Y277S, V379A and D396E were introduced in fragment 1, 9 and 11, respectively (FIG. 2). In some embodiments, the resultant 12 fragments derived from human fibrinogen alpha chain sequence are utilized as the building blocks to generate the pCloud polypeptides (Table 1). In some embodiments, the variants of these fragments that share at least 70%, 75%, 80%, 85% or 90% amino acid sequence identity with the fragments listed in Table 1 may be utilized as the building blocks for pCloud polypeptides.

TABLE 1 the protein sequences of the 12 fragments derived from human fibrinogen alpha chain

| 1 | GSTSSGTGSETESP SEQ ID NO:32 |
|---|---|
| 2 | PSSAGS (SEQ ID NO:33) |

TABLE 1-continued the protein sequences of the 12 fragments derived from human fibrinogen alpha chain

| 3 | SGSSGPGSTG (SEQ ID NO:34) |
|---|---|
| 4 | PGSSGTGGTAT (SEQ ID NO:35) |
| 5 | PGSSGPGSTGS (SEQ ID NO:36) |
| 6 | SGSSGTGSTG (SEQ ID NO:37) |
| 7 | PGSPRPGSTGT (SEQ ID NO:38) |
| 8 | PGSSERGSAG (SEQ ID NO:39) |
| 9 | TSESSASGSTG (SEQ ID NO:40) |
| 10 | SESGS (SEQ ID NO:41) |
| 11 | PESPGSG (SEQ ID NO:42) |
| 12 | TSGST (SEQ ID NO:43) |

In some embodiments of this invention, in order to generate the pCloud polypeptides, the fragments listed in Table 1 derived from human fibrinogen alpha chain are flanked by flexible loops with variable lengths from 0 to 100 residues. These flexible loops are rich in glycine (G) and serine (S). These loops also contain glutamate (E), alanine (A), proline (P) and threonine (T). The flexible loops have greater than 95% unstructured random coil formation as determined by GOR algorithm. The flexible loop sequences can be selected, but not limited, from the Table 2.

The flexible loops are generally the flexible unstructured polypeptide linkers with shorter lengths and more flexibility. In the present invention, the flexible loops are utilized to connect the human fibrinogen alpha chain fragments to constitute the pCloud polypeptide. In addition, the flexible loops are also utilized to connect therapeutic polypeptide and the proteinous connecting moiety of human origin in the fusion protein. The flexible loops may also be utilized to link the therapeutic polypeptide with the scaffold protein, the scaffold protein with the flexible unstructured polypeptide (or the pCloud polypeptide), and the proteinous connecting moiety with the flexible unstructured polypeptide (or the pCloud polypeptide). A skilled artisan will appreciate that the flexible loop may be utilized in the fusion protein as a spacer to provide flexibility.

TABLE 2 the protein sequences of the flexible loops utilized in the pCloud sequence to connect the fibrinogen alpha chain fragments. In the first line of the table, several G/S rich linkers are listed, n is an integer that can be adjusted based on needs.

(G2S)n, (G3S)n SEQ ID NO:91, (G4S)n SEQ ID NO:92, (G5S)n SEQ ID NO:93, (GS)n,(G2S2)n SEQ ID NO:94, (GS2)n, (GS3)n SEQ ID NO:95, (S2G)n, (S3G)n SEQ ID NO:96, (S4G)n SEQ ID NO:97, (S5G)n SEQ ID NO:98,(SG)n, (S2G2)n SEQ ID NO:99, (SG2)n, (SG3)n SEQ ID NO:100
GSESG (SEQ ID NO:44)

GSGSG (SEQ ID NO:45)

GSPSG (SEQ ID NO:46)

TABLE 2-continued the protein sequences of the flexible loops utilized in the pCloud sequence to connect the fibrinogen alpha chain fragments. In the first line of further activating other lymphocytes such as B cells to produce antibodies or activating T killer cells as a full cellular immune response.

The Construction of the Fusion Protein of the Therapeutic Polypeptide, the pCloud Polypeptide and the Scaffold Protein In this invention, the therapeutic polypeptide is connected to one or more pCloud sequences and the scaffold protein to extend the in vivo half life of the therapeutic polypeptide. The pCloud sequence can be placed at either or both of the N-terminal and the C-terminal end of the therapeutic polypeptide. The pCloud sequences can also be placed at either or both of the N-terminal and the C-terminal end of the scaffold protein. The pCloud sequences within the fusion protein could be the same or be different from each other.

In some embodiments, the fusion protein of the present invention is configured using the following formula:

$$(pCloud)_m\text{-}TP\text{-}(pCloud)_n\text{-}Scaffold\text{-}(pCloud)_k \text{ or}$$

$$(pCloud)_m\text{-}Scaffold\text{-}(pCloud)_n\text{-}TP\text{-}(pCloud)_k$$

wherein:

(a) pCloud is the pCloud polypeptide characterized above, they could be different from each other.

(b) TP is a therapeutic polypeptide selected, but not limited from the group consisting of human glucagon-like peptide-1 (GLP-1), Exenatide, GLP-2, C-peptide, Calcitonin, human Parathyroid hormone (PTH), glucagon, G-CSF, GM-CSF, Interferon, interleukin factors, VEGF receptors, TNF alpha receptors, RANK, Growth hormone, Erythropoietin, blood-coagulation factors, single-chain Fv, single domain antibodies and functional variants thereof.

(c) Scaffold indicates the scaffold protein which forms a homo-trimer in solution.

(d) m is either 0 or 1; and n is either 0 or 1, k is either 0 or 1, and m+n+k>=1.

In some cases, the therapeutic polypeptide might be a short peptide (such as GLP-1 or PTH, usually a peptide not more than 100 residues). To efficiently utilize our method, the therapeutic polypeptide is connected with the pCloud sequence via a proteinous connecting moiety of human origin. A flexible loop may be utilized to fuse the therapeutic polypeptide and the proteinous connecting moiety. The flexible loop has been characterized above. The proteinous connecting moiety can stabilize the therapeutic polypeptide and further increase the hydrodynamic radius and/or the Rg of the fusion protein. In some embodiments, the proteinous connecting moiety may comprise a whole protein, a truncated version of a protein, a protein domain or domains in tandem, or protein fragments. A skilled artisan will appreciate that the proteinous connecting moiety may comprise some non-proteinous modifications which are not formed by amino acids, such as PEG.

In some embodiments, the fusion protein containing the therapeutic polypeptide, the proteinous connecting moiety, the pCloud polypeptides, and the scaffold protein of the present invention is configured according to the following formula:

$$(pCloud)_m\text{-}TP\text{-}Loop\text{-}PCM\text{-}(pCloud)_n\text{-}Scaffold\text{-}(pCloud)_k \text{ or}$$

$$(pCloud)_m\text{-}Scaffold\text{-}(pCloud)_n\text{-}PCM\text{-}Loop\text{-}TP\text{-}(pCloud)_k$$

wherein:

(a) pCloud is the pCloud polypeptide characterized above;

(b) TP is the therapeutic polypeptide selected, but not limited from the group consisting of human glucagon-like peptide-1 (GLP-1), Exenatide, GLP-2, C-peptide, Calcitonin, human Parathyroid hormone (PTH), glucagon, G-CSF, GM-CSF, Interferon, interleukin factors, VEGF receptors, TNF alpha receptors, RANK, Growth hormone, Erythropoietin, blood-coagulation factors, single-chain Fv, single domain antibodies and functional variants thereof;

(c) Scaffold indicates the scaffold protein which forms a homo-trimer in solution.

(d) m is either 0 or 1; and n is either 0 or 1, k is either 0 or 1, and m+n+k>=1.

(e) Loop is a flexible loop characterized above; and (f) PCM is the proteinous connecting moiety of human origin.

In some embodiments, the proteinous connecting moiety within the fusion protein is a proteinous sequence having an elongated shape of human origin. In some embodiments, the proteinous connecting moiety within the fusion protein is a human Fibronectin type III domain. In a particular embodiment of this invention, the proteinous connecting moiety within the fusion protein contains a human Fibronectin type III domain 8 (Fn8). Using the wild type human Fibronectin type III domain as the proteinous connecting moiety in the present invention is because Fibronectin type III domain has an elongated molecular shape and it may greatly extend the hydrodynamic radius and/or the radius of gyration of the fusion protein. This mechanism is totally different from using mutant Fibronectin type III domain as a binder to human Albumin to extend half life as shown before (patent 13).

Fibronectin (Fn) is a high-molecular weight (~440 kDa) glycoprotein of the extracellular matrix that binds to a number of proteins including integrins, collagen, fibrin and heparan sulfate proteoglycans (e.g., syndecans) [18]. Fibronectin exists as a protein dimer, consisting of two nearly identical polypeptide chains linked by a pair of C-terminal disulfide bonds. Each fibronectin monomer has a molecular weight of 230-250 kDa and contains three types of domains: type I, II, and III. Type I and type II are stabilized by intra-chain disulfide bonds, while fibronectin type III domains do not contain any disulfide bonds [19]. The Fibronectin type III domain is an evolutionary conserved protein domain that is widely found in animal proteins. The human fibronectin protein in which this domain was first identified contains 16 copies of this domain (Fn1 to Fn16). The fibronectin type III domain family (pfam ID: PF00041) member contains about 95 amino acids long and possesses a beta sandwich structure. Fibronection type III domain forms a very stable domain structure with the melting temperature of ~70° C. as measured by DSC [20, 21]. Fibronectin type III domains are found in a wide variety of extracellular proteins. In human genome, fibronection type III domain exists in many proteins including Tenascin, Usherin, Titin, tripartite motif (TRIM) family members, tissue factor, TIE1, TIE2, SPEG, SORL1, SDK1, ROBO1, ROBO2, SDK2, Receptor-type tyrosine-protein phosphatase, prolactin receptor, L1CAM, NCAM1, NCAM2, myomesin 1, myomesin 2, Myosin-binding protein C, LIFR, Leptin receptor, Integrin, Insulin receptor, Contactin, Collagen, Cytokine receptor-like factor, Inteferon receptor, Growth hormone receptor, fibronectin, leucine rich transmembrane protein (FLRT) members, IL, ephrin type-A receptor, ephrin type-B receptor, IL-6R, gp130, IL11RA, IL12RB, IL20RB, IL23R, IL27RA and IL31RA etc. Therefore, using Fibronectin type III domain as the proteinous connecting moiety in our method may have low immunogenicity. The Fibronectin type III domains can also be used in tandem fashion in the proteinous connecting moiety. In addition, Fibronectin type III domain can be expressed in recombinant form using a number of expression systems including *E. coli*, using Fibronectin type III domain as the proteinous connecting moiety in the method of the invention may greatly increase the expression yield of the fusion protein.

The Scaffold Protein

Collagens are a diverse family of proteins that constitute the major structural component of the extracellular matrix [22-24]. Collagen is composed of a triple helix, which generally consists of two identical chains (α1) and an additional chain that differs slightly in its chemical composition (α2). Classification according to supramolecular structure assigns collagens to fibril, fibril-associated containing interrupted triple helicies (FACIT), beaded filament, anchoring fibril, network-forming, transmembrane or multiple triple helicies with interruptions (Multiplexin) families [25]. To date, 43 unique α-chains that belong to 28 types of collagens (types I-XXVIII) have been discovered in vertebrates. The alpha chains of collagens consist of at least one triple helical collagenous domain of varying length and two noncollagenous (NC) domains of variable sequence, size, and shape that are positioned at the N and C terminus. The collagenous domains contain the G-X-Y repeats and form the typical triple helix within the collagen molecule while some of the NC domains form homo-trimers to stabilize the collagen triple helix. Studies on classic fibril-forming collagens found that the extreme carboxy-terminal NC (NC1) domains were essential for trimerization [26]. The Multiplexin family members also utilize NC1 domains for trimerization. On the other hand, Fibril associated-collagens (FACIT) have recently been shown to trimerize via their NC2 domains (the second NC domain from the carboxy-terminal end) [27, 28]. The crystal structures of NC1 domains from the network-forming collagens IV, VIII and X indicated these NC1 domains constituted a stable homo-trimer with the c1q-like molecular structure [29-31]. About 130 a.a. residues are present in each monomer. In contrast, the NC1 domains from the multiplexin family members such as Collagen XV and XVIII formed the much smaller homo-trimer with the length of about 55 residues in each monomer [26, 32]. Both types of the collagen NC domains form very stable homo-trimers in solution (Tm>60° C.) and are suitable as the scaffold protein as described in the invention.

Many other human proteins or domains thereof which can form homo-trimers in solution may also serve as the scaffold proteins in the method of the invention. The C1q family is characterized by a C-terminal conserved globular C1q domain (pfam ID: PF00386), which can form a stable homo-trimer [33-35]. The C1q-like protein family includes, but not limited to, human C1q A chain, C1q B chain, C1q C chain, cbln family members, human EMILIN-1, multimerin, ACRP30/adiponectin, adipolin, resistin and resistin-like molecule (RELM) hormone family members. Tumor necrosis factor (TNF) refers to a cytokine that can induce cell apoptosis and inflammation [36, 37]. TNF family (Pfam ID: PF00229) members include, but not limited, human TNFalpha, TNFbeta, TRAIL, RANK ligand, Fas ligand, CD 30 ligand, CD40 ligand, CD27 ligand, OX40L and CD137. TNF family members form homo-trimers in solution and demonstrated the similar molecular structure as the C1q family members. Therefore, these two family members are also named as C1q/TNF-related proteins (CTRP) [34].

The superfamily of proteins containing C-type lectin-like domains (CTLDs, pfam ID: PF00059) is a large group of extracellular proteins with diverse functions including cell-cell adhesion, immune response to pathogens and apoptosis [38]. A number of CTLD proteins contain a neck and a C-terminal C-type carbohydrate-recognition domain (CRD) and they form homo-trimer in solution. This type of CTLD includes mannan-binding lectin (MBL), surfactant protein A (SP-A), surfactant protein D (SP-D), collectin liver 1 (CL-L1), collectin placenta 1 (CL-P1), conglutinin, collectin of 43 kDa (CL-43) and collectin of 46 kDa (CL-46), Langerin and Tetranectin [39-42].

In this invention, the CTRP family members, including the C1q-like domains and TNF family members, can be utilized to fuse with the therapeutic polypeptide to extend the in vivo half life of the fusion protein. Alternatively, the CTLD family members can be employed as the scaffold protein to drive the trimerization of the therapeutic polypeptides.

In the preferred embodiments, the NC1 domain within Multiplexin type of human Collagen (such as collagen XV and XVIII) and NC2 domain within FACIT type of collagen (such as collagen IX, XII, XIV, XVI, XIX, XX, XXI, and XXII) may serve as the scaffold proteins in the method of this invention. The therapeutic polypeptide and the pCloud polypeptides can be fused to either the N-terminus or the C-terminus of the scaffold protein. The trimer formation of the fusion protein can efficiently increase the hydrodynamic radius of the protein molecule. The fusion protein may demonstrate a much larger apparent size than a compact molecule with the same molecular weight. Therefore the fusion protein will show a much reduced clearing rate by renal filtration and will exhibit an extended half life in vivo.

In the preferred embodiments, the NC1 domain within Multiplexin type of human Collagen (such as collagen XV and XVIII) were selected as the scaffold protein in the present invention. NC1 domain does not utilize the G-X-Y repeats and does not form the typical triple helix. In addition, no disulfide bridges between the NC1 domains are required to form the stable homo-trimer. Moreover, NC1 domain contains only about 55 amino acid residues and represents a small protein, which makes it less likely to interfere with the proper functions of the therapeutic polypeptide in the fusion protein. All the features of NC1 domain within Multiplexin type of human Collagen (such as collagen XV and XVIII) make it an ideal scaffold protein in the present invention. Using NC1 domain as the scaffold protein is preferred in the present invention, which is quite different from using other collagen domains as the scaffold protein as described elsewhere (patent 14, 15).

It will be appreciated by a skilled artisan that the term "scaffold protein" as used herein does not necessarily mean an entire wild type protein; a domain or functional variant thereof which can form a stable homo-trimer in solution and can therefore serve the purpose of the invention may also be used in our method. In some embodiments of the invention, for example, the NC1 domain within Multiplexin type of human Collagen (such as collagen XV and XVIII) was used as a scaffold protein.

The Therapeutic Polypeptide

In some embodiments of this invention, the therapeutic polypeptide may be selected from, but not limited to, human glucagon-like peptide-1 (GLP-1), Exenatide, GLP-2, C-peptide, Calcitonin, human Parathyroid hormone (PTH), glucagon, G-CSF, GM-CSF, Interferon, interleukin factors, VEGF receptors, TNF alpha receptors, RANK, Growth hormone, Erythropoietin, blood-coagulation factors, single-chain Fv, single domain antibodies and functional variants thereof. In a preferred embodiment of this invention, we use GLP-1 as one of the examples to illustrate how the method of the invention can significantly improve the pharmacokinetics property of GLP-1 and its mutants while retaining its biological activity. The natural incretin hormone glucagon-like peptide-1 (GLP-1) supports glucose homeostasis by enhancing glucose-dependent insulin secretion from β-cells and suppressing inappropriately elevated postprandial glucagon secretion from α-cells. In addition, GLP-1 has been demonstrated to reduce appetite and food intake and inhibit gastric emptying, which may facilitate weight management [43, 44]. Therefore, GLP-1 remains to be a very promising therapeutic polypeptide for type 2 diabetes and weight loss. However, GLP-1 is a 30 residue polypeptide with a very short half life in vivo, which severely limits its applications. In the present invention, we demonstrated data to show that the half life of GLP-1 can be significantly extended by use of the method of the invention.

In some other preferred embodiments of this invention, we could fuse pCloud polypeptides and the scaffold protein with the human growth hormone, human Interferon alpha-2b and human G-CSF. These therapeutic polypeptides (human growth hormone, Interferon alpha-2b and G-CSF) suffer significantly from their short in vivo half life. Fusing with pCloud polypeptide and the scaffold protein may greatly improve the pharmacokinetic profiles of the therapeutic polypeptides in vivo.

One advantage of the method of our "Trident technology" is that it can render tri-valency for the therapeutic polypeptide. It has been well documented that multivalency of protein can greatly enhance its affinity and avidity to binding partner [11, 45-47]. Antibody IgG is a Y-shaped molecule with bi-valency and utilizes two identical variable domains to interact with its ligand. The fusion protein generated using the method of the invention has tri-valency and therefore might behave better than the traditional human monoclonal antibody IgG in interacting with the ligand. For example, TNF alpha forms a homo-trimer in solution and interact with three TNF receptors simultaneously. To inhibit the TNF alpha function, TNF receptor 2 (TNFR2, p75) have been fused to IgG Fc fragment to constitute Etanercept (Enbrel) to treat severe rheumatoid arthritis. However, one Enbrel molecule can only block two out of three possible binding sites located on TNF alpha homo-trimer. In contrast, our fusion protein of TNFR2 and collagen XVIII NC1 domain generated (described below in examples) can form a homo-trimer and block all three binding sites of TNFalpha while retaining a long half life in vivo.

The scaffold protein utilized in this invention can form homo-trimers by simultaneous self assembly. In the preferred embodiments, the NC1 domain within Multiplexin type of human Collagen (such as collagen XV and XVIII) were selected as the scaffold protein. In NC1 domain, no inter-chain disulfide bonds are needed to drive the trimerization, which makes it more convenient for protein expression. Many expression systems such as *E. coli*, yeast, insect cell and mammalian cell systems can be utilized to express the fusion proteins generated by the invention. In the sharp contrast, therapeutic monoclonal antibodies rely purely on the mammalian systems for mass productions.

Summary for Trident Technology

Improving the pharmacokinetic property of a therapeutic polypeptide may have major impacts on its clinical application. In the case of GLP-1, extending its in vivo half life transformed it into a practical drug with great efficacy and broad markets. It is well known that increasing the apparent molecular weight (hydrodynamic radius and/or radius of gyration) of a therapeutic polypeptide can result in an improvement in the pharmacokinetic behavior of the therapeutic polypeptide possibly due to the slower renal clearance. The apparent molecular weight (the hydrodynamic radius and/or Rg) of a protein is determined by its molecular weight as well as by its structure, including shape and compactness. The flexible unstructured polypeptides (in preferred embodiments, pCloud polypeptides) can adopt unstructured conformations due to electrostatic repulsion between individual charges of the polypeptide and/or the inherent flexibility imparted by the particular amino acids in the sequence that lack potential to confer secondary structures. The extended and unstructured conformation of the flexible unstructured polypeptides (in preferred embodiments, pCloud polypeptides) may have a greater proportional hydrodynamic radius and/or Rg compared to polypeptides of a comparable sequence length and/or molecular weight that have tight secondary and/or tertiary structures, such as typical globular proteins. Methods for determining the hydrodynamic radius and/or Rg are well known in the art, such as by the use of size exclusion chromatography (SEC), as described in U.S. Pat. Nos. 6,406,632 and 7,294,513.

In one aspect, the present invention provides a novel technique termed as "Trident technology" which allows the therapeutic polypeptide to fuse with one or more flexible unstructured polypeptides (in preferred embodiments, pCloud polypeptides) and a trimeric scaffold protein. The trimer formation may greatly increase the hydrodynamic radius of the fusion molecule and improve the in vivo half life of the fusion protein. In addition, the flexible unstructured polypeptides (in preferred embodiments, pCloud polypeptides) may act like PEG molecules and increase the apparent size of the fusion protein. As the result, fusing the therapeutic polypeptide with flexible unstructured polypeptides (in preferred embodiments, pCloud polypeptides) and the trimeric scaffold protein may render the fusion protein a much larger apparent molecular size compared to a compactly folded globular protein with the same molecular weight. This will greatly improve the pharmacokinetic profile of the therapeutic polypeptide. In some embodiments, fragments derived from human fibrinogen alpha chain sequence were utilized as the building blocks to generate the pCloud polypeptides which rendered low immunogenicity when administered to human. Moreover, the method of the invention can provide the therapeutic polypeptide with tri-valency, which may greatly increase the affinity and avidity of the fusion protein toward the ligand.

To further extend the in vivo half life of the fusion protein generated by the method of the invention, the fusion protein can be further modified by PEGylation. The PEG moiety may have a molecular weight of between 2 kDa and 100 kDa. For specific PEGylation, the Cys residue may need to be generated in the fusion protein using site-directed mutagenesis.

Methods of Preparing Fusion Proteins Generated by the Present Invention

The fusion proteins of the present invention can be produced through the application of recombinant DNA technology. Recombinant polynucleotide constructs encoding a fusion polypeptide of the present invention typically include an expression control sequence operably-linked to the coding sequences of the fusion polypeptide, including naturally-associated or heterologous promoter regions. As such, another aspect of the invention includes vectors containing one or more nucleic acid sequences encoding a fusion polypeptide of the present invention. For recombinant expression of one or more polypeptides of the invention, the nucleic acid containing all or a portion of the nucleotide sequence encoding the fusion polypeptide is inserted into an appropriate cloning vector, or an expression vector (i.e., a vector that contains the necessary elements for the transcription and translation of the inserted polypeptide coding sequence) by recombinant DNA techniques well known in the art and as detailed below. Methods for producing diverse populations of vectors have been described by Lerner et al., U.S. Pat. Nos. 6,291,160; 6,680,192.

In general, expression vectors useful in recombinant DNA techniques are often in the form of plasmids. In some embodiments of the present invention, "plasmid" and "vector" can be used interchangeably as plasmid is the most commonly used form of vector. However, the invention is intended to include such other forms of expression vectors that are not technically plasmids, such as viral vectors (e.g., replication defective retroviruses, adenoviruses and adeno-associated viruses), which serve equivalent functions. Preferably, the expression control sequences are eukaryotic promoter systems in vectors capable of transforming or transfecting eukaryotic host cells. Once the vector has been incorporated into the appropriate host, the host is maintained under conditions suitable for high level expression of the nucleotide sequences encoding the fusion polypeptide. These expression vectors are typically replicable in the host organisms either as episomes or as an integral part of the host chromosomal DNA. Commonly, expression vectors contain selection markers, e.g., ampicillin-resistance or kanamycin-resistance, to permit detection of those cells transformed with the desired DNA sequences. Vectors can also encode a signal peptide, e.g., pectate lyase, useful to direct the secretion of extracellular antibody fragments. See U.S. Pat. No. 5,576,195.

The recombinant expression vectors of the invention may comprise a nucleic acid encoding a fusion polypeptide in a form suitable for expression of the nucleic acid in a host cell, which means that the recombinant expression vectors may include one or more regulatory sequences selected on the basis of the host cells to be used for expression that are operatively-linked to the nucleic acid sequence to be expressed. Within a recombinant expression vector, "operably-linked" is intended to mean that the nucleotide sequence of interest is linked to the regulatory sequence(s) in a manner that allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, e.g., in Goeddel, GENE EXPRESSION TECHNOLOGY: METHODS IN ENZYMOLOGY 185, Academic Press, San Diego, Calif. (1990). Regulatory sequences include those that direct constitutive expression of a nucleotide sequence in many types of host cell and those that direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of polypeptide desired, etc.

Another aspect of the invention pertains to the fusion polypeptide-expressing host cells, which contain a nucleic acid encoding one or more fusion polypeptides. The recombinant expression vectors of the invention can be designed for expression of a fusion polypeptide in prokaryotic or eukaryotic cells. For example, a fusion polypeptide can be expressed in bacterial cells such as *Escherichia coli*, insect cells, fungal cells, e.g., yeast, or mammalian cells. Suitable host cells are discussed further in Goeddel, GENE EXPRESSION TECHNOLOGY: METHODS IN ENZYMOLOGY 185, Academic Press, San Diego, Calif. (1990). Alternatively, the recombinant expression vector can be transcribed and translated in vitro, e.g., using T7 promoter regulatory sequences and T7 polymerase.

Expression of polypeptides in prokaryotes is most often carried out in *E. coli* with vectors containing constitutive or inducible promoters directing the expression of the recombinant polypeptides. The vectors may add a number of amino acids to a polypeptide encoded therein, usually to the amino terminus of the recombinant polypeptide. Such vectors with extra amino acid residues typically serve three purposes: (i) to increase expression of recombinant polypeptide; (ii) to direct the recombinant protein to periplasmic space; and (iii) to aid in the purification of the recombinant polypeptide by acting as a ligand in affinity purification. Typical expression vectors serving this purpose include pGEX (GE Healthcare), pMAL (New England Biolabs), pET20b (Novagen), pET43b (Novagen), pET32b (Novagen) and pRIT5 (GE Healthcare).

Examples of suitable inducible *E. coli* expression vectors include pTrc vectors (Invitrogen), pQE (Qiagen) and pET vectors (Novagen). One strategy to maximize recombinant polypeptide expression is to alter the nucleic acid sequence of the nucleic acid to be inserted into an expression vector so that the individual codons for each amino acid are those preferentially utilized in the expression host, e.g., *E. coli*. Such alteration of nucleic acid sequences of the invention can be carried out by standard DNA synthesis techniques.

In another embodiment, the fusion polypeptide expression vector is a yeast expression vector. Examples of vectors for expression in yeast *Saccharomyces* cerivisae include pYES2 (Invitrogen), pMFa and pJRY88. The fusion protein may also be expressed in *Pichia* system using the vectors pPICZ pGAPZ and pPIC9 (Invitrogen). Alternatively, a fusion polypeptide can be expressed in insect cells using baculovirus expression vectors or using the stable insect cell lines. Baculovirus systems available for expression of polypeptides in cultured insect cells (e.g., SF9 cells) include the BaculoGold system (BD Biosciences), BaculoDirect system (Invitrogen) and BacVector system (Novagen). The stable insect expression systems include, but not limited to, DES system (Invitrogen) and InsectDirect (Novagen).

In another embodiment, a nucleic acid encoding a fusion polypeptide of the invention is expressed in mammalian cells using a mammalian expression vector. Examples of mammalian expression vectors include, e.g., but are not limited to, pcDNA3.1 (Invitrogen), pSecTag (Invitrogen), and pTriEx series vectors (Novagen). When used in mammalian cells, the expression vector's control functions are often provided by viral regulatory elements. For example, commonly used promoters are derived from polyoma, adenovirus 2, cytomegalovirus, and simian virus 40. For other suitable expression systems for both prokaryotic and eukaryotic cells useful for expression of the fusion polypeptide of the present invention, please see, e.g., Chapters 16 and 17 of Sambrook, et al., MOLECULAR CLONING: A LABORATORY MANUAL. 2nd ed., Cold Spring Harbor Laboratory, Cold Spring Harbor Laboratory Press, Cold Spring Harbor, N.Y., 1989.

In the eukaryotic expression systems, the recombinant fusion protein can be expressed in the cytoplasm. Or alternatively, the fusion protein can be secreted into the medium by adding an N-terminal secretion signal.

Another aspect of the invention pertains to host cells into which a recombinant expression vector of the invention is to be introduced. The terms "host cell" and "recombinant host cell" are used interchangeably herein. It is understood that such terms refer not only to the particular subject cell but also to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, a fusion polypeptide can be expressed in bacterial cells such as *E. coli*, insect cells, yeast or mammalian cells. Mammalian cells are a preferred host for expressing nucleotide segments encoding immunoglobulins or fragments thereof. See Winnacker, *From Genes To Clones*, (VCH Publishers, N Y, 1987). A number of suitable host cell lines capable of secreting intact heterologous proteins have been developed in the art, and include Chinese hamster ovary (CHO) cell lines, 293 cells, various COS cell lines, HeLa cells, L cells and myeloma cell lines. Preferably, the cells are nonhuman. Expression vectors for these cells can include expression control sequences, such as an origin of replication, a promoter, an enhancer, and necessary processing information sites, such as ribosome binding sites, RNA splice sites, polyadenylation sites, and transcriptional terminator sequences. Preferred expression control sequences are promoters derived from endogenous genes, cytomegalovirus, SV40, adenovirus, bovine papillomavirus, and the like. Other suitable host cells are known to those skilled in the art.

For stable transfection of mammalian cells, it is known that, depending upon the expression vector and transfection technique used, only a small fraction of cells may integrate a foreign DNA into their genome. In order to identify and select these integrants, a gene that encodes a selectable marker (e.g., resistance to antibiotics) is generally introduced into the host cells along with the gene of interest. Various selectable markers include those that confer resistance to drugs, such as G418, hygromycin and methotrexate. Nucleic acid encoding a selectable marker can be introduced into a host cell on the same vector as that encoding the fusion polypeptide or can be introduced on a separate vector. Cells stably transfected with the introduced nucleic acid can be identified by drug selection (e.g., cells that have incorporated the selectable marker gene will survive, while the other cells die).

Once expressed, the fusion polypeptides are purified from culture media and/or host cells. Purification of recombinant polypeptides is well known in the art and includes ammonium sulfate precipitation, affinity chromatography purification technique, column chromatography, ion exchange purification technique, gel filtration and the like (see generally Scopes, Protein Purification (Springer-Verlag, N.Y., 1982).

Formulation of Pharmaceutical Compositions

The present invention envisions treating a disease, for example, type II diabetes, in a mammal by the administration of the fusion protein compositions of the present invention. Administration of the fusion protein in accordance with the present invention may be continuous or intermittent, depending, for example, upon the recipient's physiological condition, whether the purpose of the administration is therapeutic or prophylactic, and other factors known to skilled practitioners. The administration of the vaccines of the invention may be essentially continuous over a preselected period of time or may be in a series of spaced doses. Both local and systemic administration is contemplated.

The pharmaceutical composition of the present invention may be delivered via various routes and to various sites in a mammal body to achieve a particular effect. One skilled in the art will recognize that although more than one route can be used for administration, a particular route can provide a more immediate and more effective reaction than another route. Local or systemic delivery can be accomplished by administration comprising application or instillation of the formulation into body cavities, inhalation or insufflation of an aerosol, or by parenteral introduction, comprising intramuscular, intravenous, peritoneal, subcutaneous, intradermal, as well as topical administration.

The amount of the administered fusion protein of the present invention will vary depending on various factors including, but not limited to, the particular disease, the weight, the physical condition, and the age of the mammal, and whether prevention or treatment is to be achieved. Such factors can be readily determined by the clinician employing animal models or other test systems which are well known to the art. Generally, the amount of the fusion protein of the present invention to be administered to a mammal subject may vary in the range of 1 ng/kg to 100 mg/kg of the subject body weight. In an embodiment of the invention, the amount of administration was from 1 ug/kg to 1.0 mg/kg.

When the fusion proteins of the invention are prepared for administration, they are preferably combined with a pharmaceutically acceptable carrier to form a pharmaceutical formulation, or unit dosage form. Commonly used pharmaceutically acceptable carriers are well known to a skilled artisan in the field of pharmacy. The total active ingredients in such formulations include from 0.1 to 99.9% by weight of the formulation. The active ingredient for administration may be present as a powder or as granules; as a solution, a suspension or an emulsion.

Thus, the therapeutic agent may be formulated for parenteral administration (e.g., by injection, for example, bolus injection or continuous infusion) and may be presented in unit dosage form in ampules, pre-filled syringes, small volume infusion containers or in multi-dose containers with an added preservative. The active ingredients may take such forms as suspensions, solutions, or emulsions in oily or aqueous vehicles, and may contain formulatory agents such as suspending, stabilizing and/or dispersing agents. Alternatively, the active ingredients may be in powder form, obtained by aseptic isolation of sterile solid or by lyophilization from solution, for re-constitution with a suitable vehicle, e.g., sterile, pyrogen-free water, before use.

In general, water, suitable oil, saline, aqueous dextrose (glucose), and related sugar solutions and glycols such as propylene glycol or polyethylene glycols are suitable carriers for parenteral solutions. Solutions for parenteral administration contain the active ingredient, suitable stabilizing agents and, if necessary, buffer substances. Antioxidizing agents such as sodium bisulfate, sodium sulfite or ascorbic acid, either alone or combined, are suitable stabilizing agents. Also used are citric acid and its salts and sodium ethylenediaminetetraacetic acid (EDTA). In addition, parenteral solutions can contain preservatives such as benzalkonium chloride, methyl- or propyl-paraben and chlorobutanol. Suitable pharmaceutical carriers are described in *Remington's Pharmaceutical* Sciences, a standard reference text in this field.

Additionally, standard pharmaceutical methods can be employed to control the duration of action. These are well known in the art and include control release preparations and can include appropriate macromolecules, for example polymers, polyesters, polyamino acids, polyvinyl, pyrolidone, ethylenevinylacetate, methyl cellulose, carboxymethyl cellulose or protamine sulfate. The concentration of macromolecules as well as the methods of incorporation can be adjusted in order to control release. Additionally, the agent can be incorporated into particles of polymeric materials such as polyesters, polyamino acids, hydrogels, poly (lactic acid) or ethylenevinylacetate copolymers. In addition to being incorporated, these agents can also be used to trap the compound in microcapsules.

The terms "pharmaceutically-acceptable," "physiologically-tolerable," and grammatical variations thereof, as they refer to compositions, carriers, and reagents, are used interchangeably and represent that the materials are capable of administration to or upon a subject without the production of undesirable physiological effects to a degree that would prohibit administration of the composition.

Preferred examples of such carriers include, but are not limited to, water, saline, Ringer's solutions, and dextrose solution. Liposomes and non-aqueous vehicles such as fixed oils may also be used. The use of such media and compounds for pharmaceutically active substances is well known in the art. Except insofar as any conventional media or compound is incompatible with the fusion polypeptides, use thereof in the compositions is contemplated. Supplementary active compounds can also be incorporated into the compositions.

A pharmaceutical composition of the invention is formulated to be compatible with its intended route of administration. The fusion polypeptides compositions of the present invention can be administered by parenteral, topical, intravenous, oral, subcutaneous, intraarterial, intradermal, transdermal, rectal, intracranial, intraperitoneal, intranasal; intramuscular route or as inhalants. The fusion polypeptides can optionally be administered in combination with other agents that are at least partly effective in treating various diseases including various actin- or microfilament-related diseases.

Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial compounds such as benzyl alcohol or methyl parabens; antioxidants such as ascorbic acid or sodium bisulfite; chelating compounds such as ethylenediaminetetraacetic acid (EDTA); buffers such as acetates, citrates or phosphates, and compounds for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, e.g., water, ethanol, polyol (e.g., glycerol, propylene glycol, and liquid polyethylene glycol, and the like), and suitable mixtures thereof. The proper fluidity can be maintained, e.g., by the use of a coating such as lecithin, by the maintenance of the required particle size in the case of dispersion and by the use of surfactants. Prevention of the action of microorganisms can be achieved by various antibacterial and antifungal compounds, e.g., parabens, chlorobutanol, phenol, ascorbic acid, thimerosal, and the like. In many cases, it will be preferable to include isotonic compounds, e.g., sugars, polyalcohols such as manitol, sorbitol, sodium chloride in the composition. Prolonged absorption of the injectable compositions can be brought about by including in the composition a compound which delays absorption, e.g., aluminum monostearate and gelatin.

Sterile injectable solutions can be prepared by incorporating the fusion polypeptides in the required amount in an appropriate solvent with one or a combination of ingredients enumerated above, as required, followed by filtered sterilization. Generally, dispersions are prepared by incorporating the binding agent into a sterile vehicle that contains a basic dispersion medium and the required other ingredients from those enumerated above. In the case of sterile powders for the preparation of sterile injectable solutions, methods of preparation are vacuum drying and freeze-drying that yield a powder of the active ingredient plus any additional desired ingredient from a previously sterile-filtered solution thereof. The agents of this invention can be administered in the form of a depot injection or implant preparation which can be formulated in such a manner as to permit a sustained or pulsatile release of the active ingredient.

Oral compositions generally include an inert diluent or an edible carrier. They can be enclosed in gelatin capsules or compressed into tablets. For the purpose of oral therapeutic administration, the binding agent can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding compounds, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating compound such as alginic acid, Primogel, or corn starch; a lubricant such as magnesium stearate or Sterotes; a glidant such as colloidal silicon dioxide; a sweetening compound such as sucrose or saccharin; or a flavoring compound such as peppermint, methyl salicylate, or orange flavoring.

For administration by inhalation, the fusion polypeptides are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, e.g., for transmucosal administration, detergents, bile salts, and fusidic acid derivatives. Transmucosal administration can be accomplished through the use of nasal sprays or suppositories. For transdermal administration, the fusion polypeptides are formulated into ointments, salves, gels, or creams as generally known in the art.

The fusion polypeptides can also be prepared as pharmaceutical compositions in the form of suppositories (e.g., with conventional suppository bases such as cocoa butter and other glycerides) or retention enemas for rectal delivery.

EXAMPLES

The present invention is further illustrated by the following examples, which should not be construed as limiting in any way.

Example 1. Construction of an Expression Vector of GLP-1 Fused with Human Fibronectin Type III Domain 7 (Fn7) and Human Collagen XVIII NC1 Domain (COL18NC1)

In this example, GLP-1 polypeptide was fused to the N-terminus of the human collagen XVIII NC1 domain (COL18NC1) which forms a stable homo-trimer. To further extend the Rg of the molecule, the human Fibronectin type III domain 7 (Fn7) was utilized as the proteinous connecting moiety. Fn7 was connected to the GLP-1 polypeptide and COL18NC1 through a flexible loop (GGGSGGGG; SEQ ID NO:77) and a flexible, unstructured linker (GGGSGG; SEQ ID NO:89). The pET29b vector (Novagen) was used to construct a recombinant plasmid containing the GLP-1-Fn7-COL18NC1 fusion gene. First, human COL18NC1 was cloned into pET29b by BamHI and XhoI to result in the pET29b-COL18NC1 vector. PCR reaction was carried out using human collagen XVIII cDNA as the template by using the following primers:

```
                                   (SEQ ID NO:78)
Col18NC1-forward:
CGGGATCCGGTGGCGGCGCCTCCTCAGGGGTGAGG (SEQ ID NO:79)
Col18NC1-reverse:
CCGCTCGAGTTACCCTCGTGGGAGTGGTGTCCGGGCCTCC
```

The PCR product was digested by restrictive enzyme BamHI and XhoI (Fermentas) and ligated into the pET29b vector by use of T4 ligase (Fermentas). The sequence of resulted pET29b-COL18NC1 vector was confirmed by DNA sequencing.

PCR reaction was carried out using human Fibronectin cDNA as the template by using the following primers:

```
Glp1-Fn7-Forward:
GGAATTCCATATGCATGCCGAAGGGACTTTTACCAGTGATGTAAGTTCTT

ATTTGGAAGGTCAAGCTGCAAAAGAATTCATTGCTTGGCTGGTGAAAGGC

CGTGGTGGTGGCGGCTCTGGTGGCGGTGGCACACCATTGTCTCCACCAAC

AAACTTGCATCTG (SEQ ID NO:80)

Glp1-Fn7-Reverse:
CGGGATCCACCACCAGCTGGGATGATGGTATCAGAGATAGGGACACTTTC

C (SEQ ID NO:81)
```

The PCR product was digested by restrictive enzyme NdeI and BamHI (Fermentas) and ligated into the digested pET29b-COL18NC1 vector. The optimized DNA sequence of human GLP-1 (7-37) was included in the primer named as Glp1-Fn7-Forward. The cloned GLP-1-Fn7-COL18NC1 fusion gene was confirmed by DNA sequencing. The protein sequence of GLP-1-Fn7-COL18NC1 was listed as SEQ ID NO: 1.

```
                                           SEQ ID NO: 1
GLP-1-Fn7-COL18NC1 protein sequence. Fn7 is
connected to GLP-1 and COL18NC1 by use of a
flexible loop and a flexible unstructured linker.
The flexible loop between GLP-1 and Fn7
(GGGSGGGG; SEQ ID NO:77) is underlined.
The flexible, unstructured linker
(GGGSGG; SEQ ID NO:89) between Fn7 and COL18NC1
is also underlined. GLP-1 sequence is in italic.,
HAEGTFTSDVSSYLEGQAAKEFIAWLVKGRGGGSGGGG

TPLSPPTNLHLEANPDTGVLTVSWERSTTPDITGYRITTTPTNGQQGNSL

EEVVHADQSSCTFDNLSPGLEYNVSVYTVKD

DKESVPISDTIIPAGGGSGGGASSGVRLWATRQAMLGQVHEVPEGWLIFV

AEQEELYVRVQNGFRKVQLEARTPLPRG
```

Example 2. Cloning of GLP-1 Fused with Fibronectin Type III Domain 8 (Fn8) and Human Collagen XVIII NC1 Domain (COL18NC1)

Other human Fibronectin type III domains may also act as the proteinous connecting moiety between the therapeutic polypeptide and the scaffold protein in our method. In this example, we showed that Fibronectin type III domain 8 (Fn8) can be utilized as the proteinous connecting moiety between GLP-1 and collagen XVIII NC1 domain. The gene encoding GLP-1 and human Fibronectin type III domain 8 (Fn8) was amplified by PCR using the following primers and human Fibronectin cDNA as the template:

```
Fn8-Forward:
GGAATTCCATATGCATGCCGAAGGGACTTTTACCAGTGATGTAAGTTCTT

ATTTGGAAGGTCAAGCTGCAAAAGAATTCATTGCTTGGCTGGTGAAAGGC

CGTGGTGGTGGCGGCTCTGGTGGCGGTGGCTCTGCTGTTCCTCCTCCCAC

TGACCTGCGATTC (SEQ ID NO:82)

Fn8-Reverse:
CGGGATCCACCACCACCTGTTTTCTGTCTTCCTCTAAGAGGTGTGC
(SEQ ID NO:83)
```

The PCR product was digested by NdeI and BamHI. The digested insert was ligated into the digested vector pET29b-COL18NC1 (generated in example 1). The resulted vector was named as pET29b-GLP-1-Fn8-COL18NC1. The protein sequence of the fusion protein GLP-1-Fn8-COL18NC1 was listed as SEQ ID NO: 2.

```
                                           SEQ ID NO: 2
GLP-1-Fn8-COL18NC1 protein sequence, GLP-1
sequence is in italic. Fn8 is connected to GLP-1
and COL18NC1 by use of a flexible loop and a
flexible unstructured linker. The flexible loop
between GLP-1 and Fn8
(GGGSGGGGS; SEQ ID NO:90) is underlined.
The flexible unstructured linker (GGGSGG; SEQ ID
NO:89) between Fn8 and COL18NC1 is also under-
lined,.
HAEGTFTSDVSSYLEGQAAKEFIAWLVKGRGGGSGGGGSAVPPPTDLRF

TNIGPDTMRVTWAPPPSIDLTNFLVRYSPVK

NEEDVAELSISPSDNAVVLTNLLPGTEYVVSVSSVYEQHESTPLRGRQKT

G

GGGSGGGASSGVRLWATRQAMLGQVHEVPEGWLIFVAEQEELYVRVQNGF

RKVQLEARTPLPRG
```

Example 3. Expression and Purification of Fusion Protein GLP-1-Fn8-COL18NC1

The constructed expression vector pET29b-Glp1-Fn8-COL18NC1, after sequencing confirmation, was used to transform *Escherichia coli* BL21 (DE3) for protein expression (for detailed protocols of the transformation, see *Molecular Colning: A Laboratory Manual*). A single colony was selected from the culture dish, and placed into a 10 ml LB liquid medium with kanamycin (final concentration, 50 µg/ml), then shaken at 37° C. at 220 rpm overnight. 1L LB culture was inoculated and allowed to grown until $OD_{600}$ reached 0.4-1.0. Isopropyl thiogalactoside (IPTG) was added to a final concentration of 0.2 mM. After a successive culture at 30° C. for overnight, cells were collected by centrifugation. The cells were diluted 1:20 with 20_mM Tris, NaCl 50_mM, 2 mM EDTA, pH 8.0, and, after a thorough mix, disrupted by sonication. Insoluble precipitates were removed by centrifugation at 13,000 RCF for 30 min. The proteins of interest were present in the supernatant, with the expressed product comprising 20% of soluble proteins. 50 ml of the supernatant was loaded on a HiTrap Q column (5 ml) (GE Healthcare). The fusion protein of GLP1-Fn8-COL18NC1 was eluted with about 0.3 M NaCl in the buffer. The eluted protein was further purified by use of a gel filtration column S-200 (GE Healthcare), and the buffer was replaced with PBS (pH 7.5). The final product was confirmed by SDS-PAGE electrophoresis.

Example 4: GLP-1 Mutants Fused with Fn8-COL18NC1

The mutations of A8G/G22E, A8V/G22E, A8S/G22E, A8G/G22E/R36S and A8G/G22E/R36G within the GLP-1 sequence may increase its resistance to protease digestion, reduce immunogenicity and boost its biological activity [6, 48]. In this example, we constructed a vector to fuse GLP-1 (A8G/G22E) with Fibronectin type III domain 8 and collagen XVIII NC1 domain. The PCR reaction was carried out using vector pET29b-GLP1-Fn8-COL18NC1 prepared in example 2 as the template with the following primers:

```
Glp-1(A8 G/G22E)-Fn8-forward:
GGAATTCCATATGCATGGCGAAGGGACTTTTACCAGTGATGTAAGTTCTT
ATTTGGAAGAGCAAGCTGCAAAAGAATTCATTGC (SEQ ID NO:84)

Col18NC 1-reverse:
CCGCTCGAGTTACCCTCGTGGGAGTGGTGTCCGGGCCTCC
(SEQ ID NO:85)
```

The PCR product was digested by NdeI and XhoI (Fermentas). The digested insert was ligated into the digested vector of pET29b. The resulted vector was named as pET29b-GLP1(A8G/G22E)-Fn8-COL18NC1. The expression and purification protocol of the fusion protein of GLP-1(A8G/G22E)-Fn8-COL18NC1 was the same as described in example 3. Other mutations within the GLP-1, such as A8V/G22E, A8S/G22E, A8G/G22E/R36S and A8G/G22E/R36G, can be generated using the Quikchange II site-directed mutagenesis kit (Agilent) using the GLP-1 (A8G/G22E)-Fn8-COL18NC1 gene as the template. The protein sequences of these GLP1 mutants fused with Fn8-COL18NC1 were listed as SEQ ID NO:3-7. The expression and purification protocol of these fusion proteins can be carried out using similar protocols described in example 3.

```
                                         SEQ ID NO: 3
GLP-1(A8G/G22E)-Fn8-COL18NC1 protein sequence, the
GLP-1 mutation sites (A8G/G22E) are underlined,.
HGEGTFTSDVSSYLEEQAAKEFIAWLVKGRGGGGSGGGGSAVPPPTDLRF

TNIGPDTMRVTWAPPPSIDLTNFLVRYSPVK

NEEDVAELSISPSDNAVVLTNLLPGTEYVVSVSSVYEQHESTPLRGRQKT

G

GGGSGGGASSGVRLWATRQAMLGQVHEVPEGWLIEVAEQEELYVRVQNGF

RKVQLEARTPLPRG

SEQ ID NO: 4
GLP-1(A8V/G22E)-Fn8-COL18NC1 protein sequence, the
GLP-1 mutation sites (A8V/G22E) are underlined,.
HVEGTFTSDVSSYLEEQAAKEFIAWLVKGRGGGGSGGGGSAVPPPTDLRF

TNIGPDTMRVTWAPPPSIDLTNFLVRYSPVK

NEEDVAELSISPSDNAVVLTNLLPGTEYVVSVSSVYEQHESTPLRGRQKT

G

GGGSGGGASSGVRLWATRQAMLGQVHEVPEGWLIFVAEQEELYVRVQNGF

RKVQLEARTPLPRG

SEQ ID NO: 5
GLP-1(A8S/G22E)-Fn8-COL18NC1 protein sequence, the
GLP-1 mutation sites (A8S/G22E) are underlined,.
HSEGTFTSDVSSYLEEQAAKEFIAWLVKGRGGGGSGGGGSAVPPPTDLRF

TNIGPDTMRVTWAPPPSIDLTNFLVRYSPVK

NEEDVAELSISPSDNAVVLTNLLPGTEYVVSVSSVYEQHESTPLRGRQKT

G

GGGSGGGASSGVRLWATRQAMLGQVHEVPEGWLIFVAEQEELYVRVQNGF

RKVQLEARTPLPRG

SEQ ID NO: 6
GLP-1(A8G/G22E/R36S)-Fn8-COL18NC1 protein
sequence, the GLP-1 mutation sites (A8G/G22E/R36S)
are underlined,.
HGEGTFTSDVSSYLEEQAAKEFIAWLVKGSGGGGSGGGGSAVPPPTDLRF

TNIGPDTMRVTWAPPPSIDLTNFLVRYSPVK

NEEDVAELSISPSDNAVVLTNLLPGTEYVVSVSSVYEQHESTPLRGRQKT

G

GGGSGGGASSGVRLWATRQAMLGQVHEVPEGWLIFVAEQEELYVRVQNGF

RKVQLEARTPLPRG

SEQ ID NO: 7
GLP-1(A8G/G22E/R36G)-Fn8-COL18NC1 protein
sequence, the GLP-1 mutation sites (A8G/G22E/R36G)
are underlined,.
HGEGTFTSDVSSYLEEQAAKEFIAWLVKGGGGGGSGGGGSAVPPPTDLRF

TNIGPDTMRVTWAPPPSIDLTNFLVRYSPVK

NEEDVAELSISPSDNAVVLTNLLPGTEYVVSVSSVYEQHESTPLRGRQKT

G

GGGSGGGASSGVRLWATRQAMLGQVHEVPEGWLIFVAEQEELYVRVQNGF

RKVQLEARTPLPRG
```

Example 5

Between the Therapeutic Polypeptides and the Scaffold Proteins, various lengths of the flexible un-structured linkers can be used to generate the fusion proteins with the desired hydrodynamic radius and/or radius of gyration (Rg)

In this example, we presented data to demonstrate that the flexible unstructured linkers with various lengths can be utilized in our method to adjust the hydrodynamic radius and/or Rg of the fusion protein. It is well established that a protein with a larger hydrodynamic radius and/or Rg may exhibit a longer half life in vivo. Therefore, the method of the invention may adjust the in vivo half life of the therapeutic polypeptide in a tunable fashion.

In the fusion protein of GLP-1(A8G/G22E)-Fn8-COL18NC1 described in example 4, the flexible unstructured linker between Fn8 and COL18NC1 contains six residues (GGGSGG; SEQ ID NO:89). To generate the flexible un-structured linkers with different lengths, we have synthesized the genes GLP-1(A8G/G22E/R36S)-Fn8-COL18NC1-20, GLP-1(A8G/G22E/R36S)-Fn8-COL18NC1-30, GLP-1(A8G/G22E/R36S)-Fn8-COL18NC1-54 and GLP-1(A8G/G22E/R36S)-Fn8-COL18NC1-60. In these genes, the length of the flexible unstructured polypeptide linker between Fn8 and COL18NC1 contained 20, 30, 54 and 60 residues, respectively. The protein sequences of GLP-1(A8G/G22E/R36S)-Fn8-COL18NC1-20, GLP-1(A8G/G22E/R36S)-Fn8-COL18NC1-30, GLP-1(A8G/G22E/R36S)-Fn8-COL18NC1-54 and GLP-1(A8G/G22E/R36S)-Fn8-COL18NC1-60 are listed as SEQ ID NO:8-11. The synthetic genes of GLP-1(A8G/G22E/R36S)-Fn8-COL18NC1-20, GLP-1(A8G/G22E/R36S)-Fn8-COL18NC1-30, GLP-1(A8G/G22E/R36S)-Fn8-COL18NC1-54 and GLP-1(A8G/G22E/R36S)-Fn8-COL18NC1-60 were grafted to the pET29b by NdeI and XhoI for protein expressions. The expression and purification of these fusion proteins were carried out using similar protocols described in example 3. To estimate the hydrodynamic radius and/or the Rg of the fusion proteins, the purified proteins were loaded on an analytical gel filtration column Superdex200 (GE Healthcare).

Figure 3:
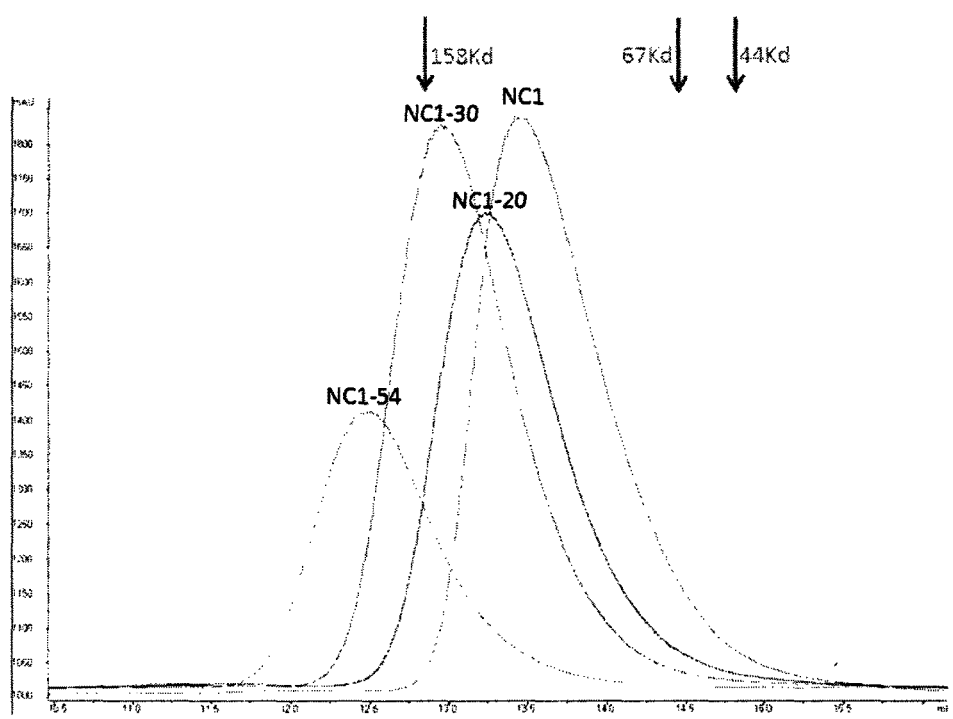
FIG. 3 shows the gel filtration chromatography profiles for purified GLP-1(A8G/G22E/R36S)-Fn8-COL18NC1, GLP-1(A8G/G22E/R36S)-Fn8-COL18NC1-20, GLP-1 (A8G/G22E/R36S)-Fn8-COL18NC1-30, and GLP-1(A8G/G22E/R36S)-Fn8-COL18NC1-54 using the analytical column Superdex200 (GE Healthcare). In this figure, the profiles of these proteins are labeled as NC1, NC1-20, NC1-30 and NC1-54. The elution time for the molecular marker proteins (158Kd, 67Kd and 44Kd) are shown by arrows. The X-axis refers to elution time and the Y-axis refers to UV280 absorbance intensity.

The gel filtration data clearly showed that varying the length of the flexible, unstructured linker between Fn8 and COL18NC1 can significantly change the apparent molecular size of the fusion proteins in solution (FIG. 3). GLP-1(A8G/G22E/R36S)-Fn8-COL18NC1 trimer exhibited an apparent molecular weight of ~100Kd while its genuine molecular weight is ~68Kd. GLP-1(A8G/G22E/R36S)-Fn8-COL18NC1-60 trimer (data not shown) and GLP-1(A8G/G22E/R36S)-Fn8-COL18NC1-54 trimer exhibited an apparent molecular weight of ~200Kd while its genuine molecular weight is ~80Kd. GLP-1(A8G/G22E/R36S)-Fn8-COL18NC1-20, GLP-1(A8G/G22E/R36S)-Fn8-COL18NC1-30 exhibited larger apparent molecular weight than their genuine molecular weight as well. Therefore, our method can provide the therapeutic polypeptide with a larger hydrodynamic Radius and/or Rg which exhibited increased apparent molecular size on gel filtration profile. Moreover, the flexible unstructured linker between the therapeutic polypeptide and the scaffold protein may adjust the hydrodynamic radius and/or the Rg of the fusion molecule in a tunable manner.

```
                                              SEQ ID NO: 8
protein sequence of GLP-1(A8G/G22E/R36S)-Fn8-
COL18NC1-20, the flexible unstructured linker (20
residues) between Fn8 and COL18NC1 is underlined.
The flexible loop between GLP-1 and Fn8
(GGGSGG; SEQ ID NO:89) is also underlined,.
HGEGTFTSDVSSYLEEQAAKEFIAWLVKGSGGGSGGAVPPPTDLRFTNI

GPDTMRVTWAPPPSIDLTNFLVRYSPVKNEEDVAELSISPSDNAVVLTNL

LPGTEYVVSVSSVYEQHESTPLRGRQKTGGGGSGGGGSGGGGSGGGGSG

ASSGVRLWATRQAMLGQVHEVPEGWLIFVAEQEELYVRVQNGFRKVQLEA

RTPLPRG

SEQ ID NO: 9
protein sequence of GLP-1(A8G/G22E/R36S)-Fn8-
COL18NC1-30, the flexible unstructured linker (30
residues) between Fn8 and COL18NC1 is underlined.
The flexible loop between GLP-1 and Fn8
(GGGSGG; SEQ ID NO:89) is also underlined,.
HGEGTFTSDVSSYLEEQAAKEFIAWLVKGSGGGSGGAVPPPTDLRFTNI

GPDTMRVTWAPPPSIDLTNELVRYSPVKNEEDVAELSISPSDNAVVLTNL

LPGTEYVVSVSSVYEQHESTPLRGRQKTG

GGGGSGGGGSASSASTGGPSGGGGSGGGGS

GASSGVRLWATRQAMLGQVHEVPEGWLIFVAEQEELYVRVQNGFRKVQLE

ARTPLPRG

SEQ ID NO: 10
protein sequence of GLP-1(A8G/G22E/R36S)-Fn8-
COL18NC1-54, the flexible unstructured linker (54
residues) between Fn8 and COL18NC1 is underlined.
The flexible loop between GLP-1 and Fn8
(GGGSGG; SEQ ID NO:89) is also underlined,.
HGEGTFTSDVSSYLEEQAAKEFIAWLVKGSGGGSGGAVPPPTDLRFTNI

GPDTMRVTWAPPPSIDLTNELVRYSPVKNEEDVAELSISPSDNAVVLTNL

LPGTEYVVSVSSVYEQHESTPLRGRQKTG

GGGGSGGGGSTASSASTGGPSGGGGSGGGGSAPSSGSTSGGTAAGGGGSG

GGGS

GASSGVRLWATRQAMLGQVHEVPEGWLIFVAEQEELYVRVQNGFRKVQLE

ARTPLPRG

SEQ ID NO: 11
protein sequence of GLP-1(A8G/G22E/R36S)-Fn8-
COL18NC1-60, the flexible unstructured linker (60
residues) between Fn8 and COL18NC1 is underlined.
The flexible loop between GLP-1 and Fn8
(GGGSGG; SEQ ID NO:89) is also underlined,.
HGEGTFTSDVSSYLEEQAAKEFIAWLVKGSGGGSGGAVPPPTDLRFTNI

GPDTMRVTWAPPPSIDLTNELVRYSPVKNEEDVAELSISPSDNAVVLTNL

LPGTEYVVSVSSVYEQHESTPLRGRQKTG

GGGSGGGSGGGSTASSASTKGPSGGGSGGGSGGGSAPSSKSTSGGTAAGG

GSGGGSGGGS

GASSGVRLWATRQAMLGQVHEVPEGWLIFVAEQEELYVRVQNGFRKVQLE

ARTPLPRG
```

Example 6: The Pharmacokinetics Studies for GLP-1(A8G/G22E/R36S)-Fn8-COL18NC1, GLP-1(A8G/G22E/R36S)-Fn8-COL18NC1-20, GLP-1(A8G/G22E/R36S)-Fn8-COL18NC1-30, GLP-1(A8G/G22E/R36S)-Fn8-COL18NC1-54

To evaluate the pharmacokinetics profiles for the GLP-1 containing fusion proteins generated using the method of the invention, we purified GLP-1(A8G/G22E/R36S)-Fn8-COL18NC1, GLP-1(A8G/G22E/R36S)-Fn8-COL18NC1-20, GLP-1(A8G/G22E/R36S)-Fn8-COL18NC1-30, GLP-1(A8G/G22E/R36S)-Fn8-COL18NC1-54 in PBS buffer, pH 7.2. These fusion proteins were administered on Sprague-Dawley (SD) rats by intraperitoneal injections at the doses of 0.66 mg/kg, 0.72 mg/kg, 0.75 mg/kg, 0.78 mg/kg animal respectively. Blood samples were taken at various time points after injections such as 0-min, 30-min, 1-hour, 2-hour, 4-hour, 8-hour, 24-hour, 48-hour, 3-day, 4-day, 5-day. 7-day, 10-day. The serum samples were centrifuged and kept at −80° C. freezer.

The GLP-1 concentrations within the serum samples were examined by use of the sandwich ELISA method. The rabbit polyclonal antibody against human Fibronectin at the concentration of 3 ug/ml (Ab299, Abcam company) was coated on ELISA plate for 1 hour at room temperature. Then the plate was washed by PBST buffer three times and the wells were blocked by PBS with 10% FBS for 1 hour at room temperature. The plate was washed three times before the serum samples containing GLP-1 fusion proteins were added. The serum samples could be diluted to 20-10000 folds before use. The ELISA plate was incubated with the serum samples at room temperature for 1 hour and then washed by PBST buffer five times. Then mouse monoclonal against human GLP-1 peptide antibody (sc57510, Santa Cruz Biotechology) at the concentration of 1 ug/ml in PBST buffer was added to the wells. The plate was washed extensively after incubation of 1 hour at room temperature. The secondary antibody, Goat anti-rabbit IgG HRP conjugated antibody (Beijing ZSGB-Bio company, ZB 5301), was added into the wells and the color was developed using TMB (3,3',5,5'-tetramethylbenzidine, BD Biosciences, Cat 555214). The plate reader (Bio-Rad microplate reader Model 680) was utilized to obtain the OD450 readings. This method has been calibrated using purified proteins first.

Figure 4:
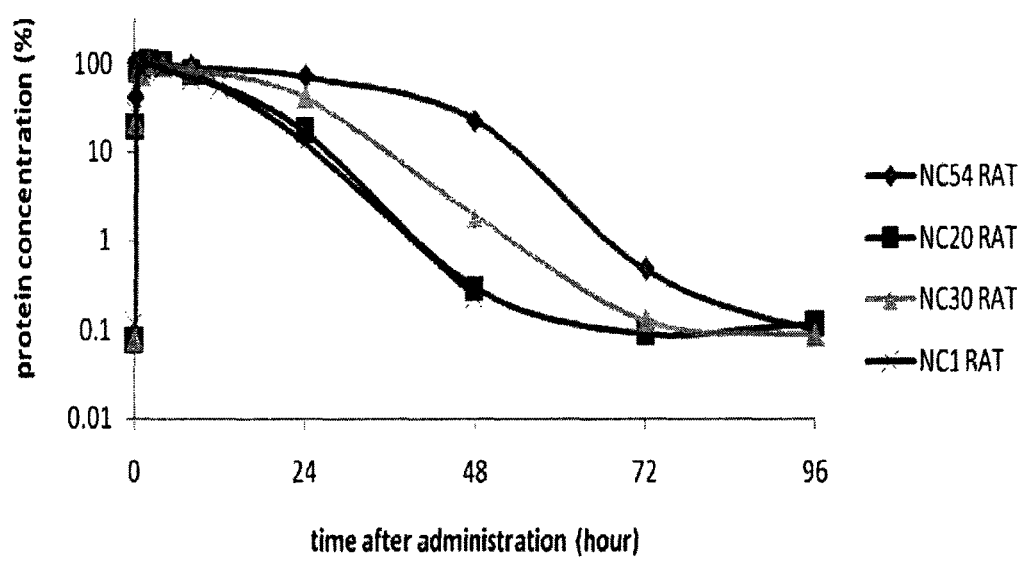
FIG. 4 shows the pharmacokinetics profiles of the GLP-1 containing proteins (GLP-1(A8G/G22E/R36S)-Fn8-COL18NC1, GLP-1(A8G/G22E/R36S)-Fn8-COL18NC1-20, GLP-1(A8G/G22E/R36S)-Fn8-COL18NC1-30 and GLP-1(A8G/G22E/R36S)-Fn8-COL18NC1-54) in Sprague Dawley rats measured by use of the sandwich ELISA method. In this figure, the profiles of these proteins are labeled as NC1, NC20, NC30 and NC54, respectively. The vertical axis indicates the percentage of the measured protein concentration by use of sandwich ELISA method compared with $C_{max}$.

FIG. 4 showed the pharmacokinetics profiles of the GLP-1 containing proteins by use of the sandwich ELISA method described above. The pharmacokinetics parameters were obtained by using the WinNonlin software (Table 3). The data clearly showed that the GLP-1 containing fusion proteins generated by use of the method of the invention exhibited much extended in vivo half life possibly due to their enlarged Rg. The data also showed that the flexible, unstructured linker between the therapeutic polypeptide and the scaffold protein may adjust the in vivo half life of the fusion molecules in a tunable manner.

TABLE 3

Pharmacokinetics parameters for the GLP-1 containing fusion proteins in Sprague-Dawley rat. GLP-1(A8G/G22E/R36S)-Fn8-COL18NC1, GLP-1(A8G/G22E/R36S)-Fn8-COL18NC1-20, GLP-1(A8G/G22E/R36S)-Fn8-COL18NC1-30, GLP-1(A8G/G22E/R36S)-Fn8-COL18NC1-54 were shown in abbreviation as NC1, NC1-20, NC1-30, and NC1-54 respectively.

|  |  | NC1 | NC1-20 | NC1-30 | NC1-54 |
|---|---|---|---|---|---|
| T½ | hour | 5.22 | 6.45 | 7.22 | 9.10 |
| Cmax | ug/ml | 1.86 | 2.26 | 2.15 | 2.64 |
| AUC(0-t) | ug * h/ml | 24.8 | 36.21 | 47.58 | 86.64 |
| AUCinf | ug * h/ml | 26.53 | 37.24 | 47.6 | 86.67 |
| V | ml/kg | 568.04 | 530.16 | 479.81 | 350.86 |
| CL | ml/h/kg | 75.96 | 57.03 | 46.04 | 27.06 |

Example 7: Construction of the Fusion Protein Containing GLP-1 Mutants, Fn8, pCloud Sequence and COL18NC1

In this example, we introduced pCloud polypeptide into the GLP-1 containing fusion protein. We constructed the vector to fuse GLP-1 wild type or its mutants with Fibronectin type III domain 8(Fn8), the pCloud polypeptide and collagen XVIII NC1 domain.

The pCloud sequence in this example (p246) comprises all the 12 fibrinogen fragments listed in Table 1. In the protein sequence of p246, the 12 fragments listed in Table 1 were placed in the order as they appear in the human fibrinogen alpha chain sequence. The flexible loops that were utilized to connect these fibrinogen-derived fragments in p246 sequence are GSGSESGSG (SEQ ID NO:69), GGGSGGGS (SEQ ID NO:86) and GGSGGGSGG (SEQ ID NO:75). The optimized gene encoding p246 and COL18NC1 was synthesized, digested by BamHI and XhoI and ligated into the digested vector of pET29b. The resulted vector was named as pET29b-p246-COL18NC1. The optimized gene encoding GLP-1(A8G/G22E) and Fn8 was synthesized, digested by NdeI and BamHI and ligated into the digested pET29b-p246-COL18NC1. The resulted vector was named as pET29b-GLP-1(A8G/G22E)-Fn8-p246-COL18NC1. The protein sequence of the fusion protein GLP-1(A8G/G22E)-Fn8-p246-COL18NC1 was listed as SEQ ID NO:12. From N-terminus to C-terminus, GLP-1(A8G/G22E)-Fn8-p246-COL18NC1 contains GLP-1(A8G/G22E), a flexible loop, Fn8, pCloud sequence p246 and the scaffold protein COL18NC1.

Other mutations within the GLP-1, such as A8V/G22E, A8S/G22E, A8G/G22E/R36S and A8G/G22E/R36G, can be generated using the Quikchange II site-directed mutagenesis kit (Agilent) using the GLP-1(A8G/G22E)-Fn8-p246-COL18NC1 gene as the template. The resulted vectors of the fusion proteins were named as pET29b-GLP-1(A8V/G22E)-Fn8-p246-COL18NC1, pET29b-GLP-1(A8S/G22E)-Fn8-p246-COL18NC1, pET29b-GLP-1(A8G/G22E/R36S)-Fn8-p246-COL18NC1 and pET29b-GLP-1(A8G/G22E/R36G)-Fn8-p246-COL18NC1. The protein sequences of these fusion proteins were listed as SEQ ID NO:13-16. The expression and purification protocol of these fusion proteins can be carried out using similar protocols described in example 3.

SEQ ID NO: 12
GLP-1(A8G/G22E)-Fn8-p246-COL18NC1 protein sequence, the GLP-1 mutation sites (A8G/G22E) are in Italic and bold. The flexible loop between GLP1(A8G/G22E) and Fn8 is in bold. The pCloud sequence p246 is underlined,.
HGEGTFTSDVSSYLEEQAAKEFIAWLVKGRGSGGGSGGGSGGGSGGG

SGSGGAVPPPTDLRFTNIGPDTMRVTWAPPPSIDLTNFLVRYSPVKNEED

VAELSISPSDNAVVLTNLLPGTEYVVSVSSVYEQHESTPLRGRQKTGGGG

SGGGSGSGSESGSGGGSTSSGTGSETESPGSGSESGSGPSSAGSGSGSES

GSGSGSSGPGSTGGSGSESGSGPGSSGTGGTATGSGSESGSGPGSSGPGS

TGSGSGSESGSGSGSSGTGSTGGSGSESGSGPGSPRPGSTGTGSGSESGS

GPGSSERGSAGGSGSESGSGTSESSASGSTGGSGSESGSGSESGSGSGSE

SGSGPESPGSGGSGSESGSGTSGSTGSGSESGSGGGSGGGSGGGASSGVR

LWATRQAMLGQVHEVPEGWLIFVAEQEELYVRVQNGFRKVQLEARTPLPR

G

SEQ ID NO: 13
GLP-1(A8V/G22E)-Fn8-p246-COL18NC1 protein sequence, the GLP-1 mutation sites (A8V/G22E) are in Italic and bold. The pCloud sequence p246 is underlined,.
HVEGTFTSDVSSYLEEQAAKEFIAWLVKGRGSGGGSGGGSGGGSGGG

SGSGGAVPPPTDLRFTNIGPDTMRVTWAPPPSIDLTNFLVRYSPVKNEED

VAELSISPSDNAVVLTNLLPGTEYVVSVSSVYEQHESTPLRGRQKTGGGG

SGGGSGSGSESGSGGGSTSSGTGSETESPGSGSESGSGPSSAGSGSGSES

GSGSGSSGPGSTGGSGSESGSGPGSSGTGGTATGSGSESGSGPGSSGPGS

TGSGSGSESGSGSGSSGTGSTGGSGSESGSGPGSPRPGSTGTGSGSESGS

GPGSSERGSAGGSGSESGSGTSESSASGSTGGSGSESGSGSESGSGSGSE

SGSGPESPGSGGSGSESGSGTSGSTGSGSESGSGGGSGGGSGGGASSGVR

LWATRQAMLGQVHEVPEGWLIFVAEQEELYVRVQNGFRKVQLEARTPLPR

G

SEQ ID NO: 14
GLP-1(A8S/G22E)-Fn8-p246-COL18NC1 protein sequence, the GLP-1 mutation sites (A8S/G22E) are in Italic and bold. The pCloud sequence p246 is underlined,.
HSEGTFTSDVSSYLEEQAAKEFIAWLVKGRGSGGGSGGGSGGGSGGG

SGSGGAVPPPTDLRFTNIGPDTMRVTWAPPPSIDLTNFLVRYSPVKNEED

VAELSISPSDNAVVLTNLLPGTEYVVSVSSVYEQHESTPLRGRQKTGGGG

SGGGSGSGSESGSGGGSTSSGTGSETESPGSGSESGSGPSSAGSGSGSES

GSGSGSSGPGSTGGSGSESGSGPGSSGTGGTATGSGSESGSGPGSSGPGS

TGSGSGSESGSGSGSSGTGSTGGSGSESGSGPGSPRPGSTGTGSGSESGS

GPGSSERGSAGGSGSESGSGTSESSASGSTGGSGSESGSGSESGSGSGSE

SGSGPESPGSGGSGSESGSGTSGSTGSGSESGSGGGSGGGSGGGASSGVR

LWATRQAMLGQVHEVPEGWLIFVAEQEELYVRVQNGFRKVQLEARTPLPR

G

SEQ ID NO: 15
GLP-1(A8G/G22E/R36S)-Fn8-p246-COL18NC1 protein sequence, the GLP-1 mutation sites (A8G/G22E/R36S) are in Italic and bold. The pCloud sequence p246 is underlined,.
HGEGTFTSDVSSYLEEQAAKEFIAWLVKGSGSGGGSGGGSGGGSG

GGSGSGGAVPPPTDLRFTNIGPDTMRVTWAPPPSIDLTNFLVRYSPVKNE

EDVAELSISPSDNAVVLTNLLPGTEYVVSVSSVYEQHESTPLRGRQKTGG

GGSGGGSGSGSESGSGGGSTSSGTGSETESPGSGSESGSGPSSAGSGSGS

ESGSGSGSSGPGSTGGSGSESGSGPGSSGTGGTATGSGSESGSGPGSSGP

GSTGSGSGSESGSGSGSSGTGSTGGSGSESGSGPGSPRPGSTGTGSGSES

GSGPGSSERGSAGGSGSESGSGTSESSASGSTGGSGSESGSGSESGSGSG

SESGSGPESPGSGGSGSESGSGTSGSTGSGSESGSGGGSGGGSGGGASSG

VRLWATRQAMLGQVHEVPEGWLIFVAEQEELYVRVQNGFRKVQLEARTPL

PRG

SEQ ID NO: 16
GLP-1(A8G/G22E/R36G)-Fn8-p246-COL18NC1 protein sequence, the GLP-1 mutation sites (A8G/G22E/R36G) are in Italic and bold. The flexible loop between GLP1(A8G/G22E/R36G) and Fn8 is in bold. The pCloud sequence p246 is underlined,.
HGEGTFTSDVSSYLEEQAAKEFIAWLVKGGGSGGGSGGGSGGGSG

GGSGSGGAVPPPTDLRFTNIGPDTMRVTWAPPPSIDLTNFLVRYSPVKNE

EDVAELSISPSDNAVVLTNLLPGTEYVVSVSSVYEQHESTPLRGRQKTGG

GGSGGGSGSGSESGSGGGSTSSGTGSETESPGSGSESGSGPSSAGSGSGS

ESGSGSGSSGPGSTGGSGSESGSGPGSSGTGGTATGSGSESGSGPGSSGP

GSTGSGSGSESGSGSGSSGTGSTGGSGSESGSGPGSPRPGSTGTGSGSES

GSGPGSSERGSAGGSGSESGSGTSESSASGSTGGSGSESGSGSESGSGSG

SESGSGPESPGSGGSGSESGSGTSGSTGSGSESGSGGGSGGGSGGGASSG

VRLWATRQAMLGQVHEVPEGWLIFVAEQEELYVRVQNGFRKVQLEARTPL

PRG

Example 8: Cloning and Expression of GLP-1(A8G/G22E/R36G) Fused with Tenascin C Fibronectin Type III Domain 3 (TNCfn3), pCloud Sequence p246 and Human Collagen XVIII NC1 (COL18NC1)

In this example, we demonstrated that the fibronectin type III domain that can be used as the proteinous connecting moiety for our method is not limited within human fibronectin. Other suitable fibronectin type III domain may alternatively be utilized as the proteinous connecting moiety in the method of the invention. Here we showed that a fibronectin type III domain from human Tenascin C can be utilized to connect the therapeutic polypeptide and the pCloud sequence as well.

In this example, the human Tenascin C fibronectin type III domain 3 (TNCfn3) was connected to the GLP-1(A8G/G22E/R36G) and the pCloud sequence as the proteinous connecting moiety. The gene encoding GLP-1(A8G/G22E/R36G), the flexible loop and TNCfn3 was synthesized, digested by NdeI and BamHI and ligated into the digested pET29b-GLP-1(A8G/G22E/R36G)-p246-COL18NC1 vector. The resulted vector was named as pET29b-GLP1(A8G/

G22E/R36G)-TNCfn3-p246-COL18NC1. The expression and purification protocol of the fusion protein GLP1(A8G/G22E/R36G)-TNCfn3-p246-COL18NC1 (SEQ ID NO:17) was the same as described in example 3.

```
                                        SEQ ID NO: 17
GLP-1(A8G/G22E/R36G)- TNCfn3-p246-COL18NC1 protein
sequence, The flexible unstructured linker between
GLP1(A8G/G22E/R36G) and TNCfn3 is in bold. The
TNCfn3 sequence is in italic. The pCloud sequence
p246 is underlined,.
HGEGTFTSDVSSYLEEQAAKEFIAWLVKGGGSGGGSGGGSGGGSGGGSGS

GG

*RLDAPSQIEVKDVTDTTALITWFKPLAEIDGIELTYGIKDVPGDRTTIDL*

*TEDENQYSIGNLKPDTEYEVSLISRRGDMSSNPAKETFTTG*

GGGSGGGSGSGSESGSGGGSTSSGTGSETESPGSG

SESGSGPSSAGSGSGSESGSGSGSSGPGSTGGSGSESGSGPGSSGTGGTA

TGSGSESGSGPGSSGPGSTGSGSGSESGSGSGSSGTGSTGGSGSESGSGP

GSPRPGSTGTGSGSESGSGPGSSERGSAGGSGSESGSGTSESSASGSTGG

SGSESGSGSESGSGSGSESGSGPESPGSGGSGSESGSGTSGSTGSGSESG

SGGGSGGGSGGGASSGVRLWATRQAMLGQVHEVPEGWLIFVAEQEELYVR

VQNGFRKVQLEARTPLPRG
```

Example 9: Cloning and Expression of GLP-1(A8G/G22E/R36G) Fused with Fn8, pCloud Sequence p246 and Human Collagen XV NC1 (COL15NC1)

In this example, we presented data to show that the NC1 domain from collagen XV can alternatively be utilized as the scaffold protein in our method. It has been reported that human collagen XV NC1 domain, like the human collagen XVIII NC1 domain, forms a stable homo-trimer [26, 32]. To generate the expression vector encoding the fusion protein of GLP1(A8G/G22E/R36G)-Fn8-p246-COL15NC1, the gene encoding pCloud sequence p246 and COL15NC1 domain was synthesized, digested by BamHI and XhoI and ligated into the digested pET29b-GLP-1(A8G/G22E/R36G)-Fn8-p246-COL18NC1 vector generated before. The resulted vector was named as pET29b-GLP1(A8G/G22E/R36G)-Fn8-p246-COL15NC1 and the sequence of the vector was confirmed by DNA sequencing. The protein sequence of GLP1(A8G/G22E/R36G)-Fn8-COL15NC1 was listed as SEQ ID NO:18. The expression and purification protocol of the fusion protein GLP1(A8G/G22E/R36G)-Fn8-COL15NC1 was the same as described in example 3.

```
                                        SEQ ID NO: 18
GLP-1(A8G/G22E/R36G)-Fn8-p246-COL15NC1 protein
sequence, the sequence of COL15NC1 is underlined.
The GLP-1 mutation sites (A8G/G22E/R36G) are in
Italic,.
HGEGTFTSDVSSYLEEQAAKEFIAWLVKGGGSGGGSGGGSGGGSGGGSGS

GGAVPPPTDLRFTNIGPDTMRVTWAPPPSIDLTNELVRYSPVKNEEDVAE

LSISPSDNAVVLTNLLPGTEYVVSVSSVYEQHESTPLRGRQKTGGGGSGG

GSGSGSESGSGGGSTSSGTGSETESPGSGSESGSGPSSAGSGSGSESGSG

SGSSGPGSTGGSGSESGSGPGSSGTGGTATGSGSESGSGPGSSGPGSTGS

GSGSESGSGSGSSGTGSTGGSGSESGSGPGSPRPGSTGTGSGSESGSGPG

SSERGSAGGSGSESGSGTSESSASGSTGGSGSESGSGSESGSGSGSESGS

GPESPGSGGSGSESGSGTSGSTGSGSESGSGGGSGGGSGG

NLVTAFSNMDDMLQKAHLVIEGTFIYLRDSTEFFIRVRDGWKKLQLGELI

PIPA
```

Example 10: Cloning and Expression of GLP-1(A8G/G22E/R36G) Fused with Fn8, pCloud Sequence and Human Collagen XIX NC2 Domain (COL19NC2)

In this example, we demonstrated that the NC2 domain from collagen XIX can be utilized as the scaffold protein in our method. It has been shown that human collagen XIX NC2 domain (COL19NC2) forms a highly stable homo-trimer [28]. To generate the expression vector encoding the fusion protein of GLP1(A8G/G22E/R36G)-Fn8-p246-COL19NC2, the gene encoding pCloud sequence p246 and COL19NC2 domain was synthesized, digested by BamHI and XhoI and ligated into the digested pET29b-GLP-1(A8G/G22E/R36G)-Fn8-p246-COL15NC1 vector generated before. The resulted vector was named as pET29b-GLP1(A8G/G22E/R36G)-Fn8-p246-COL19NC2 and the sequence of the vector was confirmed by DNA sequencing. The protein sequence of GLP1(A8G/G22E/R36G)-Fn8-p246-COL19NC2 was listed as SEQ ID NO:19. The expression and purification protocol of the fusion protein GLP1(A8G/G22E/R36G)-Fn8-p246-COL19NC2 was the same as described in example 3.

```
                                        SEQ ID NO: 19
GLP-1(A8G/G22E/R36G)-Fn8-p246-COL19NC2 protein
sequence, the sequence of COL19NC2 is underlined.
The GLP-1 mutation sites (A8G/G22E/R36G) are in
Italic,.
HGEGTFTSDVSSYLEEQAAKEFIAWLVKGGGSGGGSGGGSGGGSGGGSGS

GGAVPPPTDLRFTNIGPDTMRVTWAPPPSIDLTNFLVRYSPVKNEEDVAE

LSISPSDNAVVLTNLLPGTEYVVSVSSVYEQHESTPLRGRQKTGGGGSGG

GSGSGSESGSGGGSTSSGTGSETESPGSGSESGSGPSSAGSGSGSESGSG

SGSSGPGSTGGSGSESGSGPGSSGTGGTATGSGSESGSGPGSSGPGSTGS

GSGSESGSGSGSSGTGSTGGSGSESGSGPGSPRPGSTGTGSGSESGSGPG

SSERGSAGGSGSESGSGTSESSASGSTGGSGSESGSGSESGSGSGSESGS

GPESPGSGGSGSESGSGTSGSTGSGSESGSGGGSGGGSGG

GIPADAVSFEEIKKYINQEVLRIFEERMAVFLSQLKLPAAMLAAQAYGRP
```

Example 11: Cloning and Expression of GLP-1(A8G/G22E/R36G) Fused with Fn8, pCloud Sequence and Human ACRP30 C-Terminal C1q-Like Domain ACRP30 (also referred to as Adiponectin, GBP-28, apM1 and AdipoQ) is a protein hormone that modulates a number of metabolic processes, including glucose regulation and fatty acid catabolism [49]. ACRP30 contains a C-terminal globular domain that forms a homo-trimer with typical C1q-like structure [50]. In this example, we demonstrated that the C1q-like domain, such as the ACRP30 C1q-like domain, can be utilized as the scaffold protein in our method. To generate the expression vector encoding the fusion protein of GLP1(A8G/G22E/R36G)-Fn8-p246-ACRP30 C1q-like domain, the gene encoding pCloud sequence p246 and ACRP30 C1q-like domain was synthesized, digested by BamHI and XhoHI and ligated into the digested pET29b-GLP-1(A8G/G22E/R36G)-Fn8-p246-COL15NC1 vector generated before. The resulted vector was named as pET29b-GLP1(A8G/G22E/R36G)-Fn8-p246-ACRP30 and the sequence of the vector was confirmed by DNA sequencing. The protein sequence of GLP1(A8G/G22E/R36G)-Fn8-p246-ACRP30 was listed as SEQ ID NO:20.

```
                                     SEQ ID NO: 20
GLP1(A8G/G22E/R36G)-Fn8-p246-ACRP30 protein
sequence, the sequence of ACRP30 C1q-like domain
is underlined. The GLP-1 mutation sites (A8G/G22E/
R36G) are in Italic,.
HGEGTFTSDVSSYLEEQAAKEFIAWLVKGGGSGGGSGGGSGGGSGGGSGS

GGAVPPPTDLRFTNIGPDTMRVTWAPPPSIDLTNFLVRYSPVKNEEDVAE

LSISPSDNAVVLTNLLPGTEYVVSVSSVYEQHESTPLRGRQKTGGGGSGG

GSGSGSESGSGGGSTSSGTGSETESPGSGSESGSGPSSAGSGSGSESGSG

SGSSGPGSTGGSGSESGSGPGSSGTGGTATGSGSESGSGPGSSGPGSTGS

GSGSESGSGSGSSGTGSTGGSGSESGSGPGSPRPGSTGTGSGSESGSGPG

SSERGSAGGSGSESGSGTSESSASGSTGGSGSESGSGSESGSGSGSESGS

GPESPGSGGSGSESGSGTSGSTGSGSESGSGGGSGGGSGG

VYRSAFSVGLETRVTVENVEIRFTKIFYNQQNHYDGSTGKFYCNIPGLYY

FSYHITVYMKDVKV

SLFKKDKAVLFTYDQYQEKNVDQASGSVLLHLEVGDQVWLQVYGDGDHNG

LYADNVNDSTFTGFLLY

HDTN
```

Example 12: Constructions of the Fusion Proteins of GLP-1(A8G/G22E/R36G), Fn8, pCloud Sequences with Various Lengths and COL18NC1

Numerous pCloud sequences can be generated by use of the human Fribrinogen fragments listed in Table 1 and the flexible loops listed in Table 2. In the pCloud sequences, the fibrinogen fragments are flanked by flexible loops. In this example, we generated three pCloud sequences p245, p271 and p285 using the described method. In the pCloud sequences of p245 and p2'71, the 12 human fibrinogen alpha chain fragments listed in Table 1 were connected in the order as they appear in the human fibrinogen alpha chain sequence to constitute the pCloud sequences. In the case of p285, the fragments listed in Table 1 were connected in the order that is distinct from they appear in the human fibrinogen alpha chain sequence to generate the pCloud sequence. In p285, some fibrinogen alpha chain fragments were utilized more than once. To construct p245, the flexible loops GGGSGGGSGS (SEQ ID NO:87), GSGSESTSG (SEQ ID NO:68), GSTSESGSG (SEQ ID NO:63), GSTSGSESG (SEQ ID NO:64), GSESGSTSG (SEQ ID NO:66), GSESTSGSG (SEQ ID NO:65), GSGSTSESG (SEQ ID NO:67) and GGSGGGSGG (SEQ ID NO:75) listed in Table 2 were utilized to connect the human fribrinogen alpha chain fragments. To construct p271, the flexible loops GGGSGGGS (SEQ ID NO:86), GGSGGGSGG (SEQ ID NO:75) and GGSGSESGSGG (SEQ ID NO:74) were utilized to connect the human fibrinogen alpha chain fragments. To construct p285, the flexible loops GGGSGGGS (SEQ ID NO:86), GGSGGGSGG (SEQ ID NO:75) and GSGSESGSG (SEQ ID NO:69) were utilized to connect the fibrinogen alpha chain fragments.

The genes encoding pCloud sequence (p245, p271 and p285, respectively) and the scaffold protein COL18NC1 was synthesized, digested by BamHI and XhoI and ligated into the digested vector pET29b-GLP-1(A8G/G22E/R36G)-Fn8-p246-COL18NC1 generated before. The resulted vector were named as pET29b-GLP-1(A8G/G22E/R36G)-Fn8-p245-COL18NC1, pET29b-GLP-1(A8G/G22E/R36G)-Fn8-p271-COL18NC1 and pET29b-GLP-1(A8G/G22E/R36G)-Fn8-p285-COL18NC1. The resulted fusion proteins were named as GLP-1(A8G/G22E/R36G)-Fn8-p245-COL18NC1, GLP-1(A8G/G22E/R36G)-Fn8-p271-COL18NC1 and GLP-1(A8G/G22E/R36G)-Fn8-p285-COL18NC1, respectively. The protein sequences of these fusion proteins were listed as SEQ ID NO:21-23. These fusion proteins were expressed and purified using the protocols described in example 3.

```
                                     SEQ ID NO: 21
GLP-1(A8G/G22E/R36G)-Fn8-p245-COL18NC1 protein
sequence, the GLP-1 mutation sites (A8G/G22E/R36G)
are in Italic and bold. The flexible loop between
GLP1(A8G/G22E/R36G) and Fn8 is in bold. The pCloud
sequence p245 is underlined,.
HGEGTFTSDVSSYLEEQAAKEFIAWLVKGGGSGGGSGGGSGGGSG

GGSGSGGAVPPPTDLRFTNIGPDTMRVTWAPPPSIDLTNELVRYSPVKNE

EDVAELSISPSDNAVVLTNLLPGTEYVVSVSSVYEQHESTPLRGRQKTG

GGGSGGGSGSGSTSESGGSTSSGTGSETESPGSGSESTSGPSSAGSGSTS

ESGSGSGSSGPGSTGGSTGGSESGPGSSGTGGTATGSESGSTSGPGSSGP

GSTGSGSTSESGSGSGSSGTGSTGGSESGSTSGPGSPRPGSTGTGSTSGS

ESGPGSSERGSAGGSESTSGSGTSESSASGSTGGSTSGSESGSESGSGST

SESGSGPESPGSGGSGSTSESGTSGSTGSESTSGSGGGSGGGSGG

GASSGVRLWATRQAMLGQVHEVPEGWLIEVAEQEELYVRVQNGFRKVQLE

ARTPLPRG
```

```
                                     SEQ ID NO: 22
GLP-1(A8G/G22E/R36G)-Fn8-p271-COL18NC1 protein
sequence, the GLP-1 mutation sites (A8G/G22E/R36G)
are in Italic and bold. The flexible loop between
GLP1(A8G/G22E/R36G) and Fn8 is in bold. The pCloud
sequence p271 is underlined,.
HGEGTFTSDVSSYLEEQAAKEFIAWLVKGGGSGGGSGGGSGGGSG

GGSGSGGAVPPPTDLRFTNIGPDTMRVTWAPPPSIDLTNFLVRYSPVKNE

EDVAELSISPSDNAVVLTNLLPGTEYVVSVSSVYEQHESTPLRGRQKTG

GGGSGGGSGGSGSESGSGGGSTSSGTGSETESPGGSG

SESGSGGPSSAGSGGSGSESGSGGSGSSGPGSTGGGSGSESGSGGPGSSG

TGGTATGSGSESGSGGPGSSGPGSTGSGGSGSESGSGGSSGTGSTGG

GSGSESGSGGPGSPRPGSTGTGGSGSESGSGGPGSSERGSAGGGSGSESG

SGGTSESSASGSTGGGSGSESGSGGSESGSGGSGSESGSGGPESPGSGGG

SGSESGSGGTSGSTGGSGSESGSGGGGSGGGSGG

GASSGVRLWATRQAMLGQVHEVPEGWLIFVAEQEELYVRVQNGFRKVQLE

ARTPLPRG
```

-continued

SEQ ID NO: 23
GLP-1(A8G/G22E/R36G)-Fn8-p285-COL18NC1 protein
sequence, the GLP-1 mutation sites (A8G/G22E/R36G)
are in Italic and bold. The flexible loop between
GLP1(A8G/G22E/R36G) and Fn8 is in bold. The pCloud
sequence p285 is underlined,.
HGEGTFTSDVSSYLEEQAAKEFIAWLVKGGGSGGGSGGGSGGGSG

GGSGSGGAVPPPTDLRFTNIGPDTMRVTWAPPPSIDLTNFLVRYSPVKNE

EDVAELSISPSDNAVVLTNLLPGTEYVVSVSSVYEQHESTPLRGRQKTG

GGGSGGGSGSGSESGSGGGSTSSGTGSETESPGSGSESGSGPSSAGSGSG

SESGSGSGSSGPGSTGGSGSESGSGPGSSGTGGTATGSGSESGSGPGSSG

PGSTGSGSGSESGSGSGSSGTGSTGGSGSESGSGPGSPRPGSTGTGSGSE

SGSGPGSSERGSAGGSGSESGSGTSESSASGSTGGSGSESGSGSESGSGS

GSESGSGPESPGSGGSGSESGSGTSGSTGSGSESGSGPGSSGPGSTGSGS

GSESGSGSGSSGTGSTGGSGSESGSGGGSGGGSGG

GASSGVRLWATRQAMLGQVHEVPEGWLIFVAEQEELYVRVQNGFRKVQLE

ARTPLPRG

Figure 5:
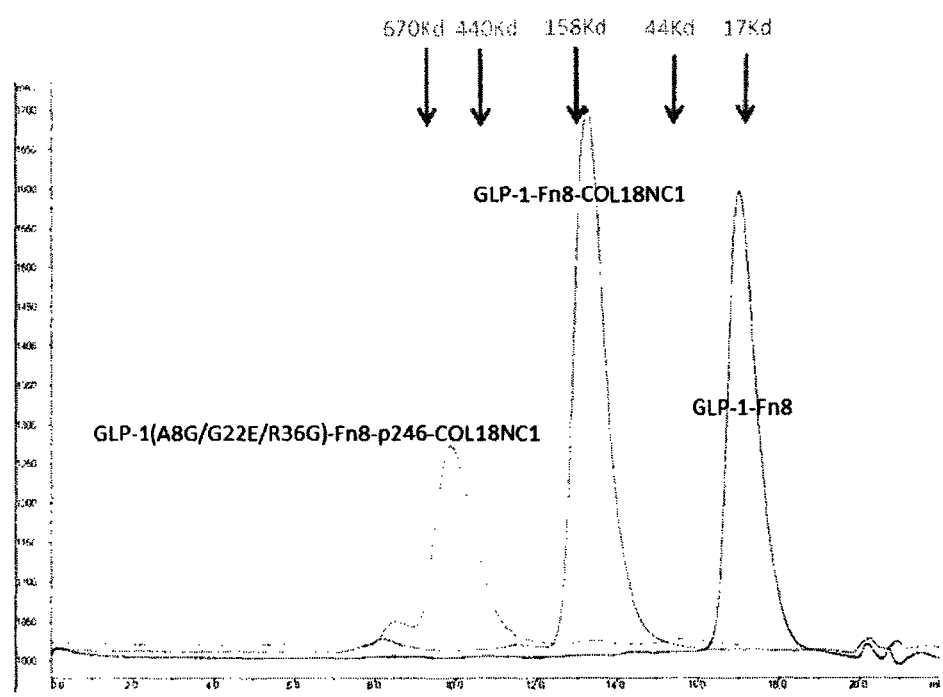
FIG. 5 shows the gel filtration chromatography profiles for purified GLP-1-Fn8, GLP-1-Fn8-COL18NC1, GLP-1 (A8G/G22E/R36G)-Fn8-p246-COL18NC1 by use of the analytical column Superdex200 (GE Healthcare). In this figure, the profiles of these proteins are labeled. The elution time for the molecular marker proteins are shown by arrows. The X-axis refers to elution time and the Y-axis refers to UV280 absorbance intensity, respectively.

Example 13. The Therapeutic Polypeptide Fused with pCloud Polypeptides and the Scaffold Protein Exhibits a Much Larger Hydrodynamic Radius and/or Rg for its Molecular Weight In this example, we presented data to demonstrate that connecting the therapeutic polypeptide with the unstructured pCloud polypeptide and the trimeric scaffold protein can render the therapeutic polypeptide a much larger hydrodynamic radius and/or Rg compared with that for a tightly folded protein with the same molecular weight. The apparent molecular weights of the fusion proteins were estimated by use of an analytical gel filtration column Superdex-200 (GE Healthcare) mounted on the AKTA FPLC system (GE Healthcare). The purified fusion proteins GLP-1-Fn8, GLP-1-Fn8-COL18NC1, GLP-1(A8G/G22E/R36G)-Fn8-p246-COL18NC1 were loaded on the Superdex200 column. GLP-1-Fn8 is a fusion protein of GLP-1 and Fn8 and contains the first 144 amino acid residues of the fusion protein GLP-1-Fn8-COL18NC1 (SEQ ID NO:2). GLP-1-Fn8 does not contain the scaffold protein COL18NC1, so it forms a monomer in solution. FIG. 5 showed the chromatography profiles for these fusion proteins. The apparent molecular weights for GLP-1-Fn8, GLP-1-Fn8-COL18NC1, GLP-1(A8G/G22E/R36G)-Fn8-p246-COL18NC1 showed by gel filtration analysis were ~20Kd, ~100Kd and ~550Kd, respectively. The genuine molecular weights for the fusion proteins GLP-1-Fn8 monomer, GLP-1-Fn8-COL18NC1 trimer, and GLP-1(A8G/G22E/R36G)-Fn8-p246-COL18NC1 trimer were ~15 Kd, 65 Kd and 123Kd, respectively. The data clearly showed that the trimer formation caused by the scaffold protein COL18NC1 domain provided GLP-1-Fn8-COL18NC1 a larger apparent molecular weight compared with its genuine molecular weight (100 Kd vs 65 Kd). More importantly, the data further indicated that including the unstructured pCloud polypeptide into the fusion protein GLP-1(A8G/G22E/R36G)-Fn8-p246-COL18NC1 dramatically enlarged the apparent molecular weight of the fusion protein compared with its genuine molecular weight (550 Kd vs 123 Kd). Therefore, our "Trident Technology" method could provide the therapeutic polypeptide with a large hydrodynamic radius which exhibited the increased apparent molecular size as shown by gel filtration profile for the extended in vivo half life.

Example 14. cAMP Assay for Measuring GLP-1 Activity

Figure 6:
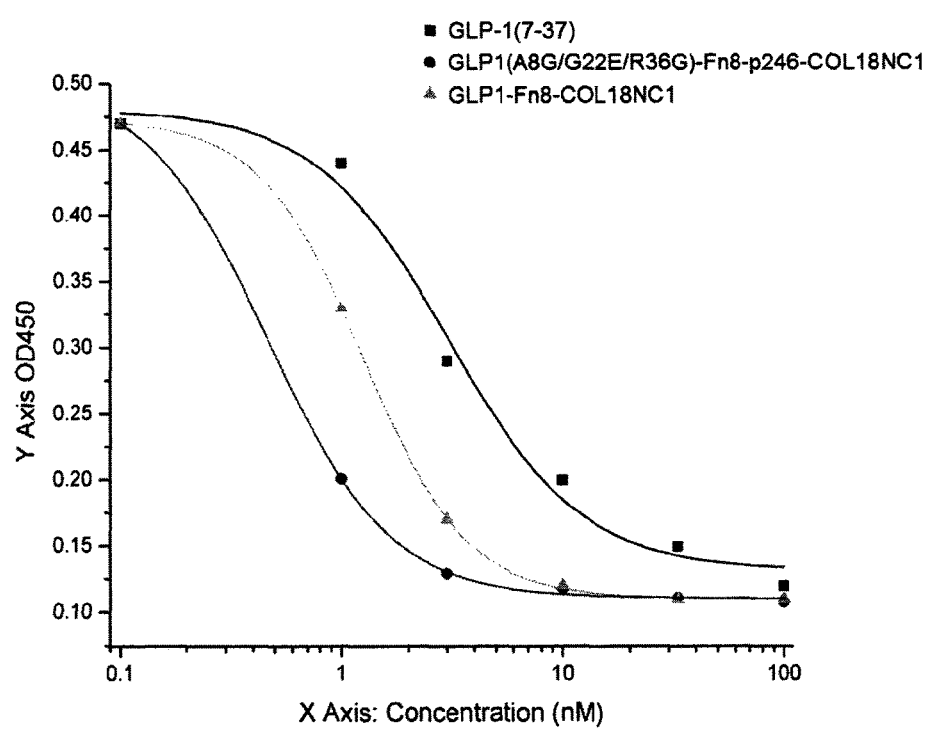
FIG. 6 shows the results of cAMP assays for GLP-1 (7-37) peptide, GLP-1-Fn8-COL18NC1 and GLP1(A8G/G22E/R36G)-Fn8-p246-COL18NC1. This assay is based on competitive binding technique. A monoclonal antibody specific for cAMP becomes bound to the goat anti-mouse antibody coated onto the microplate. Following a wash to remove excess monoclonal antibody, cAMP present in a sample competes with a fixed amount of horseradish peroxidase (HRP)-labeled cAMP for sites on the monoclonal antibody. This is followed by another wash to remove excess conjugate and unbound sample. A substrate solution is added to the wells to determine the bound enzyme activity. The color development is stopped and the absorbance is read at 450_nm. The intensity of the color is inversely proportional to the concentration of cAMP in the sample. The Y-axis refers to the $OD_{450}$ obtained by the plate reader and the X-axis refers to the concentration of GLP-1 (7-37) peptide, GLP-1-Fn8-COL18NC1 and GLP1 (A8G/G22E/R36G)-Fn8-p246-COL18NC1.

Through binding and activating a specific G protein-coupled receptor (GLP-1 receptor), GLP-1 stimulates the signaling pathway to increase cAMP level in cells. Therefore, measuring the cytoplasmic cAMP level can be an accurate method to evaluate the biological activity of GLP-1. Chinese Hamster Ovary (CHO) cells stably transfected with human GLP-1 receptor (GLP-1R) were generated and named as S—CHO cells. S—CHO cells were propagated in DMEM medium with 10% FCS containing 0.05_mg/ml G418. Before analysis, SCHO cells were grown to 70-80% confluence in 6-well plates at 37° C. The cells were treated 0.2 mM 3-isobutyl-1-methylxanthine (IBMX). Cells were incubated with GLP-1 fusion proteins at various concentrations of 1 nM, 3 nM, 10 nM, 33 nM, 100 nM for 15 min at 37° C. The cells were then lysed by use of cold lysis buffer. The supernatants of the cell extracts were used for cAMP level determinations. The Parameter cAMP ELISA kit from R&D Systems was utilized to measure the cAMP concentrations in the cell lysates. The EC50 values of the GLP-1 fusion proteins were generated by using the software Origin. The GLP-1 (7-37) peptide (Anaspec) and BSA were used as positive and negative controls. FIG. 6 showed the results of cAMP assays for GLP1 (7-37) peptide and some other GLP-1 fusion proteins. The EC50 values of a number of GLP-1 containing fusion proteins are listed in Table 4. The data indicated that the fusion of GLP1 with the flexible unstructured polypeptide and the scaffold protein did not affect GLP-1 activity. As a matter of fact, if the lengths of flexible unstructured linker sequences are increased, the activities of fusion protein improved. We reasoned that a longer flexible, unstructured linker and/or the pCloud polypeptide may provide the GLP-1 peptide with more freedom to interact with the GLP-1 receptor.

TABLE 4

The activities of GLP-1 and GLP-1 containing fusion proteins measured by cAMP assay

| Proteins | EC50 (nM) measured by cAMP assay |
|---|---|
| GLP-1(7-37) peptide | 3.8 |
| GLP-1-Fn7-COL18NC1 | 2.2 |
| GLP-1-Fn8-COL18NC1 | 2.1 |
| GLP1(A8G/G22E)-Fn8-COL18NC1 | 1.3 |
| GLP1(A8V/G22E)-Fn8-COL18NC1 | 1.3 |
| GLP1(A8S/G22E)-Fn8-COL18NC1 | 1.3 |
| GLP1(A8G/G22E/R36S)-Fn8-COL18NC1 | 1.3 |
| GLP1(A8G/G22E/R36G)-Fn8-COL18NC1 | 1.2 |
| GLP1(A8G/G22E/R36S)-Fn8-COL15NC1-20 | 1.4 |
| GLP1(A8G/G22E/R36S)-Fn8-COL15NC1-30 | 1.3 |
| GLP1(A8G/G22E/R36S)-Fn8-COL15NC1-54 | 0.5 |
| GLP1(A8G/G22E/R36S)-Fn8-COL15NC1-60 | 0.5 |
| GLP1(A8G/G22E)-Fn8-p246-COL18NC1 | 0.5 |
| GLP1(A8V/G22E)-Fn8-p246-COL18NC1 | 0.5 |
| GLP1(A8S/G22E)-Fn8-p246-COL18NC1 | 0.6 |
| GLP1(A8G/G22E/R36S)-Fn8-p246-COL18NC1 | 0.4 |
| GLP1(A8G/G22E/R36G)-Fn8-p246-COL18NC1 | 0.4 |
| GLP1(A8G/G22E/R36G)-TNCfn3-p246-COL18NC1 | 0.5 |
| GLP1(A8G/G22E/R36G)-Fn8-p246-COL15NC1 | 0.5 |
| GLP1(A8G/G22E/R36G)-Fn8-p246-COL19NC2 | 0.6 |
| GLP1(A8G/G22E/R36G)-Fn8-p246-ACRP30 | 0.6 |
| GLP1(A8G/G22E/R36G)-Fn8-p245-COL18NC1 | 0.5 |

TABLE 4-continued

The activities of GLP-1 and GLP-1 containing fusion proteins measured by cAMP assay

| Proteins | EC50 (nM) measured by cAMP assay |
|---|---|
| GLP1(A8G/G22E/R36G)-Fn8-p271-COL18NC1 | 0.4 |
| GLP1(A8G/G22E/R36G)-Fn8-p285-COL18NC1 | 0.4 |

Example 15: The Pharmacokinetics Studies for GLP-1-Fn8-COL18NC1, GLP1(A8G/G22E/R36G)-Fn8-p246-COL18NC1 and GLP1(A8G/G22E/R36G)-Fn8-p285-COL18NC1

To evaluate the pharmacokinetics profiles for the GLP-1 containing fusion proteins generated using the method of the invention, we purified the recombinant fusion proteins of GLP-1-Fn8-COL18NC1, GLP1(A8G/G22E/R36G)-Fn8-p246-COL18NC1 and GLP1(A8G/G22E/R36G)-Fn8-p285-COL18NC1 in PBS buffer, pH 7.2. These fusion proteins were administered into SD (Sprague-Dawley) rats by intraperitoneal injections at the dose of 5 nmol/kg for animals, respectively. Blood samples were taken at various time points after injections such as 0-min, 30-min, 1-hour, 2-hour, 4-hour, 6-hour, 8-hour, 24-hour, 48-hour, 3-day, 4-day, 5-day, 6-day and 7-day. The serum samples were centrifuged and kept at −80° C. freezer.

The GLP-1 concentrations within the samples were examined by use of the sandwich ELISA method. The rabbit polyclonal antibody against human Fibronectin at the concentration of 3 ug/ml (Ab299, Abcam company) was coated on ELISA plate for 1 hour at room temperature. Then the plate was washed by PBST buffer three times and the wells were blocked by PBS with 10% FBS for 1 hour at room temperature. The plate was washed three times before the serum samples containing GLP-1 fusion proteins were added. The serum samples could be diluted to 20-10000 folds before use. The ELISA plate was incubated with the serum samples at room temperature for 1 hour and then washed by PBST buffer five times. Then mouse monoclonal against human GLP-1 peptide antibody (sc57510, Santa Cruz Biotechnology) at the concentration of 1 ug/ml in PBST buffer was added to the wells. The plate was washed extensively after incubation of 1 hour at room temperature. The secondary antibody, Goat anti-rabbit IgG HRP conjugated antibody (Beijing ZSGB-Bio company, ZB 5301), was added into the wells and the color was developed using TMB (3,3',5,5'-tetramethylbenzidine, BD Biosciences, Cat 555214). The plate reader (Bio-Rad microplate reader Model 680) was utilized to obtain the OD450 readings. This method has been calibrated using purified proteins first.

Figure 7:
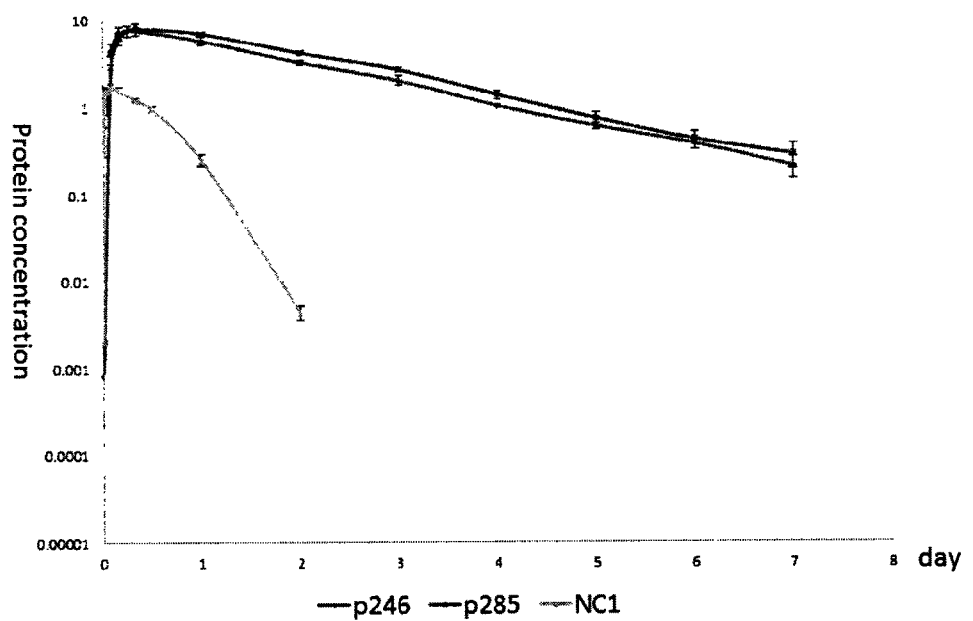
FIG. 7 shows the pharmacokinetics profiles of the fusion proteins GLP-1-Fn8-COL18NC1, GLP-1 (A8G/G22E/R36G)-Fn8-p246-COL18NC1, and GLP-1(A8G/G22E/R36G)-Fn8-p285-COL18NC1 in Sprague Dawley rats. The protein concentration in the blood samples were measured by use of the sandwich ELISA method. In this figure, the profiles of these proteins are labeled as NC1, p246 and p285, respectively. The errors bars calculated from a group of six rats are labeled.

FIG. 7 showed the pharmacokinetics profiles of the GLP-1 containing proteins in SD rats by use of the sandwich ELISA method described above. The pharmacokinetics parameters were obtained by using the WinNonlin software (Table 5). The data clearly showed that the GLP-1 containing fusion proteins generated by use of the method of the invention exhibited much extended in vivo half life possibly due to their enlarged hydrodynamic radius and/or Rg. Particularly, including the pCloud polypeptide into the fusion protein dramatically improved the pharmacokinetic profile of fusion protein. The half life of GLP-1-Fn8-COL18NC1 reached 5.3 hours compared with the half life of a couple of minutes for GLP-1 peptide. The half life of GLP1(A8G/G22E/R36G)-Fn8-p246-COL18NC1 and GLP1(A8G/G22E/R36G)-Fn8-p285-COL18NC1 were further extended to 30.8 and 31.2 hours, respectively, due to the applications of the flexible unstructured pCloud sequences within the fusion proteins.

The toxicity of GLP1(A8G/G22E/R36G)-Fn8-p246-COL18NC1 in SD rats was also examined. A single dose of 30 nmol/kg and repeated doses of 5 nmol/kg every three days for four weeks did not induce unacceptable adverse effects such as significant weight loss and fever in rats.

Figure 8:
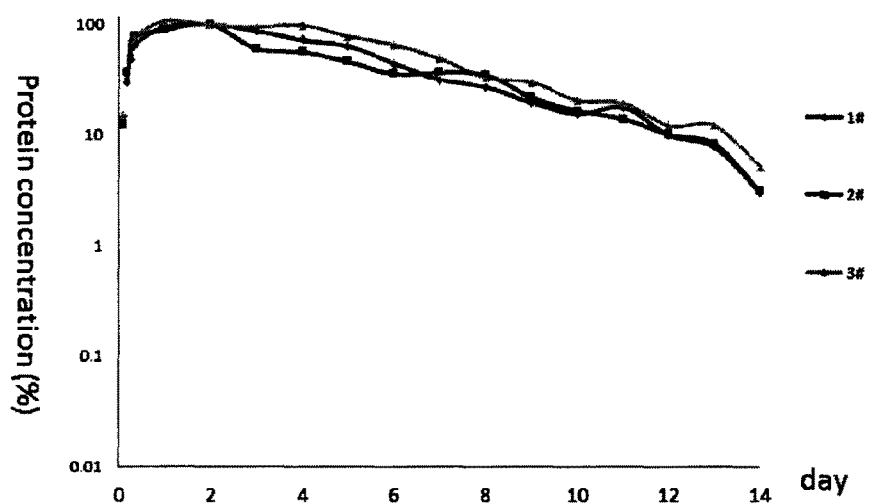
FIG. 8 shows the pharmacokinetics profiles of the fusion proteins GLP-1(A8G/G22E/R36G)-Fn8-p246-COL18NC1 in three cynomolgus monkeys. The protein concentration in the serum samples were measured by use of the sandwich ELISA method. In this figure, the three cynomolgus monkeys were labeled as #1, 2 and 3, respectively.

To further investigate the pharmacokinetics profiles for the GLP-1 containing fusion proteins generated using the method of the invention, the fusion protein GLP1(A8G/G22E/R36G)-Fn8-p246-COL18NC1 was administrated into the cynomolgus monkeys by subcutaneous injection. The fusion protein was administered on three cynomolgus monkeys at the dose of 5 nmol/kg. Blood samples were taken at various time points after injections such as 0-min, 2-hour, 4-hour, 6-hour, 8-hour, 24-hour, 48-hour, and daily until the 15th day. The serum samples were centrifuged and kept at −80° C. freezer. The concentrations of the fusion protein within the serum samples were examined by using the sandwich ELISA method described above. The pharmacokinetics profile of the fusion protein GLP1(A8G/G22E/R36G)-Fn8-p246-COL18NC1 in cynomolgus monkeys was shown in FIG. 8. The pharmacokinetics parameters were obtained by using the WinNonlin software (Table 5). The half life of the fusion protein GLP1(A8G/G22E/R36G)-Fn8-p246-COL18NC1 in cynomolgus monkeys was estimated to be ~67 hours, which is significantly longer than the half life of GLP-1-Fc fusion protein (half life ~51 hours) in monkeys_[6]. The pharmacokinetics data in rats and monkeys strongly suggested that a weekly dose or even once every ten day of GLP1(A8G/G22E/R36G)-Fn8-p246-COL18NC1 in human may be effective.

The serum samples of the cynomolgus monkeys receiving the fusion protein GLP1(A8G/G22E/R36G)-Fn8-p246-COL18NC1 were withdrawn one month after dosing to examine whether specific antibody against GLP1(A8G/G22E/R36G)-Fn8-p246-COL18NC1 has been generated. The analysis of the serum samples of the three monkeys receiving the fusion protein by use of ELISA method indicated that no specific antibody was induced against GLP1(A8G/G22E/R36G)-Fn8-p246-COL18NC1 in any of the cynomolgus monkeys.

TABLE 5

Pharmacokinetics parameters for the GLP-1 containing fusion proteins in Sprague-Dawley rats and cynomolgus monkeys. In the table, the fusion protein GLP-1-Fn8-COL18NC1, GLP1(A8G/G22E/R36G)-Fn8-p246-COL18NC1 and GLP1(A8G/G22E/R36G)-Fn8-p285-COL18NC1 were shown in abbreviations as NC1, p246-NC1 and p285-NC1.

| | | NC1 | p246-NC1 | p285-NC1 | P246-NC1 |
|---|---|---|---|---|---|
| Species | | Rats | Rats | Rats | Monkey |
| T½ | hour | 5.32 | 30.8 | 31.2 | 67.3 |
| Cmax | ug/ml | 1.96 | 5.73 | 7.98 | 8.21 |
| AUCall | ug * h/ml | 25.8 | 301.2 | 475.3 | 1267.8 |
| Vss | ml/kg | 518.64 | 90.23 | 62.0 | 51.6 |
| CL/F | ml/h/kg | 77.6 | 2.03 | 1.37 | 0.48 |

Figure 9A:
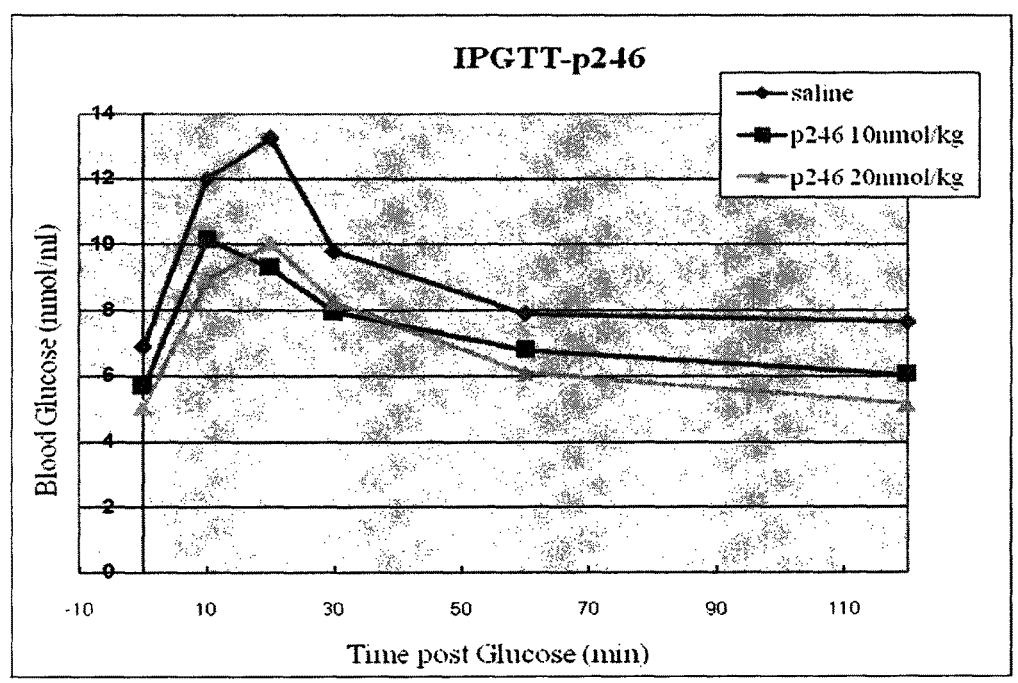
In FIG. 9a, the rats were injected with saline, GLP1(A8G/G22E/R36G)-Fn8-p246-COL18NC1 at the dose of 10_nmol/kg and 20_nmol/kg, respectively. 8 hours after the administrations of the fusion protein (and control), the IPGTT experiments were conducted. The three curves indicated the glucose levels in the IPGTT for rats that received negative control (saline), GLP1(A8G/G22E/R36G)-Fn8-p246-COL18NC1 at the doses of 10_nmol/kg and 20_nmol/kg, respectively.
Figure 9B:
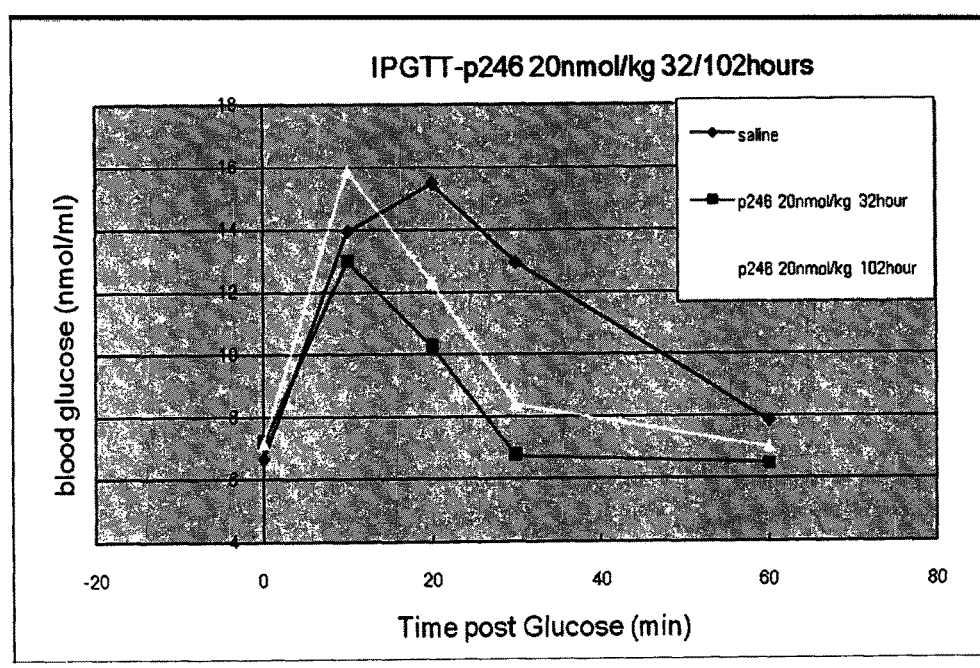
In FIG. 9b, the rats were injected with saline, GLP1(A8G/G22E/R36G)-Fn8-p246-COL18NC1 at the dose of 20 nmol/kg. 32 hours and 102 hours after the administrations of the fusion protein (and the control), the IPGTT experiments were conducted. The three curves indicated the glucose levels in the IPGTT for rats that 32 hours and 102 hours after administration of negative control (saline), GLP1(A8G/G22E/R36G)-Fn8-p246-COL18NC1 respectively.

Example 16: The Intraperitoneal Glucose Tolerance Test (IPGTT) of GLP1(A8G/G22E/R36G)-Fn8-p246-COL18NC1 in SD Rats To evaluate the efficacy of GLP1(A8G/G22E/R36G)-Fn8-p246-COL18NC1 to reduce the glucose level in animal models, we performed the Intraperitoneal glucose tolerance test (IPGTT) in SD rats. The fusion protein GLP1(A8G/G22E/R36G)-Fn8-p246-COL18NC1 was administered on SD (Sprague-Dawley) rats by intraperitoneal injections at the dose of 10 nmol/kg and 20 nmol/kg for animals, respectively. Glucose was injected into the animals with the dose of 2 g/kg at 8 hours, 32 hours and 100 hours after the injection of the fusion protein GLP1(A8G/G22E/R36G)-Fn8-p246-COL18NC1. Blood samples were taken at various time points after injections such as 0-min, 10-min, 20-min, 30-min, 60-min and 120-min. The glucose levels within the blood samples were measured using a Accu-Chek Performa blood glucose meter (Roche) immediately. In FIG. 9a, the rats were injected with GLP1(A8G/G22E/R36G)-Fn8-p246-COL18NC1 at the dose of 10 nmol/kg and 20 nmol/kg about 8 hours before the IPGTT experiments were conducted. The data showed in FIG. 9a indicated that the fusion protein GLP1(A8G/G22E/R36G)-Fn8-p246-COL18NC1 at the dose of 10 nmol/kg and 20 nmol/kg can efficiently reduce the glucose level. In FIG. 9b, about 32 hours and 100 hours after the rats were injected with GLP1(A8G/G22E/R36G)-Fn8-p246-COL18NC1 at the dose of 20 nmol/kg, the IPGTT experiments were conducted. The data in FIG. 9b clearly showed that a single dose of GLP1(A8G/G22E/R36G)-Fn8-p246-COL18NC1 can maintain its glucose-reducing activity in vivo for an extended period of time. Even at 100 hours after the injection of the fusion protein GLP1(A8G/G22E/R36G)-Fn8-p246-COL18NC1 into the animals, the fusion protein can still reduce the glucose level significantly. The IPGTT experiments in rats strongly suggested that the fusion protein GLP1(A8G/G22E/R36G)-Fn8-p246-COL18NC1 can be utilized as a long acting GLP-1 analogue to treat diabetes.

Example 17: Construction of the Fusion Protein of Interferon, pCloud Polypeptide and the Scaffold Protein COL18NC1

In this example, we demonstrate that Interferon can be fused with the pCloud polypeptide and the scaffold protein to increase the in vivo half life of Interferon. The gene encoding human Interferon alpha-2b was synthesized, digested by NdeI and BamHI and ligated into the digested vectors pET29b-GLP-1(A8G/G22E/R36G)-Fn8-p246-COL18NC1 and pET29b-GLP-1(A8G/G22E/R36G)-Fn8-p271-COL18NC1 generated before. The resultant fusion protein was named as IFN-p246-COL18NC1 and IFN-p271-COL18NC1, respectively. The protein sequences of these fusion proteins were listed as SEQ ID NO:24 and 25. The Interferon containing fusion proteins were expressed by use of the Pichia expression system (Life Technologies). The genes encoding IFN-p246-COL18NC1 and IFN-p271-COL18NC1 were amplified by PCR and cloned into the expression vector pPICZalphaA_(Life Technologies) by use of XhoI and NotI. The protein expression was carried out by following the protocols from Life Technologies. The secreted recombinant proteins were purified using the similar protocol described in example 3. Alternatively, the fusion protein IFN-p246-COL18NC1 and IFN-p271-COL18NC1 can be expressed by use of the E. coli expression system as described in example 3.

To measure the biological activity of the fusion protein IFN-p246-COL18NC1 and IFN-p271-COL18NC1 to activate the JAK/STAT pathway, the Cignal ISRE Luciferase Reporter Assay Kit (Qiagen) was utilized. Hela cells were transfected with vector that contains the interferon stimulated response element (ISRE) reporter. After 16 hours of transfection, medium was changed to assay medium (Opti-MEM+10% heat inactivated FBS+0.1 mM NEAA+1 mM Sodium pyruvate+100 U/ml penicillin+100 µg/ml streptomycin). After 24 hours of transfection, cells were treated with IFN-p246-COL18NC1 and IFN-p271-COL18NC1 fusion proteins at various concentrations for 18 hours. Dual Luciferase assay was performed, and promoter activity values are expressed as arbitrary units using a Renilla reporter for internal normalization. The activity of commercially available Interferon alpha-2b was measured as 2.20×$10^5$ IU/ug and the activities of IFN-p246-COL18NC1 and IFN-p271-COL18NC1 were measured as 1.85×$10^5$ IU/ug and 1.72×$10^5$ IU/ug. The data clearly showed that fusing with pCloud sequence and the scaffold protein did not diminish the biological activity of Interferon alpha 2b.

SEQ ID NO: 24
protein sequence of IFN-p246-COL18NC1, The pCloud sequence p246 is underlined,.
CDLPQTHSLGSRRTLMLLAQMRRISLFSCLKDRHDEGFPQEEFGNQFQKA

ETIPVLHEMIQQIFNLFSTKDSSAAWDETLLDKFYTELYQQLNDLEACVI

QGVGVTETPLMNEDSILAVRKYFQRITLYLKEKKYSPCAWEVVRAEIMRS

FSLSTNLQESLRSKE

GGGSGGGSGSGSESGSGGGSTSSGTGSETESPGSG

SESGSGPSSAGSGSGSESGSGSGSSGPGSTGGSGSESGSGPGSSGTGGTA

TGSGSESGSGPGSSGPGSTGSGSGSESGSGSGSSGTGSTGGSGSESGSGP

GSPRPGSTGTGSGSESGSGPGSSERGSAGGSGSESGSGTSESSASGSTGG

SGSESGSGSESGSGSGSESGSGPESPGSGGGSGSESGSGTSGSTGSGSESG

SGGGSGGGSGGGASSGVRLWATRQAMLGQVHEVPEGWLIFVAEQEELYVR

VQNGFRKVQLEARTPLPRG

SEQ ID NO: 25
protein sequence of IFN-p271-COL18NC1, The pCloud sequence p271 is underlined,.
CDLPQTHSLGSRRTLMLLAQMRRISLFSCLKDRHDFGFPQEEFGNQFQKA

ETIPVLHEMIQQIFNLFSTKDSSAAWDETLLDKFYTELYQQLNDLEACVI

QGVGVTETPLMNEDSILAVRKYFQRITLYLKEKKYSPCAWEVVRAEIMRS

FSLSTNLQESLRSKE

GGGSGGGSGGSGSESGSGGGSTSSGTGSETESPGGSG

SESGSGGPSSAGSGSGSESGSGSGSSGPGSTGGGSGSESGSGGPGSSG

TGGTATGGSGSESGSGPGSSGPGSTGSGGSGSESGSGGSGSSGTGSTGG

GSGSESGSGGPGSPRPGSTGTGGSGSESGSGGPGSSERGSAGGGSGSESG

SGGTSESSASGSTGGGSGSESGSGGSESGSGSGSESGSGGPESPGSGGG

SGSESGSGGTSGSTGGSGSESGSGGGSGGGSGG

-continued

GASSGVRLWATRQAMLGQVHEVPEGWLIFVAEQEELYVRVQNGFRKVQLE

ARTPLPRG

Example 18: Construction of the Fusion Protein of TNFR2, COL18NC1 and pCloud Polypeptide TNF Receptor (TNFR2, or p'75) has been fused to IgG1 Fc fragment to constitute a fusion protein Etanercept (Enbrel). Etanercept has been successfully utilized to treat severe active rheumatoid arthritis by blocking the TNF alpha functions [51]. In this example, we applied the method of the present invention on TNFR2 to generate the fusion protein of TNFR2, COL18NC1 and the pCloud polypeptide. In this example, the TNFR2 has been placed at the N-terminus of the scaffold protein COL18NC1 while the pCloud polypeptide has been positioned at the C-terminus of the scaffold protein COL18NC1. The rationale for this design is to make sure that three TNFR2 can properly interact with and block the function of the TNF alpha trimer simultaneously. The resultant TNFR2-COL18NC1-pCloud fusion protein is tri-valent and can block all three binding sites of TNFalpha while retaining a long half life in vivo. On the other hand, one Etanercept molecule can only block two out of three possible binding sites located on TNF alpha homo-trimer.

To construct the fusion protein, the optimized gene encoding TNFR2 was synthesized and cloned into the pPICZalphaA (Life Technologies) by XhoI and BamHI. The resultant vector is named as pPICZalphaA-TNFR2. The optimized gene encoding COL18NC1 and p246 was synthesized and cloned into the vector pPICZalphaA-TNFR2 by use of BamHI and NotI. The protein sequence of the resultant fusion protein TNFR2-COL18NC1-p246 is listed as SEQ ID NO:26. The optimized gene encoding COL18NC1 and p271 was synthesized and cloned into the vector pPICZalphaA-TNFR2 by use of BamHI and NotI. The protein sequence of the resultant fusion protein TNFR2-COL18NC1-p271 is listed as SEQ ID NO:27.

SEQ ID NO: 26
TNFR2-COL18NC1-p246 protein sequence. The COL18NC1 protein sequence is in italic and bold. The pCloud sequence p246 is underlined,.
LPAQVAFTPYAPEPGSTCRLREYYDQTAQMCCSKCSPGQHAKVFCTKTSD

TVCDSCEDSTYTQLWNWVPECLSCGSRCSSDQVETQACTREQNRICTCRP

GWYCALSKQEGCRLCAPLRKCRPGFGVARPGTETSDVVCKPCAPGTFSNT

TSSTDICRPHQICNVVAIPGNASMDAVCTSTSPTRSMAPGAVHLPQPVST

RSQHTQPTPEPSTAPSTSELLPMGPSPPAEGSTGDGGGSGGGSGGG

GASSGVRLWATRQAMLGQVHEVPEGWLIFVAEQEELYVRVQNGFRKVQL

EARTPLPRG

GGGSGGGSGSGSESGSGGGSTSSGTGSETESPGSG

SESGSGPSSAGSGGSGSESGSGSGSSGPGSTGGSGSESGSGPGSSGTGGTA

TGSGSESGSGPGSSGPGSTGSGSGSESGSGSGSSGTGSTGGSGSESGSGP

GSPRPGSTGTGGSGSESGSGPGSSERGSAGGGSGSESG

SGSESGSGSESGSGSGSESGSGPESPGSGGSGSESGSGTSGSTGSGSESG

SGGGSGGGSGG

SEQ ID NO: 27
TNFR2-COL18NC1-p271 protein sequence. The COL18NC1 protein sequence is in italic and bold. The pCloud sequence p271 is underlined,.
LPAQVAFTPYAPEPGSTCRLREYYDQTAQMCCSKCSPGQHAKVECTKTSD

TVCDSCEDSTYTQLWNWVPECLSCGSRCSSDQVETQACTREQNRICTCRP

GWYCALSKQEGCRLCAPLRKCRPGFGVARPGTETSDVVCKPCAPGTFSNT

TSSTDICRPHQICNVVAIPGNASMDAVCTSTSPTRSMAPGAVHLPQPVST

RSQHTQPTPEPSTAPSTSELLPMGPSPPAEGSTGDGGGSGGGSGGG

GASSGVRLWATRQAMLGQVHEVPEGWLIFVAEQEELYVRVQNGFRKVQL

EARTPLPRG

GGGSGGGSGGSGSESGSGGGSTSSGTGSETESPGGSG

SESGSGGPSSAGSGGSGSESGSGGSGSSGPGSTGGGSGSESGSGGPGSSG

TGGTATGGSGSESGSGGPGSSGPGSTGSGGSGSESGSGGSGSSGTGSTGG

GSGSESGSGGPGSPRPGSTGTGGSGSESGSGGPGSSERGSAGGGSGSESG

SGGTSESSASGSTGGGSGSESGSGGSESGSGGSGSESGSGGPESPGSGGG

SGSESGSGGTSGSTGGSGSESGSGGGGSGGGSGG

The protein expressions of TNFR2-COL18NC1-p246 and TNFR2-COL18NC1-p271 were carried out by use of the *pichia* system as described before. The secreted recombinant proteins were purified using the similar protocol described in example 3. The purified protein was kept in 20 mM Hepes buffer (pH 7.5), NaCl 150 mM. The purity of the fusion protein was examined by SDS-PAGE electrophoresis (purity >95%).

The biological activity of TNFR2-COL18NC1-p246 and TNFR2-COL18NC1-p271 was measured by its ability to block the TNF-alpha signaling. The positive control TNFR2-Fc fusion protein (R&D Systems) can efficiently block the apoptosis of L-929 mouse fibroblast cells induced by TNF-alpha (0.25 ng/mL) in the presence of actinomycin D. The ED50 of TNFR2-Fc fusion protein was shown to be ~5 ng/ml using the abovementioned assay. Our data indicated that TNFR2-COL18NC1-p246 and TNFR2-COL18NC1-p271 can inhibit the cell killing activity of TNF alpha for L929 cells with the ED50 of 1-5 ng/ml using the same assay. This suggested that TNFR2-COL18NC1-p246 and TNFR2-COL18NC1-p271 can function as efficiently as TNFR2-IgG1 Fc fusion protein in the in vitro studies.

Example 19: Construction of the Fusion Protein Containing VEGFR1R2, COL18NC1 and pCloud Sequences Vascular endothelial growth factor (VEGF) plays a critical role during normal embryonic angiogenesis and also in the pathological angiogenesis such as cancer. Numerous studies suggested that inhibiting VEGF functions may be an efficient treatment for cancer patients. VEGF-Trap was created by fusing the second Ig domain of VEGF receptor 1 (VEGFR1) with the third Ig domain of VEGF receptor 2 (VEGFR2) and the Fc fragment of IgG [52]. VEGF-trap has high affinity to VEGF and has shown promising anti-cancer efficacy in clinical trials. In this example, we constructed a novel fusion protein VEGFR1R2 that consists of human VEGFR1 second Ig domain and human VEGFR2 third Ig domain. Then we applied the method of the present invention to VEGFR1R2 to generate the tri-valent VEGFR1R2-COL18NC1-p246 and VEGFR1R2-COL18NC1-p271 fusion proteins.

The synthetic gene that encodes the human VEGFR1R2 was grafted into the digested vectors pPICZalphaA-TNFR2-COL18NC1-p246 and pPICZalphaA-TNFR2-COL18NC1-p271 generated in example 14 by use of XhoI and BamHI. The resultant fusion proteins were named as VEGFR1R2-COL18NC1-p246 and VEGFR1R2-COL18NC1-p271 and their protein sequences were listed as SEQ ID NO:28 and 29.

The protein expressions of VEGFR1R2-COL18NC1-p246 and VEGFR1R2-COL18NC1-p271 were carried out by use of the *pichia* system as described in example 13. The secreted recombinant proteins were purified using the similar protocol described in example 3. The purified protein was kept in 20 mM Hepes buffer (pH 7.5), NaCl 150_mM. The purity of the fusion protein was examined by SDS-PAGE electrophoresis (purity >95%). The biological activities of VEGFR1R2-COL18NC1-p246 and VEGFR1R2-COL18NC1-p271 were shown by its ability to interact with VEGF. Our data from SPR by use of Biacore 2000 (GE Healthcare) indicated that VEGFR1R2-COL18NC1-p246 and VEGFR1R2-COL18NC1-p271 fusion proteins can bind VEGF with the similar affinity as the VEGFR1R2-IgG Fc fusion protein.

SEQ ID NO: 28
VEGFR1R2-COL18NC1-p246 fusion protein sequence.
The COL18NC1 protein sequence is in italic and bold. The pCloud sequence p271 is underlined, .
SDTGRPFVEMYSEIPEIIHMTEGRELVIPCRVTSPNITVTLKKFPLDTLI

PDGKRIIWDSRKGFIISNATYKEIGLLTCEATVNGHLYKTNYLTHRQTNT

IIDVVLSPSHGIELSVGEKLVLNCTARTELNVGIDENWEYPSSKHQHKKL

VNRDLKTQSGSEMKKELSTLTIDGVTRSDQGLYTCAASSGLMTKKNSTFV

RVHEGGGSGGGSGG

GASSGVRLWATRQAMLGQVHEVPEGWLIFVAEQEELYVRVQNGFRKVQL

EARTPLPRG

GGGSGGGSGSGSESGSGGGSTSSGTGSETESPGSG

SESGSGPSSAGSGSGSESGSGSGSSGPGSTGGSGSESGSGPGSSGTGGTA

TGSGSESGSGPGSSGPGSTGSGSGSESGSGSGSSGTGSTGGSGSESGSGP

GSPRPGSTGTGSGSESGSGPGSSERGSAGGGSGSESGSGTSESSASGSTGG

SGSESGSGSESGSGSGSESGSGPESPGSGGSGSESGSGTSGSTGSGSESG

SGGGSGGGSGG

SEQ ID NO: 29
VEGFR1R2-COL18NC1-p271 fusion protein sequence.
The COL18NC1 protein sequence is in italic and bold. The pCloud sequence p271 is underlined, .
SDTGRPFVEMYSEIPEIIHMTEGRELVIPCRVTSPNITVTLKKFPLDTLI

PDGKRIIWDSRKGFIISNATYKEIGLLTCEATVNGHLYKTNYLTHRQTNT

IIDVVLSPSHGIELSVGEKLVLNCTARTELNVGIDENWEYPSSKHQHKKL

VNRDLKTQSGSEMKKELSTLTIDGVTRSDQGLYTCAASSGLMTKKNSTFV

RVHE

GGGSGGGSGG

GASSGVRLWATRQAMLGQVHEVPEGWLIFVAEQEELYVRVQNGFRKVQL

EARTPLPRG

GGGSGGGSGGSGSESGSGGGSTSSGTGSETESPGGSG

SESGSGGPSSAGSGGGSGSESGSGGSGSSGPGSTGGGSGSESGSGGPGSSG

TGGTATGGSGSESGSGGPGSSGPGSTGSGGSGSESGSGGSGSSGTGSTGG

GSGSESGSGGPGSPRPGSTGTGGSGSESGSGGPGSSERGSAGGGSGSESG

SGGTSESSASGSTGGGSGSESGSGGSESGSGGSGSESGSGGPESPGSGGG

SGSESGSGGTSGSTGGSGSESGSGGGGSGGGSGG

Example 20: Cloning and Expression of Exenatide (EX) Fused with Fn8, pCloud Sequence and Human Collagen XVIII NC1 (COL18NC1)

Exenatide (INN, marketed as Byetta, Bydureon) is a glucagon-like peptide-1 agonist (GLP-1 agonist) medication, belonging to the group of incretin mimetics, approved in April 2005 for the treatment of type II diabetes mellitus. To efficiently extend the in vivo half life of Exenatide, in this example, we have constructed the fusion proteins of Exenatide, Fn8, pCloud polypeptide and the scaffold protein COL18NC1 by use of the method of the present invention. The optimized gene encoding Exenatide and Fn8 was synthesized, digested by NdeI and BamHI and ligated into the digested vectors pET29b-GLP-1(A8G/G22E/R36G)-Fn8-p246-COL18NC1 and pET29b-GLP-1(A8G/G22E/R36G)-Fn8-p271-COL18NC1 generated in examples 4 and 9. The resulted fusion proteins were named as EX-Fn8-p246-COL18NC1 and EX-Fn8-p271-COL18NC1 and their protein sequences were listed as SEQ ID NO: 30 and 31.

The protein expressions and purifications of EX-Fn8-p246-COL18NC1 and EX-Fn8-p271-COL18NC1 were carried out as described in example 3. The biological activities of the fusion proteins could be measured by use of the cAMP assay described in example 11. The data fitting showed that the EC50 of EX-Fn8-p246-COL18NC1 and EX-Fn8-p271-COL18NC1 were ~0.11 nM and 0.08 nM, respectively.

SEQ ID NO: 30
EX-Fn8-p246-COL18NC1 protein sequence, the
Exenatide sequence is in Italic. The flexible loop
between EX and Fn8 is in bold. The pCloud sequence
p246 is underlined, .
*HGEGTFTSDLSKQMEEEAVRLFIEWLKNGGPSSGAPPPS*

SGGGSGGGSGGGSGGGSGSGGAVPPPTD

LRFTNIGPDTMRVTWAPPPSIDLTNFLVRYSPVKNEEDVAELSISPSDNA

VVLTNLLPGTEYVVSVSSVYEQHESTPLRGRQKTGGGGSGGGSGSGSESG

SGGGSTSSGTGSETESPGSGSESGSGPSSAGSGSGSESGSGSGSSGPGST

GGSGSESGSGPGSSGTGGTATGSGSESGSGPGSSGPGSTGSGSGSESGSG

SGSSGTGSTGGSGSESGSGPGSPRPGSTGTGSGSESGSGPGSSERGSAGG

SGSESGSGTSESSASGSTGGSGSESGSGSESGSGSGSESGSGPESPGSGG

SGSESGSGTSGSTGSGSESGSGGGSGGGSGGASSGVRLWATRQAMLGQV

HEVPEGWLIFVAEQEELYVRVQNGFRKVQLEARTPLPRG

SEQ ID NO: 31
EX-Fn8-p271-COL18NC1 protein sequence, the
Exenatide sequence is in Italic. The flexible
unstructured linker between EX and Fn8 is in bold.
The pCloud sequence p271 is underlined, .
*HGEGTFTSDLSKQMEEEAVRLFIEWLKNGGPSSGAPPPS*

SGGGSGGGSGGGSGGGSGSGGAVPPPTD

-continued

```
LRFTNIGPDTMRVTWAPPPSIDLTNFLVRYSPVKNEEDVAELSISPSDNA

VVLTNLLPGTEYVVSVSSVYEQHESTPLRGRQKTG

GGGSGGGSGGSGSESGSGGGSTSSGTGSETESPGGSG

SESGSGGPSSAGSGGSGSESGSGGSGSSGPGSTGGGSGSESGSGGPGSSG

TGGTATGGSGSESGSGGPGSSGPGSTGSGGSGSESGSGGSGSSGTGSTGG

GSGSESGSGGPGSPRPGSTGTGGSGSESGSGGPGSSERGSAGGGSGSESG

SGGTSESSASGSTGGGSGSESGSGGSESGSGGSGSESGSGGPESPGSGGG

SGSESGSGGTSGSTGGSGSESGSGGGSGGGSGG

GASSGVRLWATRQAMLGQVHEVPEGWLIFVAEQEELYVRVQNGFRKVQLE

ARTPLPRG
```

CITED PATENTS

1. U.S. Pat. No. 7,557,183 Polyethylene glycol linked GLP-1 compounds
2. U.S. Pat. No. 8,093,356 Pegylated human interferon polypeptides
3. U.S. Pat. No. 8,058,398 Modified G-CSF polypeptide
4. U.S. Pat. No. 7,052,686 Pegylated interleukin-10
5. U.S. Pat. No. 8,030,269 Calcitonin drug-oligomer conjugates, and uses thereof
6. United States Patent Application 20090325865 Liquid Formulations of Pegylated Growth Hormone
7. U.S. Pat. No. 8,053,561 Pegylated factor VIII
8. U.S. Pat. No. 8,053,410 Pegylated factor VII glycoforms
9. United States Patent Application 20090312236 PEGYLATED INSULIN LISPRO COMPOUNDS
10. U.S. Pat. No. 7,271,149 GLP-1 fusion proteins
11. U.S. Pat. No. 6,946,134 Albumin fusion proteins
12. U.S. Pat. No. 7,785,599 Albumin fusion proteins
13. WO2011140086 A2 Serum albumin binding molecules
14. EP2065402 A1 Trimeric collagen scaffold antibodies
15. U.S. Pat. No. 7,691,815 B2 Methods for blocking TNF-alpha activity in mammals with trimeric soluble TNF receptors

CITED LITERATURES

1. Molineux, G., *Pegylation: engineering improved biopharmaceuticals for oncology*. Pharmacotherapy, 2003. 23(8 Pt 2): p. 3S-8S.
2. Crawford, J., *Clinical uses of pegylated pharmaceuticals in oncology*. Cancer Treat Rev, 2002. 28 Suppl A: p. 7-11.
3. Pasut, G. and F. M. Veronese, *PEG conjugates in clinical development or use as anticancer agents: an overview*. Adv Drug Deliv Rev, 2009. 61(13): p. 1177-88.
4. Veronese, F. M. and A. Mero, *The impact of PEGylation on biological therapies*. BioDrugs, 2008. 22(5): p. 315-29.
5. Eliason, J. F., *Pegylated cytokines: potential application in immunotherapy of cancer*. BioDrugs, 2001. 15(11): p. 705-11.
6. Glaesner, W., et al., *Engineering and characterization of the long-acting glucagon-like peptide-1 analogue LY2189265, an Fc fusion protein*. Diabetes Metab Res Rev. 26(4): p. 287-96.
7. Picha, K. M., et al., *Protein engineering strategies for sustained glucagon-like peptide-1 receptor-dependent control of glucose homeostasis*. Diabetes, 2008. 57(7): p. 1926-34.
8. Bush, M. A., et al., *Safety, tolerability, pharmacodynamics and pharmacokinetics of albiglutide, a long-acting glucagon-like peptide-1 mimetic, in healthy subjects*. Diabetes Obes Metab, 2009. 11(5): p. 498-505.
9. Matthews, J. E., et al., *Pharmacodynamics, pharmacokinetics, safety, and tolerability of albiglutide, a long-acting glucagon-like peptide-1 mimetic, in patients with type 2 diabetes*. J Clin Endocrinol Metab, 2008. 93(12): p. 4810-7.
10. Garnier, J., D. J. Osguthorpe, and B. Robson, *Analysis of the accuracy and implications of simple methods for predicting the secondary structure of globular proteins*. J Mol Biol, 1978. 120(1): p. 97-120.
11. Todorovska, A., et al., *Design and application of diabodies, triabodies and tetrabodies for cancer targeting*. J Immunol Methods, 2001. 248(1-2): p. 47-66.
12. Sturniolo, T., et al., *Generation of tissue-specific and promiscuous HLA ligand databases using DNA microarrays and virtual HLA class II matrices*. Nat Biotechnol, 1999. 17(6): p. 555-61.
13. Schellenberger, V., et al., *A recombinant polypeptide extends the in vivo half-life of peptides and proteins in a tunable manner*. Nat Biotechnol, 2009. 27(12): p. 1186-90.
14. Sorensen, B., et al., *Fibrinogen as a hemostatic agent*. Semin Thromb Hemost, 2012. 38(3): p. 268-73.
15. Weisel, J. W. and R. I. Litvinov, *Mechanisms of fibrin polymerization and clinical implications*. Blood, 2013. 121(10): p. 1712-9.
16. Mosesson, M. W., *Fibrinogen and fibrin structure and functions*. J Thromb Haemost, 2005. 3(8): p. 1894-904.
17. Garnier, J., J. F. Gibrat, and B. Robson, *GOR method for predicting protein secondary structure from amino acid sequence*. Methods Enzymol, 1996. 266: p. 540-53.
18. Pankov, R. and K. M. Yamada, *Fibronectin at a glance*. J Cell Sci, 2002. 115(Pt 20): p. 3861-3.
19. Mao, Y. and J. E. Schwarzbauer, *Fibronectin fibrillogenesis, a cell-mediated matrix assembly process*. Matrix Biol, 2005. 24(6): p. 389-99.
20. Leahy, D. J., I. Aukhil, and H. P. Erickson, *2.0 A crystal structure of a four-domain segment of human fibronectin encompassing the RGD loop and synergy region*. Cell, 1996. 84(1): p. 155-64.
21. de Pereda, J. M., G. Wiche, and R. C. Liddington, *Crystal structure of a tandem pair of fibronectin type III domains from the cytoplasmic tail of integrin alpha6beta4*. EMBO J, 1999. 18(15): p. 4087-95.
22. Ricard-Blum, S. and F. Ruggiero, *The collagen superfamily: from the extracellular matrix to the cell membrane*. Pathol Biol (Paris), 2005. 53(7): p. 430-42.
23. Khoshnoodi, J., et al., *Molecular recognition in the assembly of collagens: terminal noncollagenous domains are key recognition modules in the formation of triple helical protomers*. J Biol Chem, 2006. 281(50): p. 38117-21.
24. Gordon, M. K. and R. A. Hahn, *Collagens*. Cell Tissue Res. 339(1): p. 247-57.
25. Shoulders, M. D. and R. T. Raines, *Collagen structure and stability*. Annu Rev Biochem, 2009. 78: p. 929-58.
26. Wirz, J. A., et al., *Crystal structure of the human collagen XV trimerization domain: a potent trimerizing unit common to multiplexin collagens*. Matrix Biol. 30(1): p. 9-15.
27. Boudko, S. P., et al., *The NC2 domain of collagen IX provides chain selection and heterotrimerization*. J Biol Chem. 285(31): p. 23721-31.

28. Boudko, S. P., J. Engel, and H. P. Bachinger, *Trimerization and triple helix stabilization of the collagen XIX NC2 domain.* J Biol Chem, 2008. 283(49): p. 34345-51.
29. Kvansakul, M., et al., *Crystal structure of the collagen alpha1(VIII) NC1 trimer.* Matrix Biol, 2003. 22(2): p. 145-52.
30. Bogin, O., et al., *Insight into Schmid metaphyseal chondrodysplasia from the crystal structure of the collagen X NC1 domain trimer.* Structure, 2002. 10(2): p. 165-73.
31. Sundaramoorthy, M., et al., *Crystal structure of NC1 domains. Structural basis for type IV collagen assembly in basement membranes.* J Biol Chem, 2002. 277(34): p. 31142-53.
32. Boudko, S. P., et al., *Crystal structure of human collagen XVIII trimerization domain: A novel collagen trimerization Fold.* J Mol Biol, 2009. 392(3): p. 787-802.
33. Ghai, R., et al., *C1q and its growing family.* Immunobiology, 2007. 212(4-5): p. 253-66.
34. Schaffler, A. and C. Buechler, *CTRP family: linking immunity to metabolism.* Trends Endocrinol Metab. 23(4): p. 194-204.
35. Kishore, U. and K. B. Reid, *C1q: structure, function, and receptors.* Immunopharmacology, 2000. 49(1-2): p. 159-70.
36. Farrah, T. and C. A. Smith, *Emerging cytokine family.* Nature, 1992. 358(6381): p. 26.
37. Cabal-Hierro, L. and P. S. Lazo, *Signal transduction by tumor necrosis factor receptors.* Cell Signal. 24(6): p. 1297-305.
38. Zelensky, A. N. and J. E. Gready, *The C-type lectin-like domain superfamily.* FEBS J, 2005. 272(24): p. 6179-217.
39. Feinberg, H., et al., *Trimeric structure of langerin.* J Biol Chem. 285(17): p. 13285-93.
40. Hakansson, K., et al., *Crystal structure of the trimeric alpha-helical coiled-coil and the three lectin domains of human lung surfactant protein D.* Structure, 1999. 7(3): p. 255-64.
41. Ng, K. K., et al., *Orientation of bound ligands in mannose-binding proteins. Implications for multivalent ligand recognition.* J Biol Chem, 2002. 277(18): p. 16088-95.
42. Nielsen, B. B., et al., *Crystal structure of tetranectin, a trimeric plasminogen-binding protein with an alpha-helical coiled coil.* FEBS Lett, 1997. 412(2): p. 388-96.
43. Holst, J. J., T. Vilsboll, and C. F. Deacon, *The incretin system and its role in type 2 diabetes mellitus.* Mol Cell Endocrinol, 2009. 297(1-2): p. 127-36.
44. Baggio, L. L. and D. J. Drucker, *Biology of incretins: GLP-1 and GIP.* Gastroenterology, 2007. 132(6): p. 2131-57.
45. Connaris, H., P. R. Crocker, and G. L. Taylor, *Enhancing the receptor affinity of the sialic acid-binding domain of Vibrio cholerae sialidase through multivalency.* J Biol Chem, 2009. 284(11): p. 7339-51.
46. Kim, D., et al., *Heptameric Targeting Ligands against EGFR and HER2 with High Stability and Avidity.* PLoS One. 7(8): p. e43077.
47. O'Reilly, M. K. and J. C. Paulson, *Multivalent ligands for siglecs.* Methods Enzymol. 478: p. 343-63.
48. Burcelin, R., et al., *Encapsulated, genetically engineered cells, secreting glucagon-like peptide-1 for the treatment of non-insulin-dependent diabetes mellitus.* Ann N Y Acad Sci, 1999. 875: p. 277-85.
49. Diez, J. J. and P. Iglesias, *The role of the novel adipocyte-derived hormone adiponectin in human disease.* Eur J Endocrinol, 2003. 148(3): p. 293-300.
50. Shapiro, L. and P. E. Scherer, *The crystal structure of a complement-1q family protein suggests an evolutionary link to tumor necrosis factor.* Curr Biol, 1998. 8(6): p. 335-8.
51. Aaltonen, K. J., et al., *Systematic review and meta-analysis of the efficacy and safety of existing TNF blocking agents in treatment of rheumatoid arthritis.* PLoS One. 7(1): p. e30275.
52. Stewart, M. W., *Aflibercept (VEGF-TRAP): the next anti-VEGF drug.* Inflamm Allergy Drug Targets. 10(6): p. 497-508.

The invention claimed is:

1. A fusion protein comprising a therapeutic polypeptide (TP) fused to one or more pCloud sequences and a scaffold protein,
   wherein TP is human glucagon-like peptide or a functional variant thereof,
   the scaffold protein forms a homo-trimer in solution and is selected from the group consisting of human collagen noncollagenous (NC) domains which form stable homo-trimers in solution, and
   the pCloud sequence is a flexible un-structured polypeptide comprising some or all of the fragments of the human fibrinogen alpha chain; and
   wherein the pCloud polypeptide sequence:
   (a) comprises at least 100 to about 3000 amino acid residues;
   (b) comprises some or all of the fragments derived from human fibrinogen alpha chain; wherein the fibrinogen alpha chain fragments are flanked by flexible loops with various lengths from 1 to 100 amino acid residues; wherein the flexible loops are rich in glycine (G) and serine (S), the flexible loops may also contain glutamate (E), alanine (A), proline (P) and threonine (T), the flexible loops have greater than 95% unstructured random coil formation as determined by GOR algorithm;
   (c) is rich in glycine (G), serine (S) and glutamate (E), and optionally further comprising alanine (A), proline (P), arginine (R) and threonine (T), and wherein the sum of G, S, E, A, P and T amino acid residues constitutes more than 90% of the pCloud amino acid sequence;
   (d) has greater than 90% unstructured random coil formation as determined by GOR algorithm; and
   (e) does not contain a T-cell epitope as predicted by TEPITOPE algorithm;
   wherein the pCloud sequence can be at either or both of the N-terminal and the C-terminal end of the therapeutic polypeptide, and the pCloud sequences can optionally be placed at either or both of the N-terminal and the C-terminal end of the scaffold protein; and
   wherein the pCloud polypeptides can be identical or different to each other;
   wherein the fusion protein is configured, from N-terminus to C-terminus, using the following formula:

(pCloud)m-TP-(pCloud)n-Scaffold-(pCloud)k, or (pCloud)m-Scaffold-(pCloud)n-TP-(pCloud)k wherein m is either 0 or 1, n is either 0 or 1, k is either 0 or 1, and m+n+k>=1, the digits indicate the number of presence of the designated polypeptides;

wherein m is either 0 or 1, n is either 0 or 1, k is either 0 or 1, and m+n+k>=1, the digits indicate the number of presence of the designated polypeptides; and wherein the fusion protein exhibits an improved pharmacokinetic profile when administered to a subject compared with the TP by itself.

2. The fusion protein of claim 1, wherein the human fibrinogen fragments are selected from

| | |
|---|---|
| GSTSSGTGSETESP; | SEQ ID NO: 32 |
| PSSAGS; | SEQ ID NO: 33 |
| SGSSGPGSTG; | SEQ ID NO: 34 |
| PGSSGTGGTAT; | SEQ ID NO: 35 |
| PGSSGPGSTGS; | SEQ ID NO: 36 |
| SGSSGTGSTG; | SEQ ID NO: 37 |
| PGSPRPGSTGT; | SEQ ID NO: 38 |
| PGSSERGSAG; | SEQ ID NO: 39 |
| TSESSASGSTG; | SEQ ID NO: 40 |
| SESGS; | SEQ ID NO: 41 |
| PESPGSG; or | SEQ ID NO: 42 |
| TSGST, | SEQ ID NO: 43 | and the flexible loops are selected from (G2S)n, (G3S)n SEQ ID NO: 91, (G4S)n SEQ ID NO: 92, (G5S)n SEQ ID NO: 93, (GS)n, (G2S2)n SEQ ID NO: 94, (GS2)n, (GS3)n SEQ ID NO: 95, (S2G)n, (S3G)n SEQ ID NO: 96, (S4G)n SEQ ID NO: 97, (S5G)n SEQ ID NO: 98, (SG)n, (S2G2)n SEQ ID NO: 99, (SG2)n, (SG3)n SEQ ID NO: 100 where n is an integer;

| | |
|---|---|
| GGGSGGGG; | SEQ ID NO: 77 |
| GGGSGGGGS; | SEQ ID NO: 90 |
| GSGG; | SEQ ID NO: 101 |
| GGGSGGG; | SEQ ID NO: 102 |
| GGGGSGGG; | SEQ ID NO: 103 |
| GGGSGG; | SEQ ID NO: 89 |
| GGGGSGG; | SEQ ID NO: 76 |
| GGGGSGGGGSGGGGSGGGGS; | SEQ ID NO: 104 |
| GGGGSGGGGSASSASTGGPSGGGGSGGGGS; | SEQ ID NO: 105 |
| GGGGSGGGGSTASSASTGGPSGGGGSGGGGSAPSSGSTSGGTAAGGGGSG GGGS; or | SEQ ID NO: 106 |
| GGGSGGGSGGGSTASSASTKGPSGGGSGGGSGGGSAPSSKSTSGGTAAGG GSGGGSGGGS. | SEQ ID NO: 107 |

3. The fusion protein of claim 1, wherein the TP is connected with the pCloud sequence via a proteinous connecting moiety (PCM) of human origin, wherein a flexible loop can be utilized to fuse the TP and the PCM, the flexible loop is as defined in claim 1, the PCM can be fused at either the N-terminal or the C-terminal end of the TP; wherein the fusion protein is configured, from N-terminus to C-terminus, according to the following formula:

(pCloud)$_m$-TP-Loop-PCM-(pCloud)$_n$-Scaffold-(pCloud)$_k$ or (pCloud)$_m$-Scaffold-(pCloud)$_n$-PCM-Loop-TP-(pCloud)$_k$ wherein:
(a) pCloud is the pCloud polypeptide as defined in claim 1 and can be identical or different to each other;
(b) TP is GLP-1 or a functional variant thereof;
(c) Scaffold indicates the scaffold protein as defined in claim 1;
(d) m is either 0 or 1, n is either 0 or 1, k is either 0 or 1, and m+n+k>=1, the digits indicate the number of presence of the designated polypeptides;
(e) Loop is a flexible loop as defined in claim 1; and
(f) PCM is the proteinous connecting moiety of human origin.

4. The fusion protein of claim 3, wherein the human fibrinogen alpha chain fragments are selected from

| | |
|---|---|
| GSTSSGTGSETESP; | SEQ ID NO: 32 |
| PSSAGS; | SEQ ID NO: 33 |
| SGSSGPGSTG; | SEQ ID NO: 34 |
| PGSSGTGGTAT; | SEQ ID NO: 35 |
| PGSSGPGSTGS; | SEQ ID NO: 36 |
| SGSSGTGSTG; | SEQ ID NO: 37 |
| PGSPRPGSTGT; | SEQ ID NO: 38 |
| PGSSERGSAG; | SEQ ID NO: 39 |
| TSESSASGSTG; | SEQ ID NO: 40 |
| SESGS; | SEQ ID NO: 41 |
| PESPGSG; or | SEQ ID NO: 42 |
| TSGST, | SEQ ID NO: 43 | and the flexible loops are selected from (G2S)n, (G3S)n SEQ ID NO: 91, (G4S)n SEQ ID NO: 92, (G5S)n SEQ ID NO: 93, (GS)n, (G2S2)n SEQ ID NO: 94, (GS2)n, (GS3)n SEQ ID NO: 95, (S2G)n, (S3G)n SEQ ID NO: 96, (S4G)n SEQ ID NO: 97, (S5G)n SEQ ID NO: 98, (SG)n, (S2G2)n SEQ ID NO: 99, (SG2)n, (SG3)n SEQ ID NO: 100 where n is an integer;

| | |
|---|---|
| GGGSGGGG; | SEQ ID NO: 77 |
| GGGSGGGGS; | SEQ ID NO: 90 |

-continued

GSGG; SEQ ID NO: 101

GGGSGGG; SEQ ID NO: 102

GGGGSGGG; SEQ ID NO: 103

GGGSGG; SEQ ID NO: 89

GGGGSGG; SEQ ID NO: 76

GGGGSGGGSGGGSGGGGS; SEQ ID NO: 104

GGGGSGGGSASSASTGGPSGGGGSGGGGS; SEQ ID NO: 105

GGGGSGGGSTASSASTGGPSGGGGSGGGGSAPSSGSTSGGTAAGGGGSG GGGS; SEQ ID NO: 106 or

GGGSGGGSGGGSTASSASTKGPSGGGSGGGSGGGSAPSSKSTSGGTAAGG GSGGGSGGGS. SEQ ID NO: 107

5. The fusion protein of claim 4, wherein the PCM is a human Fibronectin type III domain.

6. The fusion protein of claim 4, wherein the fusion protein comprises:
 (i) a TP selected from the group consisting of GLP-1, GLP-1(A8G/G22E), GLP-1(A8G/G22E/R36G) and GLP-1(A8G/G22E/R36S);
 (ii) a flexible loop;
 (iii) a PCM selected from the group consisting of human fibronectin type III domain 7 (Fn7), and human fibronectin type III domain 8 (Fn8);
 (iv) a pCloud polypeptide sequence as defined in claim 1; and
 (v) the scaffold protein is the human collagen XVIII NC1 domain (COL18NC1).

7. The fusion protein of claim 5, wherein the fusion protein comprises:
 (i) GLP-1(A8G/G22E/R36S) or GLP-1(A8G/G22E/R36G);
 (ii) a flexible loop;
 (iii) the PCM is Fn8;
 (iv) a pCloud polypeptide; and
 (v) the scaffold protein is the human collagen XVIII NC1 domain COL18NC1.

* * * * *

SEQUENCE LISTING

```
<160> NUMBER OF SEQ ID NOS: 107

<210> SEQ ID NO 1
<211> LENGTH: 198
<212> TYPE: PRT
<213> ORGANISM: Artificial Sequence
<220> FEATURE:
<223> OTHER INFORMATION: synthesized

<400> SEQUENCE: 1

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly Gly
            20                  25                  30

Gly Gly Ser Gly Gly Gly Gly Thr Pro Leu Ser Pro Thr Asn Leu
        35                  40                  45

His Leu Glu Ala Asn Pro Asp Thr Gly Val Leu Thr Val Ser Trp Glu
    50                  55                  60

Arg Ser Thr Thr Pro Asp Ile Thr Gly Tyr Arg Ile Thr Thr Thr Pro
65                  70                  75                  80

Thr Asn Gly Gln Gln Gly Asn Ser Leu Glu Glu Val Val His Ala Asp
                85                  90                  95
```

```
Gln Ser Ser Cys Thr Phe Asp Asn Leu Ser Pro Gly Leu Glu Tyr Asn
                100                 105                 110

Val Ser Val Tyr Thr Val Lys Asp Asp Lys Glu Ser Val Pro Ile Ser
            115                 120                 125

Asp Thr Ile Ile Pro Ala Gly Gly Ser Gly Gly Ala Ser Ser
        130                 135                 140

Gly Val Arg Leu Trp Ala Thr Arg Gln Ala Met Leu Gly Gln Val His
145                 150                 155                 160

Glu Val Pro Glu Gly Trp Leu Ile Phe Val Ala Glu Gln Glu Leu
                165                 170                 175

Tyr Val Arg Val Gln Asn Gly Phe Arg Lys Val Gln Leu Glu Ala Arg
                180                 185                 190

Thr Pro Leu Pro Arg Gly
            195

<210> SEQ ID NO 2
<211> LENGTH: 196
<212> TYPE: PRT
<213> ORGANISM: Artificial Sequence
<220> FEATURE:
<223> OTHER INFORMATION: synthesized

<400> SEQUENCE: 2

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly Gly
            20                  25                  30

Gly Gly Ser Gly Gly Gly Gly Ser Ala Val Pro Pro Thr Asp Leu
        35                  40                  45

Arg Phe Thr Asn Ile Gly Pro Asp Thr Met Arg Val Thr Trp Ala Pro
    50                  55                  60

Pro Pro Ser Ile Asp Leu Thr Asn Phe Leu Val Arg Tyr Ser Pro Val
65                  70                  75                  80

Lys Asn Glu Glu Asp Val Ala Glu Leu Ser Ile Ser Pro Ser Asp Asn
                85                  90                  95

Ala Val Val Leu Thr Asn Leu Leu Pro Gly Thr Glu Tyr Val Val Ser
                100                 105                 110

Val Ser Ser Val Tyr Glu Gln His Glu Ser Thr Pro Leu Arg Gly Arg
            115                 120                 125

Gln Lys Thr Gly Gly Gly Gly Ser Gly Gly Gly Ala Ser Ser Gly Val
        130                 135                 140

Arg Leu Trp Ala Thr Arg Gln Ala Met Leu Gly Gln Val His Glu Val
145                 150                 155                 160

Pro Glu Gly Trp Leu Ile Phe Val Ala Glu Gln Glu Leu Tyr Val
                165                 170                 175

Arg Val Gln Asn Gly Phe Arg Lys Val Gln Leu Glu Ala Arg Thr Pro
                180                 185                 190

Leu Pro Arg Gly
        195

<210> SEQ ID NO 3
<211> LENGTH: 196
<212> TYPE: PRT
<213> ORGANISM: Artificial Sequence
<220> FEATURE:
<223> OTHER INFORMATION: synthesized
```

```
<400> SEQUENCE: 3

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Arg Gly Gly
            20                  25                  30

Gly Gly Ser Gly Gly Gly Gly Ser Ala Val Pro Pro Thr Asp Leu
        35                  40                  45

Arg Phe Thr Asn Ile Gly Pro Asp Thr Met Arg Val Thr Trp Ala Pro
    50                  55                  60

Pro Pro Ser Ile Asp Leu Thr Asn Phe Leu Val Arg Tyr Ser Pro Val
65                  70                  75                  80

Lys Asn Glu Glu Asp Val Ala Glu Leu Ser Ile Ser Pro Ser Asp Asn
                85                  90                  95

Ala Val Val Leu Thr Asn Leu Leu Pro Gly Thr Glu Tyr Val Val Ser
                100                 105                 110

Val Ser Ser Val Tyr Glu Gln His Glu Ser Thr Pro Leu Arg Gly Arg
            115                 120                 125

Gln Lys Thr Gly Gly Gly Gly Ser Gly Gly Gly Ala Ser Ser Gly Val
        130                 135                 140

Arg Leu Trp Ala Thr Arg Gln Ala Met Leu Gly Gln Val His Glu Val
145                 150                 155                 160

Pro Glu Gly Trp Leu Ile Phe Val Ala Glu Gln Glu Leu Tyr Val
                165                 170                 175

Arg Val Gln Asn Gly Phe Arg Lys Val Gln Leu Glu Ala Arg Thr Pro
            180                 185                 190

Leu Pro Arg Gly
        195

<210> SEQ ID NO 4
<211> LENGTH: 196
<212> TYPE: PRT
<213> ORGANISM: Artificial Sequence
<220> FEATURE:
<223> OTHER INFORMATION: synthesized

<400> SEQUENCE: 4

His Val Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Arg Gly Gly
            20                  25                  30

Gly Gly Ser Gly Gly Gly Gly Ser Ala Val Pro Pro Thr Asp Leu
        35                  40                  45

Arg Phe Thr Asn Ile Gly Pro Asp Thr Met Arg Val Thr Trp Ala Pro
    50                  55                  60

Pro Pro Ser Ile Asp Leu Thr Asn Phe Leu Val Arg Tyr Ser Pro Val
65                  70                  75                  80

Lys Asn Glu Glu Asp Val Ala Glu Leu Ser Ile Ser Pro Ser Asp Asn
                85                  90                  95

Ala Val Val Leu Thr Asn Leu Leu Pro Gly Thr Glu Tyr Val Val Ser
                100                 105                 110

Val Ser Ser Val Tyr Glu Gln His Glu Ser Thr Pro Leu Arg Gly Arg
            115                 120                 125

Gln Lys Thr Gly Gly Gly Gly Ser Gly Gly Gly Ala Ser Ser Gly Val
        130                 135                 140

Arg Leu Trp Ala Thr Arg Gln Ala Met Leu Gly Gln Val His Glu Val
```

```
                145                 150                 155                 160
Pro Glu Gly Trp Leu Ile Phe Val Ala Glu Gln Glu Glu Leu Tyr Val
                    165                 170                 175

Arg Val Gln Asn Gly Phe Arg Lys Val Gln Leu Glu Ala Arg Thr Pro
                    180                 185                 190

Leu Pro Arg Gly
            195

<210> SEQ ID NO 5
<211> LENGTH: 196
<212> TYPE: PRT
<213> ORGANISM: Artificial Sequence
<220> FEATURE:
<223> OTHER INFORMATION: synthesized

<400> SEQUENCE: 5

His Ser Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Arg Gly Gly
                20                  25                  30

Gly Gly Ser Gly Gly Gly Gly Ser Ala Val Pro Pro Pro Thr Asp Leu
            35                  40                  45

Arg Phe Thr Asn Ile Gly Pro Asp Thr Met Arg Val Thr Trp Ala Pro
50                  55                  60

Pro Pro Ser Ile Asp Leu Thr Asn Phe Leu Val Arg Tyr Ser Pro Val
65                  70                  75                  80

Lys Asn Glu Glu Asp Val Ala Glu Leu Ser Ile Ser Pro Ser Asp Asn
                85                  90                  95

Ala Val Val Leu Thr Asn Leu Leu Pro Gly Thr Glu Tyr Val Val Ser
                100                 105                 110

Val Ser Ser Val Tyr Glu Gln His Glu Ser Thr Pro Leu Arg Gly Arg
            115                 120                 125

Gln Lys Thr Gly Gly Gly Ser Gly Gly Gly Ala Ser Ser Gly Val
    130                 135                 140

Arg Leu Trp Ala Thr Arg Gln Ala Met Leu Gly Gln Val His Glu Val
145                 150                 155                 160

Pro Glu Gly Trp Leu Ile Phe Val Ala Glu Gln Glu Glu Leu Tyr Val
                    165                 170                 175

Arg Val Gln Asn Gly Phe Arg Lys Val Gln Leu Glu Ala Arg Thr Pro
                    180                 185                 190

Leu Pro Arg Gly
            195

<210> SEQ ID NO 6
<211> LENGTH: 196
<212> TYPE: PRT
<213> ORGANISM: Artificial Sequence
<220> FEATURE:
<223> OTHER INFORMATION: synthesized

<400> SEQUENCE: 6

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Ser Gly Gly
                20                  25                  30

Gly Gly Ser Gly Gly Gly Gly Ser Ala Val Pro Pro Pro Thr Asp Leu
            35                  40                  45
```

Arg Phe Thr Asn Ile Gly Pro Asp Thr Met Arg Val Thr Trp Ala Pro
 50                  55                  60

Pro Pro Ser Ile Asp Leu Thr Asn Phe Leu Val Arg Tyr Ser Pro Val
 65                  70                  75                  80

Lys Asn Glu Glu Asp Val Ala Glu Leu Ser Ile Ser Pro Ser Asp Asn
                 85                  90                  95

Ala Val Val Leu Thr Asn Leu Leu Pro Gly Thr Glu Tyr Val Val Ser
             100                 105                 110

Val Ser Ser Val Tyr Glu Gln His Glu Ser Thr Pro Leu Arg Gly Arg
         115                 120                 125

Gln Lys Thr Gly Gly Gly Gly Ser Gly Gly Gly Ala Ser Ser Gly Val
 130                 135                 140

Arg Leu Trp Ala Thr Arg Gln Ala Met Leu Gly Gln Val His Glu Val
 145                 150                 155                 160

Pro Glu Gly Trp Leu Ile Phe Val Ala Glu Gln Glu Leu Tyr Val
                 165                 170                 175

Arg Val Gln Asn Gly Phe Arg Lys Val Gln Leu Glu Ala Arg Thr Pro
             180                 185                 190

Leu Pro Arg Gly
         195

<210> SEQ ID NO 7
<211> LENGTH: 196
<212> TYPE: PRT
<213> ORGANISM: Artificial Sequence
<220> FEATURE:
<223> OTHER INFORMATION: synthesized

<400> SEQUENCE: 7

His Gly Glu Gly Thr Phe Thr Ser Asp Val Ser Ser Tyr Leu Glu Glu
 1               5                   10                  15

Gln Ala Ala Lys Glu Phe Ile Ala Trp Leu Val Lys Gly Gly Gly Gly
                 20                  25                  30

Gly Gly Ser Gly Gly Gly Gly Ser Ala Val Pro Pro Thr Asp Leu
             35                  40                  45

Arg Phe Thr Asn Ile Gly Pro Asp Thr Met Arg Val Thr Trp Ala Pro
 50                  55                  60

Pro Pro Ser Ile Asp Leu Thr Asn Phe Leu Val Arg Tyr Ser Pro Val
 65                  70                  75                  80

Lys Asn Glu Glu Asp Val Ala Glu Leu Ser Ile Ser Pro Ser Asp Asn
                 85                  90                  95

Ala Val Val Leu Thr Asn Leu Leu Pro Gly Thr Glu Tyr Val Val Ser
             100                 105                 110

Val Ser Ser Val Tyr Glu Gln His Glu Ser Thr Pro Leu Arg Gly Arg
         115                 120                 125

Gln Lys Thr Gly Gly Gly Gly Ser Gly Gly Gly Ala Ser Ser Gly Val
 130                 135                 140

Arg Leu Trp Ala Thr Arg Gln Ala Met Leu Gly Gln Val His Glu Val
 145                 150                 155                 160

Pro Glu Gly Trp Leu Ile Phe Val Ala Glu Gln Glu Leu Tyr Val
                 165                 170                 175

Arg Val Gln Asn Gly Phe Arg Lys Val Gln Leu Glu Ala Arg Thr Pro
             180                 185                 190

Leu Pro Arg Gly
         195

<210> SEQ ID NO 8
<211> LENGTH: 207
<212> TYPE: PRT
<213> ORGANISM: Artificial Sequence
<220> FEATURE:
<223> OTHER INFORMATION: synthesized

<400> SEQUENCE: 8

```
His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Ser Gly Gly
            20                  25                  30

Gly Gly Ser Gly Gly Ala Val Pro Pro Thr Asp Leu Arg Phe Thr
        35                  40                  45

Asn Ile Gly Pro Asp Thr Met Arg Val Thr Trp Ala Pro Pro Pro Ser
    50                  55                  60

Ile Asp Leu Thr Asn Phe Leu Val Arg Tyr Ser Pro Val Lys Asn Glu
65                  70                  75                  80

Glu Asp Val Ala Glu Leu Ser Ile Ser Pro Ser Asp Asn Ala Val Val
                85                  90                  95

Leu Thr Asn Leu Leu Pro Gly Thr Glu Tyr Val Val Ser Val Ser Ser
            100                 105                 110

Val Tyr Glu Gln His Glu Ser Thr Pro Leu Arg Gly Arg Gln Lys Thr
        115                 120                 125

Gly Gly Gly Gly Gly Ser Gly Gly Gly Ser Gly Gly Gly Gly Ser
    130                 135                 140

Gly Gly Gly Gly Ser Ala Ser Ser Gly Val Arg Leu Trp Ala Thr
145                 150                 155                 160

Arg Gln Ala Met Leu Gly Gln Val His Glu Val Pro Glu Gly Trp Leu
                165                 170                 175

Ile Phe Val Ala Glu Gln Glu Leu Tyr Val Arg Val Gln Asn Gly
            180                 185                 190

Phe Arg Lys Val Gln Leu Glu Ala Arg Thr Pro Leu Pro Arg Gly
        195                 200                 205
```

<210> SEQ ID NO 9
<211> LENGTH: 217
<212> TYPE: PRT
<213> ORGANISM: Artificial Sequence
<220> FEATURE:
<223> OTHER INFORMATION: synthesized

<400> SEQUENCE: 9

```
His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Ser Gly Gly
            20                  25                  30

Gly Gly Ser Gly Gly Ala Val Pro Pro Thr Asp Leu Arg Phe Thr
        35                  40                  45

Asn Ile Gly Pro Asp Thr Met Arg Val Thr Trp Ala Pro Pro Pro Ser
    50                  55                  60

Ile Asp Leu Thr Asn Phe Leu Val Arg Tyr Ser Pro Val Lys Asn Glu
65                  70                  75                  80

Glu Asp Val Ala Glu Leu Ser Ile Ser Pro Ser Asp Asn Ala Val Val
                85                  90                  95

Leu Thr Asn Leu Leu Pro Gly Thr Glu Tyr Val Val Ser Val Ser Ser
            100                 105                 110
```

Val Tyr Glu Gln His Glu Ser Thr Pro Leu Arg Gly Arg Gln Lys Thr
            115                 120                 125

Gly Gly Gly Gly Gly Ser Gly Gly Gly Ser Ala Ser Ser Ala Ser
130                 135                 140

Thr Gly Gly Pro Ser Gly Gly Gly Ser Gly Gly Gly Ser Gly
145                 150                 155                 160

Ala Ser Ser Gly Val Arg Leu Trp Ala Thr Arg Gln Ala Met Leu Gly
            165                 170                 175

Gln Val His Glu Val Pro Gly Gly Trp Leu Ile Phe Val Ala Glu Gln
            180                 185                 190

Glu Glu Leu Tyr Val Arg Val Gln Asn Gly Phe Arg Lys Val Gln Leu
            195                 200                 205

Glu Ala Arg Thr Pro Leu Pro Arg Gly
            210                 215

<210> SEQ ID NO 10
<211> LENGTH: 241
<212> TYPE: PRT
<213> ORGANISM: Artificial Sequence
<220> FEATURE:
<223> OTHER INFORMATION: synthesized

<400> SEQUENCE: 10

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Ser Gly Gly
            20                  25                  30

Gly Gly Ser Gly Gly Ala Val Pro Pro Pro Thr Asp Leu Arg Phe Thr
            35                  40                  45

Asn Ile Gly Pro Asp Thr Met Arg Val Thr Trp Ala Pro Pro Pro Ser
50                  55                  60

Ile Asp Leu Thr Asn Phe Leu Val Arg Tyr Ser Pro Val Lys Asn Glu
65                  70                  75                  80

Glu Asp Val Ala Glu Leu Ser Ile Ser Pro Ser Asp Asn Ala Val Val
            85                  90                  95

Leu Thr Asn Leu Leu Pro Gly Thr Glu Tyr Val Val Ser Val Ser Ser
            100                 105                 110

Val Tyr Glu Gln His Glu Ser Thr Pro Leu Arg Gly Arg Gln Lys Thr
            115                 120                 125

Gly Gly Gly Gly Gly Ser Gly Gly Gly Ser Thr Ala Ser Ser Ala
130                 135                 140

Ser Thr Gly Gly Pro Ser Gly Gly Gly Ser Gly Gly Gly Ser
145                 150                 155                 160

Ala Pro Ser Ser Gly Ser Thr Ser Gly Thr Ala Ala Gly Gly
            165                 170                 175

Gly Ser Gly Gly Gly Gly Ser Gly Ala Ser Ser Gly Val Arg Leu Trp
            180                 185                 190

Ala Thr Arg Gln Ala Met Leu Gly Gln Val His Glu Val Pro Glu Gly
            195                 200                 205

Trp Leu Ile Phe Val Ala Glu Gln Glu Glu Leu Tyr Val Arg Val Gln
            210                 215                 220

Asn Gly Phe Arg Lys Val Gln Leu Glu Ala Arg Thr Pro Leu Pro Arg
225                 230                 235                 240

Gly

```
<210> SEQ ID NO 11
<211> LENGTH: 247
<212> TYPE: PRT
<213> ORGANISM: Artificial Sequence
<220> FEATURE:
<223> OTHER INFORMATION: synthesized

<400> SEQUENCE: 11

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Ser Gly Gly
            20                  25                  30

Gly Gly Ser Gly Gly Ala Val Pro Pro Thr Asp Leu Arg Phe Thr
        35                  40                  45

Asn Ile Gly Pro Asp Thr Met Arg Val Thr Trp Ala Pro Pro Ser
    50                  55                  60

Ile Asp Leu Thr Asn Phe Leu Val Arg Tyr Ser Pro Val Lys Asn Glu
65                  70                  75                  80

Glu Asp Val Ala Glu Leu Ser Ile Ser Pro Ser Asp Asn Ala Val Val
                85                  90                  95

Leu Thr Asn Leu Leu Pro Gly Thr Glu Tyr Val Val Ser Val Ser Ser
            100                 105                 110

Val Tyr Glu Gln His Glu Ser Thr Pro Leu Arg Gly Arg Gln Lys Thr
        115                 120                 125

Gly Gly Gly Gly Ser Gly Gly Gly Ser Gly Gly Gly Ser Thr Ala Ser
    130                 135                 140

Ser Ala Ser Thr Lys Gly Pro Ser Gly Gly Ser Gly Gly Gly Ser
145                 150                 155                 160

Gly Gly Gly Ser Ala Pro Ser Ser Lys Ser Thr Ser Gly Gly Thr Ala
                165                 170                 175

Ala Gly Gly Ser Gly Gly Gly Ser Gly Gly Gly Ser Gly Ala Ser
            180                 185                 190

Ser Gly Val Arg Leu Trp Ala Thr Arg Gln Ala Met Leu Gly Gln Val
        195                 200                 205

His Glu Val Pro Glu Gly Trp Leu Ile Phe Val Ala Glu Gln Glu Glu
    210                 215                 220

Leu Tyr Val Arg Val Gln Asn Gly Phe Arg Lys Val Gln Leu Glu Ala
225                 230                 235                 240

Arg Thr Pro Leu Pro Arg Gly
                245

<210> SEQ ID NO 12
<211> LENGTH: 448
<212> TYPE: PRT
<213> ORGANISM: Artificial Sequence
<220> FEATURE:
<223> OTHER INFORMATION: synthesized

<400> SEQUENCE: 12

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Arg Gly Ser
            20                  25                  30

Gly Gly Gly Ser Gly Gly Gly Ser Gly Gly Gly Ser Gly Gly Gly Ser
        35                  40                  45

Gly Ser Gly Gly Ala Val Pro Pro Thr Asp Leu Arg Phe Thr Asn
    50                  55                  60
```

Ile Gly Pro Asp Thr Met Arg Val Thr Trp Ala Pro Pro Ser Ile
65                  70                  75                  80

Asp Leu Thr Asn Phe Leu Val Arg Tyr Ser Pro Val Lys Asn Glu Glu
            85                  90                  95

Asp Val Ala Glu Leu Ser Ile Ser Pro Ser Asp Asn Ala Val Val Leu
            100                 105                 110

Thr Asn Leu Leu Pro Gly Thr Glu Tyr Val Val Ser Val Ser Ser Val
            115                 120                 125

Tyr Glu Gln His Glu Ser Thr Pro Leu Arg Gly Arg Gln Lys Thr Gly
            130                 135                 140

Gly Gly Gly Ser Gly Gly Gly Ser Gly Ser Glu Ser Gly Ser
145                 150                 155                 160

Gly Gly Gly Ser Thr Ser Ser Gly Thr Gly Ser Glu Thr Glu Ser Pro
            165                 170                 175

Gly Ser Gly Ser Glu Ser Gly Ser Gly Pro Ser Ser Ala Gly Ser Gly
            180                 185                 190

Ser Gly Ser Glu Ser Gly Ser Gly Ser Ser Gly Pro Gly Ser
            195                 200                 205

Thr Gly Gly Ser Gly Ser Glu Ser Gly Ser Gly Pro Gly Ser Ser Gly
210                 215                 220

Thr Gly Gly Thr Ala Thr Gly Ser Gly Ser Glu Ser Gly Ser Gly Pro
225                 230                 235                 240

Gly Ser Ser Gly Pro Gly Ser Thr Gly Ser Gly Ser Gly Ser Glu Ser
            245                 250                 255

Gly Ser Gly Ser Gly Ser Ser Gly Thr Gly Ser Thr Gly Ser Gly
            260                 265                 270

Ser Glu Ser Gly Ser Gly Pro Gly Ser Pro Arg Pro Gly Ser Thr Gly
            275                 280                 285

Thr Gly Ser Gly Ser Glu Ser Gly Ser Gly Pro Gly Ser Ser Glu Arg
            290                 295                 300

Gly Ser Ala Gly Gly Ser Gly Ser Glu Ser Gly Ser Gly Thr Ser Glu
305                 310                 315                 320

Ser Ser Ala Ser Gly Ser Thr Gly Gly Ser Gly Ser Glu Ser Gly Ser
            325                 330                 335

Gly Ser Glu Ser Gly Ser Gly Ser Gly Ser Glu Ser Gly Ser Gly Pro
            340                 345                 350

Glu Ser Pro Gly Ser Gly Ser Gly Ser Glu Ser Gly Ser Gly Thr
            355                 360                 365

Ser Gly Ser Thr Gly Ser Gly Ser Glu Ser Gly Ser Gly Gly Gly Ser
            370                 375                 380

Gly Gly Gly Ser Gly Gly Gly Ala Ser Ser Gly Val Arg Leu Trp Ala
385                 390                 395                 400

Thr Arg Gln Ala Met Leu Gly Gln Val His Glu Val Pro Glu Gly Trp
            405                 410                 415

Leu Ile Phe Val Ala Glu Gln Glu Glu Leu Tyr Val Arg Val Gln Asn
            420                 425                 430

Gly Phe Arg Lys Val Gln Leu Glu Ala Arg Thr Pro Leu Pro Arg Gly
            435                 440                 445

<210> SEQ ID NO 13
<211> LENGTH: 448
<212> TYPE: PRT
<213> ORGANISM: Artificial Sequence
<220> FEATURE:

-continued

<223> OTHER INFORMATION: synthesized

<400> SEQUENCE: 13

```
His Val Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Arg Gly Ser
            20                  25                  30

Gly Gly Gly Ser Gly Gly Gly Ser Gly Gly Gly Ser Gly Gly Gly Ser
        35                  40                  45

Gly Ser Gly Gly Ala Val Pro Pro Thr Asp Leu Arg Phe Thr Asn
    50                  55                  60

Ile Gly Pro Asp Thr Met Arg Val Thr Trp Ala Pro Pro Ser Ile
65                  70                  75                  80

Asp Leu Thr Asn Phe Leu Val Arg Tyr Ser Pro Val Lys Asn Glu Glu
                85                  90                  95

Asp Val Ala Glu Leu Ser Ile Ser Pro Ser Asp Asn Ala Val Val Leu
            100                 105                 110

Thr Asn Leu Leu Pro Gly Thr Glu Tyr Val Val Ser Val Ser Ser Val
        115                 120                 125

Tyr Glu Gln His Glu Ser Thr Pro Leu Arg Gly Arg Gln Lys Thr Gly
130                 135                 140

Gly Gly Gly Ser Gly Gly Gly Ser Gly Ser Gly Ser Glu Ser Gly Ser
145                 150                 155                 160

Gly Gly Gly Ser Thr Ser Ser Gly Thr Gly Ser Glu Thr Glu Ser Pro
                165                 170                 175

Gly Ser Gly Ser Glu Ser Gly Ser Gly Pro Ser Ser Ala Gly Ser Gly
            180                 185                 190

Ser Gly Ser Glu Ser Gly Ser Gly Ser Ser Gly Pro Gly Ser
        195                 200                 205

Thr Gly Gly Ser Gly Ser Glu Ser Gly Ser Gly Pro Gly Ser Ser Gly
210                 215                 220

Thr Gly Gly Thr Ala Thr Gly Ser Gly Ser Glu Ser Gly Ser Gly Pro
225                 230                 235                 240

Gly Ser Ser Gly Pro Gly Ser Thr Gly Ser Gly Ser Gly Ser Glu Ser
                245                 250                 255

Gly Ser Gly Ser Gly Ser Ser Gly Thr Gly Ser Thr Gly Gly Ser Gly
            260                 265                 270

Ser Glu Ser Gly Ser Gly Pro Gly Ser Pro Arg Pro Gly Ser Thr Gly
        275                 280                 285

Thr Gly Ser Gly Ser Glu Ser Gly Ser Gly Pro Gly Ser Ser Glu Arg
290                 295                 300

Gly Ser Ala Gly Gly Ser Gly Ser Glu Ser Gly Ser Gly Thr Ser Glu
305                 310                 315                 320

Ser Ser Ala Ser Gly Thr Gly Ser Gly Ser Glu Ser Gly Ser
                325                 330                 335

Gly Ser Glu Ser Gly Ser Gly Ser Glu Ser Gly Ser Gly Pro
            340                 345                 350

Glu Ser Pro Gly Ser Gly Gly Ser Gly Ser Gly Ser Gly Thr
        355                 360                 365

Ser Gly Ser Thr Gly Ser Gly Ser Glu Ser Gly Ser Gly Gly Gly Ser
        370                 375                 380

Gly Gly Gly Ser Gly Gly Gly Ala Ser Ser Gly Val Arg Leu Trp Ala
385                 390                 395                 400
```

Thr Arg Gln Ala Met Leu Gly Gln Val His Glu Val Pro Glu Gly Trp
            405                 410                 415

Leu Ile Phe Val Ala Glu Gln Glu Leu Tyr Val Arg Val Gln Asn
            420                 425                 430

Gly Phe Arg Lys Val Gln Leu Glu Ala Arg Thr Pro Leu Pro Arg Gly
            435                 440                 445

<210> SEQ ID NO 14
<211> LENGTH: 448
<212> TYPE: PRT
<213> ORGANISM: Artificial Sequence
<220> FEATURE:
<223> OTHER INFORMATION: synthesized

<400> SEQUENCE: 14

His Ser Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Arg Gly Ser
            20                  25                  30

Gly Gly Gly Ser Gly Gly Gly Ser Gly Gly Ser Gly Gly Gly Gly Ser
        35                  40                  45

Gly Ser Gly Gly Ala Val Pro Pro Thr Asp Leu Arg Phe Thr Asn
    50                  55                  60

Ile Gly Pro Asp Thr Met Arg Val Thr Trp Ala Pro Pro Pro Ser Ile
65                  70                  75                  80

Asp Leu Thr Asn Phe Leu Val Arg Tyr Ser Pro Val Lys Asn Glu Glu
                85                  90                  95

Asp Val Ala Glu Leu Ser Ile Ser Pro Ser Asp Asn Ala Val Val Leu
            100                 105                 110

Thr Asn Leu Leu Pro Gly Thr Glu Tyr Val Val Ser Val Ser Ser Val
        115                 120                 125

Tyr Glu Gln His Glu Ser Thr Pro Leu Arg Gly Arg Gln Lys Thr Gly
130                 135                 140

Gly Gly Gly Ser Gly Gly Gly Ser Gly Ser Gly Ser Glu Ser Gly Ser
145                 150                 155                 160

Gly Gly Gly Ser Thr Ser Ser Gly Thr Gly Ser Glu Thr Glu Ser Pro
                165                 170                 175

Gly Ser Gly Ser Glu Ser Gly Ser Gly Pro Ser Ser Ala Gly Ser Gly
            180                 185                 190

Ser Gly Ser Glu Ser Gly Ser Gly Ser Ser Gly Pro Gly Ser
        195                 200                 205

Thr Gly Gly Ser Gly Ser Glu Ser Gly Ser Gly Pro Gly Ser Ser Gly
    210                 215                 220

Thr Gly Gly Thr Ala Thr Gly Ser Gly Ser Glu Ser Gly Ser Gly Pro
225                 230                 235                 240

Gly Ser Ser Gly Pro Gly Ser Thr Gly Ser Gly Ser Gly Ser Glu Ser
                245                 250                 255

Gly Ser Gly Ser Gly Ser Ser Gly Thr Gly Ser Thr Gly Ser Gly Ser
            260                 265                 270

Ser Glu Ser Gly Ser Gly Pro Gly Ser Pro Arg Pro Gly Ser Thr Gly
        275                 280                 285

Thr Gly Ser Gly Ser Glu Ser Gly Ser Gly Pro Gly Ser Ser Glu Arg
    290                 295                 300

Gly Ser Ala Gly Gly Ser Gly Ser Glu Ser Gly Ser Gly Thr Ser Glu
305                 310                 315                 320

Ser Ser Ala Ser Gly Ser Thr Gly Gly Ser Gly Glu Ser Gly Ser
            325                 330                 335

Gly Ser Glu Ser Gly Ser Gly Gly Ser Glu Ser Gly Ser Gly Pro
            340                 345                 350

Glu Ser Pro Gly Ser Gly Gly Ser Gly Glu Ser Gly Ser Gly Thr
            355                 360                 365

Ser Gly Ser Thr Gly Ser Gly Ser Glu Ser Gly Ser Gly Gly Ser
        370                 375                 380

Gly Gly Gly Ser Gly Gly Gly Ala Ser Ser Gly Val Arg Leu Trp Ala
385                 390                 395                 400

Thr Arg Gln Ala Met Leu Gly Gln Val His Glu Val Pro Glu Gly Trp
                405                 410                 415

Leu Ile Phe Val Ala Glu Gln Glu Leu Tyr Val Arg Val Gln Asn
                420                 425                 430

Gly Phe Arg Lys Val Gln Leu Glu Ala Arg Thr Pro Leu Pro Arg Gly
                435                 440                 445

<210> SEQ ID NO 15
<211> LENGTH: 448
<212> TYPE: PRT
<213> ORGANISM: Artificial Sequence
<220> FEATURE:
<223> OTHER INFORMATION: synthesized

<400> SEQUENCE: 15

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Ser Gly Ser
                20                  25                  30

Gly Gly Gly Ser Gly Gly Gly Ser Gly Gly Gly Ser Gly Gly Gly Ser
            35                  40                  45

Gly Ser Gly Gly Ala Val Pro Pro Thr Asp Leu Arg Phe Thr Asn
        50                  55                  60

Ile Gly Pro Asp Thr Met Arg Val Thr Trp Ala Pro Pro Ser Ile
65                  70                  75                  80

Asp Leu Thr Asn Phe Leu Val Arg Tyr Ser Pro Val Lys Asn Glu Glu
                85                  90                  95

Asp Val Ala Glu Leu Ser Ile Ser Pro Ser Asp Asn Ala Val Val Leu
                100                 105                 110

Thr Asn Leu Leu Pro Gly Thr Glu Tyr Val Val Ser Val Ser Ser Val
            115                 120                 125

Tyr Glu Gln His Glu Ser Thr Pro Leu Arg Gly Arg Gln Lys Thr Gly
        130                 135                 140

Gly Gly Gly Ser Gly Gly Gly Ser Gly Ser Glu Ser Gly Ser
145                 150                 155                 160

Gly Gly Gly Ser Thr Ser Ser Gly Thr Gly Ser Glu Thr Glu Ser Pro
                165                 170                 175

Gly Ser Gly Ser Glu Gly Ser Gly Pro Ser Ser Ala Gly Ser Gly
            180                 185                 190

Ser Gly Ser Glu Ser Gly Ser Gly Ser Gly Ser Gly Pro Gly Ser
        195                 200                 205

Thr Gly Gly Ser Gly Ser Glu Ser Gly Ser Gly Pro Gly Ser Ser Gly
            210                 215                 220

Thr Gly Gly Thr Ala Thr Gly Ser Gly Ser Glu Ser Gly Ser Gly Pro
225                 230                 235                 240

```
Gly Ser Ser Gly Pro Gly Ser Thr Gly Ser Gly Ser Gly Ser Glu Ser
                245                 250                 255

Gly Ser Gly Ser Gly Ser Ser Gly Thr Gly Ser Thr Gly Gly Ser Gly
            260                 265                 270

Ser Glu Ser Gly Ser Gly Pro Gly Ser Pro Arg Pro Gly Ser Thr Gly
        275                 280                 285

Thr Gly Ser Gly Ser Glu Ser Gly Ser Pro Gly Ser Ser Glu Arg
        290                 295                 300

Gly Ser Ala Gly Gly Gly Ser Glu Ser Ser Gly Thr Ser Glu
305                 310                 315                 320

Ser Ser Ala Ser Gly Ser Thr Gly Gly Ser Gly Ser Glu Ser Gly Ser
                325                 330                 335

Gly Ser Glu Ser Gly Ser Gly Ser Gly Ser Glu Ser Gly Ser Gly Pro
            340                 345                 350

Glu Ser Pro Gly Ser Gly Gly Ser Gly Ser Glu Ser Gly Ser Gly Thr
        355                 360                 365

Ser Gly Ser Thr Gly Ser Gly Ser Glu Ser Gly Ser Gly Gly Gly Ser
        370                 375                 380

Gly Gly Gly Ser Gly Gly Gly Ala Ser Ser Gly Val Arg Leu Trp Ala
385                 390                 395                 400

Thr Arg Gln Ala Met Leu Gly Gln Val His Glu Val Pro Glu Gly Trp
                405                 410                 415

Leu Ile Phe Val Ala Glu Gln Glu Glu Leu Tyr Val Arg Val Gln Asn
            420                 425                 430

Gly Phe Arg Lys Val Gln Leu Glu Ala Arg Thr Pro Leu Pro Arg Gly
        435                 440                 445

<210> SEQ ID NO 16
<211> LENGTH: 448
<212> TYPE: PRT
<213> ORGANISM: Artificial Sequence
<220> FEATURE:
<223> OTHER INFORMATION: synthesized

<400> SEQUENCE: 16

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly Ser
            20                  25                  30

Gly Gly Gly Ser Gly Gly Gly Ser Gly Gly Gly Ser Gly Gly Gly Ser
        35                  40                  45

Gly Ser Gly Gly Ala Val Pro Pro Thr Asp Leu Arg Phe Thr Asn
    50                  55                  60

Ile Gly Pro Asp Thr Met Arg Val Thr Trp Ala Pro Pro Pro Ser Ile
65                  70                  75                  80

Asp Leu Thr Asn Phe Leu Val Arg Tyr Ser Pro Val Lys Asn Glu Glu
                85                  90                  95

Asp Val Ala Glu Leu Ser Ile Ser Pro Ser Asp Asn Ala Val Val Leu
            100                 105                 110

Thr Asn Leu Leu Pro Gly Thr Glu Tyr Val Val Ser Val Ser Ser Val
        115                 120                 125

Tyr Glu Gln His Glu Ser Thr Pro Leu Arg Gly Arg Gln Lys Thr Gly
    130                 135                 140

Gly Gly Gly Ser Gly Gly Gly Ser Gly Ser Glu Ser Gly Ser
145                 150                 155                 160
```

Gly Gly Gly Ser Thr Ser Ser Gly Thr Ser Glu Thr Glu Ser Pro
            165                 170                 175

Gly Ser Gly Ser Glu Ser Gly Ser Gly Pro Ser Ser Ala Gly Ser Gly
            180                 185                 190

Ser Gly Ser Glu Ser Gly Ser Gly Ser Ser Gly Pro Gly Ser
            195                 200                 205

Thr Gly Gly Ser Gly Ser Glu Ser Gly Ser Gly Pro Gly Ser Ser Gly
            210                 215                 220

Thr Gly Gly Thr Ala Thr Gly Ser Ser Glu Ser Gly Ser Gly Pro
225                 230                 235                 240

Gly Ser Ser Gly Pro Gly Ser Thr Gly Ser Gly Ser Gly Ser Glu Ser
            245                 250                 255

Gly Ser Gly Ser Gly Ser Ser Gly Thr Gly Ser Thr Gly Gly Ser Gly
            260                 265                 270

Ser Glu Ser Gly Ser Gly Pro Gly Ser Pro Arg Pro Gly Ser Thr Gly
            275                 280                 285

Thr Gly Ser Gly Ser Glu Ser Gly Ser Gly Pro Gly Ser Ser Glu Arg
            290                 295                 300

Gly Ser Ala Gly Gly Ser Gly Ser Glu Ser Gly Ser Gly Thr Ser Glu
305                 310                 315                 320

Ser Ser Ala Ser Gly Ser Thr Gly Gly Ser Gly Ser Glu Ser Gly Ser
            325                 330                 335

Gly Ser Glu Ser Gly Ser Gly Ser Ser Glu Ser Gly Ser Gly Pro
            340                 345                 350

Glu Ser Pro Gly Ser Gly Gly Ser Glu Ser Gly Ser Gly Thr
            355                 360                 365

Ser Gly Ser Thr Gly Ser Gly Ser Glu Ser Gly Ser Gly Gly Ser
            370                 375                 380

Gly Gly Gly Ser Gly Gly Gly Ala Ser Ser Gly Val Arg Leu Trp Ala
385                 390                 395                 400

Thr Arg Gln Ala Met Leu Gly Gln Val His Glu Val Pro Glu Gly Trp
            405                 410                 415

Leu Ile Phe Val Ala Glu Gln Glu Glu Leu Tyr Val Arg Val Gln Asn
            420                 425                 430

Gly Phe Arg Lys Val Gln Leu Glu Ala Arg Thr Pro Leu Pro Arg Gly
            435                 440                 445

<210> SEQ ID NO 17
<211> LENGTH: 447
<212> TYPE: PRT
<213> ORGANISM: Artificial Sequence
<220> FEATURE:
<223> OTHER INFORMATION: synthesized

<400> SEQUENCE: 17

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly Ser
            20                  25                  30

Gly Gly Gly Ser Gly Gly Gly Ser Gly Gly Gly Ser Gly Gly Gly Ser
            35                  40                  45

Gly Ser Gly Gly Arg Leu Asp Ala Pro Ser Gln Ile Glu Val Lys Asp
        50                  55                  60

Val Thr Asp Thr Thr Ala Leu Ile Thr Trp Phe Lys Pro Leu Ala Glu
65                  70                  75                  80

Ile Asp Gly Ile Glu Leu Thr Tyr Gly Ile Lys Asp Val Pro Gly Asp
                 85                  90                  95

Arg Thr Thr Ile Asp Leu Thr Glu Asp Glu Asn Gln Tyr Ser Ile Gly
            100                 105                 110

Asn Leu Lys Pro Asp Thr Glu Tyr Glu Val Ser Leu Ile Ser Arg Arg
        115                 120                 125

Gly Asp Met Ser Ser Asn Pro Ala Lys Glu Thr Phe Thr Thr Gly Gly
    130                 135                 140

Gly Gly Ser Gly Gly Ser Gly Ser Gly Ser Glu Ser Gly Ser Gly Gly
145                 150                 155                 160

Gly Gly Ser Thr Ser Gly Thr Gly Ser Glu Thr Glu Ser Pro Gly
                165                 170                 175

Ser Gly Ser Glu Ser Gly Ser Gly Pro Ser Ala Gly Ser Gly Ser
                180                 185                 190

Gly Ser Glu Ser Gly Ser Gly Ser Ser Gly Pro Gly Ser Thr
            195                 200                 205

Gly Gly Ser Gly Ser Glu Ser Gly Ser Gly Pro Gly Ser Ser Gly Thr
    210                 215                 220

Gly Gly Thr Ala Thr Gly Ser Gly Ser Glu Ser Gly Ser Gly Pro Gly
225                 230                 235                 240

Ser Ser Gly Pro Gly Ser Thr Gly Ser Gly Ser Glu Ser Gly
                245                 250                 255

Ser Gly Ser Gly Ser Ser Gly Thr Gly Ser Thr Gly Ser Gly Ser
        260                 265                 270

Glu Ser Gly Ser Gly Pro Gly Ser Pro Arg Pro Gly Ser Thr Gly Thr
        275                 280                 285

Gly Ser Gly Ser Glu Ser Gly Ser Gly Pro Gly Ser Ser Glu Arg Gly
    290                 295                 300

Ser Ala Gly Gly Ser Gly Ser Glu Ser Gly Ser Gly Thr Ser Glu Ser
305                 310                 315                 320

Ser Ala Ser Gly Ser Thr Gly Ser Gly Ser Glu Ser Gly Ser Gly
                325                 330                 335

Ser Glu Ser Gly Ser Gly Ser Gly Ser Glu Ser Gly Ser Gly Pro Glu
        340                 345                 350

Ser Pro Gly Ser Gly Gly Ser Gly Ser Glu Ser Gly Ser Gly Thr Ser
        355                 360                 365

Gly Ser Thr Gly Ser Gly Ser Glu Ser Gly Ser Gly Gly Gly Ser Gly
    370                 375                 380

Gly Gly Ser Gly Gly Gly Ala Ser Ser Gly Val Arg Leu Trp Ala Thr
385                 390                 395                 400

Arg Gln Ala Met Leu Gly Gln Val His Glu Val Pro Glu Gly Trp Leu
            405                 410                 415

Ile Phe Val Ala Glu Gln Glu Leu Tyr Val Arg Val Gln Asn Gly
            420                 425                 430

Phe Arg Lys Val Gln Leu Glu Ala Arg Thr Pro Leu Pro Arg Gly
        435                 440                 445

<210> SEQ ID NO 18
<211> LENGTH: 444
<212> TYPE: PRT
<213> ORGANISM: Artificial Sequence
<220> FEATURE:
<223> OTHER INFORMATION: synthesized

<400> SEQUENCE: 18

```
His Gly Glu Gly Thr Phe Thr Ser Asp Val Ser Ser Tyr Leu Glu Glu
 1               5                  10                 15

Gln Ala Ala Lys Glu Phe Ile Ala Trp Leu Val Lys Gly Gly Gly Ser
             20                  25                 30

Gly Gly Gly Ser Gly Gly Gly Ser Gly Gly Gly Ser Gly Gly Gly Ser
             35                  40                 45

Gly Ser Gly Gly Ala Val Pro Pro Thr Asp Leu Arg Phe Thr Asn
 50              55                  60

Ile Gly Pro Asp Thr Met Arg Val Thr Trp Ala Pro Pro Ser Ile
 65              70                  75                  80

Asp Leu Thr Asn Phe Leu Val Arg Tyr Ser Pro Val Lys Asn Glu Glu
                 85                  90                  95

Asp Val Ala Glu Leu Ser Ile Ser Pro Ser Asp Asn Ala Val Val Leu
            100                 105                 110

Thr Asn Leu Leu Pro Gly Thr Glu Tyr Val Val Ser Val Ser Ser Val
            115                 120                 125

Tyr Glu Gln His Glu Ser Thr Pro Leu Arg Gly Arg Gln Lys Thr Gly
    130                 135                 140

Gly Gly Gly Ser Gly Gly Ser Gly Ser Gly Ser Glu Ser Gly Ser
145                 150                 155                 160

Gly Gly Gly Ser Thr Ser Ser Gly Thr Gly Ser Glu Thr Glu Ser Pro
                165                 170                 175

Gly Ser Gly Ser Glu Ser Gly Ser Pro Ser Ser Ala Gly Ser Gly
                180                 185                 190

Ser Gly Ser Glu Ser Gly Ser Gly Ser Ser Gly Pro Gly Ser
                195                 200                 205

Thr Gly Gly Ser Gly Ser Glu Ser Gly Ser Gly Pro Gly Ser Ser Gly
210                 215                 220

Thr Gly Gly Thr Ala Thr Gly Ser Ser Glu Ser Gly Ser Gly Pro
225                 230                 235                 240

Gly Ser Ser Gly Pro Gly Ser Thr Gly Ser Gly Ser Ser Glu Ser
                245                 250                 255

Gly Ser Gly Ser Gly Ser Ser Gly Thr Gly Ser Thr Gly Gly Ser Gly
                260                 265                 270

Ser Glu Ser Gly Ser Gly Pro Gly Ser Pro Arg Pro Gly Ser Thr Gly
    275                 280                 285

Thr Gly Ser Gly Ser Glu Ser Gly Ser Gly Pro Gly Ser Ser Glu Arg
    290                 295                 300

Gly Ser Ala Gly Gly Ser Gly Ser Glu Ser Gly Ser Gly Thr Ser Glu
305                 310                 315                 320

Ser Ser Ala Ser Gly Ser Thr Gly Gly Ser Gly Ser Glu Ser Gly Ser
                325                 330                 335

Gly Ser Glu Ser Gly Ser Gly Ser Gly Ser Glu Ser Gly Ser Gly Pro
                340                 345                 350

Glu Ser Pro Gly Ser Gly Gly Ser Gly Ser Glu Ser Gly Ser Gly Thr
    355                 360                 365

Ser Gly Ser Thr Gly Ser Gly Ser Glu Ser Gly Ser Gly Gly Gly Ser
    370                 375                 380

Gly Gly Gly Ser Gly Gly Asn Leu Val Thr Ala Phe Ser Asn Met Asp
385                 390                 395                 400

Asp Met Leu Gln Lys Ala His Leu Val Ile Glu Gly Thr Phe Ile Tyr
                405                 410                 415

Leu Arg Asp Ser Thr Glu Phe Phe Ile Arg Val Arg Asp Gly Trp Lys
```

```
            420                 425                 430
Lys Leu Gln Leu Gly Glu Leu Ile Pro Ile Pro Ala
        435                 440

<210> SEQ ID NO 19
<211> LENGTH: 440
<212> TYPE: PRT
<213> ORGANISM: Artificial Sequence
<220> FEATURE:
<223> OTHER INFORMATION: synthesized

<400> SEQUENCE: 19

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly Ser
            20                  25                  30

Gly Gly Gly Ser Gly Gly Gly Ser Gly Gly Gly Ser Gly Gly Gly Ser
        35                  40                  45

Gly Ser Gly Gly Ala Val Pro Pro Thr Asp Leu Arg Phe Thr Asn
    50                  55                  60

Ile Gly Pro Asp Thr Met Arg Val Thr Trp Ala Pro Pro Ser Ile
65                  70                  75                  80

Asp Leu Thr Asn Phe Leu Val Arg Tyr Ser Pro Val Lys Asn Glu Glu
                85                  90                  95

Asp Val Ala Glu Leu Ser Ile Ser Pro Ser Asp Asn Ala Val Val Leu
            100                 105                 110

Thr Asn Leu Leu Pro Gly Thr Glu Tyr Val Val Ser Val Ser Ser Val
        115                 120                 125

Tyr Glu Gln His Glu Ser Thr Pro Leu Arg Gly Arg Gln Lys Thr Gly
    130                 135                 140

Gly Gly Gly Ser Gly Gly Gly Ser Gly Ser Gly Glu Ser Gly Ser
145                 150                 155                 160

Gly Gly Gly Ser Thr Ser Ser Gly Thr Gly Ser Glu Thr Glu Ser Pro
                165                 170                 175

Gly Ser Gly Ser Glu Ser Gly Ser Gly Pro Ser Ser Ala Gly Ser Gly
            180                 185                 190

Ser Gly Ser Glu Ser Gly Ser Gly Ser Ser Gly Pro Gly Ser
        195                 200                 205

Thr Gly Gly Ser Gly Ser Glu Ser Gly Ser Gly Pro Gly Ser Ser Gly
    210                 215                 220

Thr Gly Gly Thr Ala Thr Gly Ser Gly Ser Glu Ser Gly Ser Gly Pro
225                 230                 235                 240

Gly Ser Ser Gly Pro Gly Ser Thr Gly Ser Gly Ser Gly Glu Ser
                245                 250                 255

Gly Ser Gly Ser Gly Ser Ser Gly Thr Gly Ser Thr Gly Gly Ser Gly
            260                 265                 270

Ser Glu Ser Gly Ser Gly Pro Gly Ser Pro Arg Pro Gly Ser Thr Gly
        275                 280                 285

Thr Gly Ser Gly Ser Glu Ser Gly Ser Gly Pro Gly Ser Ser Glu Arg
    290                 295                 300

Gly Ser Ala Gly Gly Gly Ser Gly Glu Ser Ser Gly Thr Ser Glu
305                 310                 315                 320

Ser Ser Ala Ser Gly Ser Thr Gly Gly Ser Gly Ser Glu Ser Gly Ser
                325                 330                 335

Gly Ser Glu Ser Gly Ser Gly Ser Gly Ser Glu Ser Gly Ser Gly Pro
```

```
                340                 345                 350
Glu Ser Pro Gly Ser Gly Gly Ser Gly Ser Glu Ser Gly Gly Thr
            355                 360                 365

Ser Gly Ser Thr Gly Ser Gly Ser Glu Ser Gly Ser Gly Gly Ser
370                 375                 380

Gly Gly Gly Ser Gly Gly Gly Ile Pro Ala Asp Ala Val Ser Phe Glu
385                 390                 395                 400

Glu Ile Lys Lys Tyr Ile Asn Gln Glu Val Leu Arg Ile Phe Glu Glu
                405                 410                 415

Arg Met Ala Val Phe Leu Ser Gln Leu Lys Leu Pro Ala Ala Met Leu
            420                 425                 430

Ala Ala Gln Ala Tyr Gly Arg Pro
            435                 440

<210> SEQ ID NO 20
<211> LENGTH: 525
<212> TYPE: PRT
<213> ORGANISM: Artificial Sequence
<220> FEATURE:
<223> OTHER INFORMATION: synthesized

<400> SEQUENCE: 20

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly Ser
                20                  25                  30

Gly Gly Gly Ser Gly Gly Gly Ser Gly Gly Ser Gly Gly Gly Ser
            35                  40                  45

Gly Ser Gly Gly Ala Val Pro Pro Pro Thr Asp Leu Arg Phe Thr Asn
50                  55                  60

Ile Gly Pro Asp Thr Met Arg Val Thr Trp Ala Pro Pro Pro Ser Ile
65                  70                  75                  80

Asp Leu Thr Asn Phe Leu Val Arg Tyr Ser Pro Val Lys Asn Glu Glu
                85                  90                  95

Asp Val Ala Glu Leu Ser Ile Ser Pro Ser Asp Asn Ala Val Val Leu
            100                 105                 110

Thr Asn Leu Leu Pro Gly Thr Glu Tyr Val Val Ser Val Ser Ser Val
        115                 120                 125

Tyr Glu Gln His Glu Ser Thr Pro Leu Arg Gly Arg Gln Lys Thr Gly
            130                 135                 140

Gly Gly Gly Ser Gly Gly Gly Ser Gly Ser Glu Ser Gly Ser
145                 150                 155                 160

Gly Gly Gly Ser Thr Ser Ser Gly Thr Gly Ser Glu Thr Glu Ser Pro
                165                 170                 175

Gly Ser Gly Ser Glu Ser Gly Ser Gly Pro Ser Ser Ala Gly Ser Gly
            180                 185                 190

Ser Gly Ser Glu Ser Gly Ser Gly Ser Ser Gly Pro Gly Ser
        195                 200                 205

Thr Gly Gly Ser Gly Ser Glu Ser Gly Ser Gly Pro Gly Ser Ser Gly
    210                 215                 220

Thr Gly Gly Thr Ala Thr Gly Ser Gly Ser Glu Ser Gly Ser Gly Pro
225                 230                 235                 240

Gly Ser Ser Gly Pro Gly Ser Thr Gly Ser Gly Ser Gly Ser Glu Ser
                245                 250                 255

Gly Ser Gly Ser Gly Ser Ser Gly Thr Gly Ser Thr Gly Ser Gly
```

```
                260                 265                 270
Ser Glu Ser Gly Ser Gly Pro Gly Ser Pro Arg Pro Gly Ser Thr Gly
            275                 280                 285

Thr Gly Ser Gly Ser Glu Ser Gly Ser Gly Pro Gly Ser Ser Glu Arg
        290                 295                 300

Gly Ser Ala Gly Gly Ser Gly Ser Glu Ser Gly Ser Gly Thr Ser Glu
305                 310                 315                 320

Ser Ser Ala Ser Gly Ser Thr Gly Gly Ser Gly Ser Glu Ser Gly Ser
            325                 330                 335

Gly Ser Glu Ser Gly Ser Gly Ser Gly Ser Glu Ser Gly Ser Gly Pro
        340                 345                 350

Glu Ser Pro Gly Ser Gly Ser Gly Ser Glu Ser Gly Ser Gly Thr
        355                 360                 365

Ser Gly Ser Thr Gly Ser Gly Glu Ser Gly Ser Gly Gly Gly Ser
        370                 375                 380

Gly Gly Gly Ser Gly Gly Val Tyr Arg Ser Ala Phe Ser Val Gly Leu
385                 390                 395                 400

Glu Thr Arg Val Thr Val Pro Asn Val Pro Ile Arg Phe Thr Lys Ile
                405                 410                 415

Phe Tyr Asn Gln Gln Asn His Tyr Asp Gly Ser Thr Gly Lys Phe Tyr
            420                 425                 430

Cys Asn Ile Pro Gly Leu Tyr Tyr Phe Ser Tyr His Ile Thr Val Tyr
            435                 440                 445

Met Lys Asp Val Lys Val Ser Leu Phe Lys Lys Asp Lys Ala Val Leu
        450                 455                 460

Phe Thr Tyr Asp Gln Tyr Gln Glu Lys Asn Val Asp Gln Ala Ser Gly
465                 470                 475                 480

Ser Val Leu Leu His Leu Glu Val Gly Asp Gln Val Trp Leu Gln Val
            485                 490                 495

Tyr Gly Asp Gly Asp His Asn Gly Leu Tyr Ala Asp Asn Val Asn Asp
        500                 505                 510

Ser Thr Phe Thr Gly Phe Leu Leu Tyr His Asp Thr Asn
        515                 520                 525

<210> SEQ ID NO 21
<211> LENGTH: 447
<212> TYPE: PRT
<213> ORGANISM: Artificial Sequence
<220> FEATURE:
<223> OTHER INFORMATION: synthesized

<400> SEQUENCE: 21

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly Ser
            20                  25                  30

Gly Gly Gly Ser Gly Gly Gly Ser Gly Gly Gly Ser Gly Gly Gly Ser
        35                  40                  45

Gly Ser Gly Gly Ala Val Pro Pro Pro Thr Asp Leu Arg Phe Thr Asn
50                  55                  60

Ile Gly Pro Asp Thr Met Arg Val Thr Trp Ala Pro Pro Pro Ser Ile
65                  70                  75                  80

Asp Leu Thr Asn Phe Leu Val Arg Tyr Ser Pro Val Lys Asn Glu Glu
            85                  90                  95

Asp Val Ala Glu Leu Ser Ile Ser Pro Ser Asp Asn Ala Val Val Leu
```

```
            100                 105                 110
Thr Asn Leu Leu Pro Gly Thr Glu Tyr Val Ser Val Ser Ser Val
        115                 120                 125

Tyr Glu Gln His Glu Ser Thr Pro Leu Arg Gly Arg Gln Lys Thr Gly
        130                 135                 140

Gly Gly Gly Ser Gly Gly Gly Ser Gly Ser Gly Ser Thr Ser Glu Ser
145                 150                 155                 160

Gly Gly Ser Thr Ser Ser Gly Thr Gly Ser Glu Thr Glu Ser Pro Gly
                165                 170                 175

Ser Gly Ser Glu Ser Thr Ser Gly Pro Ser Ser Ala Gly Ser Gly Ser
                180                 185                 190

Thr Ser Glu Ser Gly Ser Gly Ser Ser Ser Gly Pro Gly Ser Thr
        195                 200                 205

Gly Gly Ser Thr Ser Gly Ser Glu Ser Gly Pro Gly Ser Ser Gly Thr
        210                 215                 220

Gly Gly Thr Ala Thr Gly Ser Glu Ser Gly Ser Thr Ser Gly Pro Gly
225                 230                 235                 240

Ser Ser Gly Pro Gly Ser Thr Gly Ser Gly Ser Thr Ser Glu Ser Gly
                245                 250                 255

Ser Gly Ser Gly Ser Ser Gly Thr Gly Ser Thr Gly Gly Ser Glu Ser
                260                 265                 270

Gly Ser Thr Ser Gly Pro Gly Ser Pro Arg Pro Gly Ser Thr Gly Thr
                275                 280                 285

Gly Ser Thr Ser Gly Ser Glu Ser Gly Pro Gly Ser Ser Glu Arg Gly
        290                 295                 300

Ser Ala Gly Gly Ser Glu Ser Thr Ser Gly Ser Gly Thr Ser Glu Ser
305                 310                 315                 320

Ser Ala Ser Gly Ser Thr Gly Gly Ser Thr Ser Gly Ser Glu Ser Gly
                325                 330                 335

Ser Glu Ser Gly Ser Gly Ser Thr Ser Glu Ser Gly Ser Gly Pro Glu
                340                 345                 350

Ser Pro Gly Ser Gly Gly Ser Gly Ser Thr Ser Glu Ser Gly Thr Ser
                355                 360                 365

Gly Ser Thr Gly Ser Glu Ser Thr Ser Gly Ser Gly Gly Gly Ser Gly
        370                 375                 380

Gly Gly Ser Gly Gly Gly Ala Ser Ser Gly Val Arg Leu Trp Ala Thr
385                 390                 395                 400

Arg Gln Ala Met Leu Gly Gln Val His Glu Val Pro Glu Gly Trp Leu
                405                 410                 415

Ile Phe Val Ala Glu Gln Glu Leu Tyr Val Arg Val Gln Asn Gly
                420                 425                 430

Phe Arg Lys Val Gln Leu Glu Ala Arg Thr Pro Leu Pro Arg Gly
        435                 440                 445

<210> SEQ ID NO 22
<211> LENGTH: 473
<212> TYPE: PRT
<213> ORGANISM: Artificial Sequence
<220> FEATURE:
<223> OTHER INFORMATION: synthesized

<400> SEQUENCE: 22

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly Ser
```

```
                    20                  25                  30
Gly Gly Gly Ser Gly Gly Ser Gly Gly Ser Gly Gly Ser
                35                  40                  45
Gly Ser Gly Gly Ala Val Pro Pro Thr Asp Leu Arg Phe Thr Asn
            50                  55                  60
Ile Gly Pro Asp Thr Met Arg Val Thr Trp Ala Pro Pro Ser Ile
 65                 70                  75                  80
Asp Leu Thr Asn Phe Leu Val Arg Tyr Ser Pro Val Lys Asn Glu Glu
                85                  90                  95
Asp Val Ala Glu Leu Ser Ile Ser Pro Ser Asp Asn Ala Val Val Leu
            100                 105                 110
Thr Asn Leu Leu Pro Gly Thr Glu Tyr Val Val Ser Val Ser Ser Val
            115                 120                 125
Tyr Glu Gln His Glu Ser Thr Pro Leu Arg Gly Arg Gln Lys Thr Gly
            130                 135                 140
Gly Gly Gly Ser Gly Gly Ser Gly Gly Ser Gly Ser Glu Ser Gly
145                 150                 155                 160
Ser Gly Gly Ser Thr Ser Ser Gly Thr Gly Ser Glu Thr Glu Ser
                165                 170                 175
Pro Gly Gly Ser Gly Ser Glu Ser Gly Ser Gly Pro Ser Ser Ala
            180                 185                 190
Gly Ser Gly Gly Ser Gly Ser Glu Ser Gly Ser Gly Ser Gly Ser
            195                 200                 205
Ser Gly Pro Gly Ser Thr Gly Gly Ser Gly Ser Glu Ser Gly Ser
            210                 215                 220
Gly Gly Pro Gly Ser Ser Gly Thr Gly Thr Ala Thr Gly Gly Ser
225                 230                 235                 240
Gly Ser Glu Ser Gly Ser Gly Pro Gly Ser Ser Gly Pro Gly Ser
                245                 250                 255
Thr Gly Ser Gly Gly Ser Gly Ser Glu Ser Gly Ser Gly Gly Ser Gly
                260                 265                 270
Ser Ser Gly Thr Gly Ser Thr Gly Gly Ser Gly Ser Glu Ser Gly
            275                 280                 285
Ser Gly Gly Pro Gly Ser Pro Arg Pro Gly Ser Thr Gly Thr Gly
            290                 295                 300
Ser Gly Ser Glu Ser Gly Ser Gly Gly Pro Gly Ser Glu Arg Gly
305                 310                 315                 320
Ser Ala Gly Gly Ser Gly Ser Glu Ser Gly Ser Gly Gly Thr Ser
                325                 330                 335
Glu Ser Ser Ala Ser Gly Ser Thr Gly Gly Ser Gly Ser Glu Ser
            340                 345                 350
Gly Ser Gly Ser Glu Ser Gly Ser Gly Ser Gly Ser Glu Ser
            355                 360                 365
Gly Ser Gly Gly Pro Glu Ser Pro Gly Ser Gly Gly Ser Gly Ser
            370                 375                 380
Glu Ser Gly Ser Gly Gly Thr Ser Gly Ser Thr Gly Gly Ser Gly Ser
385                 390                 395                 400
Glu Ser Gly Ser Gly Gly Gly Ser Gly Gly Ser Gly Gly Gly
                405                 410                 415
Ala Ser Ser Gly Val Arg Leu Trp Ala Thr Arg Gln Ala Met Leu Gly
            420                 425                 430
Gln Val His Glu Val Pro Glu Gly Trp Leu Ile Phe Val Ala Glu Gln
            435                 440                 445
```

```
Glu Glu Leu Tyr Val Arg Val Gln Asn Gly Phe Arg Lys Val Gln Leu
            450                 455                 460

Glu Ala Arg Thr Pro Leu Pro Arg Gly
465                 470

<210> SEQ ID NO 23
<211> LENGTH: 487
<212> TYPE: PRT
<213> ORGANISM: Artificial Sequence
<220> FEATURE:
<223> OTHER INFORMATION: synthesized

<400> SEQUENCE: 23

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly Ser
            20                  25                  30

Gly Gly Gly Ser Gly Gly Gly Ser Gly Gly Gly Ser Gly Gly Gly Ser
        35                  40                  45

Gly Ser Gly Gly Ala Val Pro Pro Thr Asp Leu Arg Phe Thr Asn
    50                  55                  60

Ile Gly Pro Asp Thr Met Arg Val Thr Trp Ala Pro Pro Ser Ile
65                  70                  75                  80

Asp Leu Thr Asn Phe Leu Val Arg Tyr Ser Pro Val Lys Asn Glu Glu
                85                  90                  95

Asp Val Ala Glu Leu Ser Ile Ser Pro Ser Asp Asn Ala Val Val Leu
            100                 105                 110

Thr Asn Leu Leu Pro Gly Thr Glu Tyr Val Val Ser Val Ser Ser Val
        115                 120                 125

Tyr Glu Gln His Glu Ser Thr Pro Leu Arg Gly Arg Gln Lys Thr Gly
    130                 135                 140

Gly Gly Gly Ser Gly Gly Gly Ser Gly Ser Gly Ser Glu Ser Gly Ser
145                 150                 155                 160

Gly Gly Gly Ser Thr Ser Ser Gly Thr Gly Ser Glu Thr Glu Ser Pro
                165                 170                 175

Gly Ser Gly Ser Glu Ser Gly Ser Gly Pro Ser Ser Ala Gly Ser Gly
            180                 185                 190

Ser Gly Ser Glu Ser Gly Ser Gly Ser Ser Gly Pro Gly Ser
        195                 200                 205

Thr Gly Gly Ser Gly Ser Glu Ser Gly Ser Pro Gly Ser Ser Gly
    210                 215                 220

Thr Gly Thr Ala Thr Gly Ser Gly Ser Glu Ser Gly Ser Gly Pro
225                 230                 235                 240

Gly Ser Ser Gly Pro Gly Ser Thr Gly Ser Gly Ser Gly Ser Glu Ser
                245                 250                 255

Gly Ser Gly Ser Gly Ser Ser Gly Thr Gly Ser Thr Gly Gly Ser Gly
            260                 265                 270

Ser Glu Ser Gly Ser Gly Pro Gly Ser Pro Arg Pro Gly Ser Thr Gly
        275                 280                 285

Thr Gly Ser Gly Ser Glu Ser Gly Ser Gly Pro Gly Ser Ser Glu Arg
    290                 295                 300

Gly Ser Ala Gly Gly Ser Gly Ser Glu Ser Gly Ser Gly Thr Ser Glu
305                 310                 315                 320

Ser Ser Ala Ser Gly Ser Thr Gly Gly Ser Gly Ser Glu Ser Gly Ser
                325                 330                 335
```

-continued

Gly Ser Glu Ser Gly Ser Gly Ser Glu Ser Gly Ser Gly Pro
              340                 345                 350

Glu Ser Pro Gly Ser Gly Gly Ser Gly Glu Ser Gly Ser Gly Thr
          355                 360                 365

Ser Gly Ser Thr Gly Ser Gly Glu Ser Gly Ser Gly Pro Gly Ser
370                 375                 380

Ser Gly Pro Gly Ser Thr Gly Ser Gly Ser Glu Ser Gly Ser
385                 390                 395                 400

Gly Ser Gly Ser Ser Gly Thr Gly Ser Thr Gly Gly Ser Gly Ser Glu
                405                 410                 415

Ser Gly Ser Gly Gly Ser Gly Gly Gly Ser Gly Gly Ala Ser
              420                 425                 430

Ser Gly Val Arg Leu Trp Ala Thr Arg Gln Ala Met Leu Gly Gln Val
              435                 440                 445

His Glu Val Pro Glu Gly Trp Leu Ile Phe Val Ala Glu Gln Glu Glu
              450                 455                 460

Leu Tyr Val Arg Val Gln Asn Gly Phe Arg Lys Val Gln Leu Glu Ala
465                 470                 475                 480

Arg Thr Pro Leu Pro Arg Gly
                485

<210> SEQ ID NO 24
<211> LENGTH: 469
<212> TYPE: PRT
<213> ORGANISM: Artificial Sequence
<220> FEATURE:
<223> OTHER INFORMATION: synthesized

<400> SEQUENCE: 24

Cys Asp Leu Pro Gln Thr His Ser Leu Gly Ser Arg Arg Thr Leu Met
1               5                   10                  15

Leu Leu Ala Gln Met Arg Arg Ile Ser Leu Phe Ser Cys Leu Lys Asp
              20                  25                  30

Arg His Asp Phe Gly Phe Pro Gln Glu Glu Phe Gly Asn Gln Phe Gln
          35                  40                  45

Lys Ala Glu Thr Ile Pro Val Leu His Glu Met Ile Gln Gln Ile Phe
    50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
              85                  90                  95

Ala Cys Val Ile Gln Gly Val Gly Val Thr Glu Thr Pro Leu Met Asn
          100                 105                 110

Glu Asp Ser Ile Leu Ala Val Arg Lys Tyr Phe Gln Arg Ile Thr Leu
      115                 120                 125

Tyr Leu Lys Glu Lys Lys Tyr Ser Pro Cys Ala Trp Glu Val Val Arg
130                 135                 140

Ala Glu Ile Met Arg Ser Phe Ser Leu Ser Thr Asn Leu Gln Glu Ser
145                 150                 155                 160

Leu Arg Ser Lys Glu Gly Gly Ser Gly Gly Gly Ser Gly Ser Gly
              165                 170                 175

Ser Glu Ser Gly Ser Gly Gly Ser Gly Thr Ser Ser Gly Thr Gly Ser
          180                 185                 190

Glu Thr Glu Ser Pro Gly Ser Gly Ser Glu Ser Gly Ser Gly Pro Ser
      195                 200                 205

Ser Ala Gly Ser Gly Ser Glu Ser Gly Ser Gly Ser
    210             215             220

Ser Gly Pro Gly Ser Thr Gly Gly Ser Glu Ser Gly Ser Gly
225             230             235             240

Pro Gly Ser Ser Gly Thr Gly Thr Ala Thr Gly Gly Ser Glu
            245             250             255

Ser Gly Ser Gly Pro Gly Ser Ser Gly Pro Gly Ser Thr Gly Ser Gly
            260             265             270

Ser Gly Ser Glu Ser Gly Ser Gly Ser Ser Gly Thr Gly Ser
    275             280             285

Thr Gly Gly Ser Gly Ser Glu Ser Gly Ser Gly Pro Gly Ser Pro Arg
290             295             300

Pro Gly Ser Thr Gly Thr Gly Ser Gly Ser Glu Ser Gly Ser Gly Pro
305             310             315             320

Gly Ser Ser Glu Arg Gly Ser Ala Gly Gly Ser Gly Ser Glu Ser Gly
            325             330             335

Ser Gly Thr Ser Glu Ser Ser Ala Ser Gly Ser Thr Gly Gly Ser Gly
            340             345             350

Ser Glu Ser Gly Ser Gly Ser Glu Ser Gly Ser Gly Gly Ser Glu
    355             360             365

Ser Gly Ser Gly Pro Glu Ser Pro Gly Ser Gly Gly Ser Gly Ser Glu
    370             375             380

Ser Gly Ser Gly Thr Ser Gly Ser Thr Gly Gly Ser Glu Ser Gly
385             390             395             400

Ser Gly Gly Gly Ser Gly Gly Gly Ser Gly Gly Ala Ser Ser Gly
            405             410             415

Val Arg Leu Trp Ala Thr Arg Gln Ala Met Leu Gly Gln Val His Glu
            420             425             430

Val Pro Glu Gly Trp Leu Ile Phe Val Ala Glu Gln Glu Leu Tyr
    435             440             445

Val Arg Val Gln Asn Gly Phe Arg Lys Val Gln Leu Glu Ala Arg Thr
450             455             460

Pro Leu Pro Arg Gly
465

<210> SEQ ID NO 25
<211> LENGTH: 494
<212> TYPE: PRT
<213> ORGANISM: Artificial Sequence
<220> FEATURE:
<223> OTHER INFORMATION: synthesized

<400> SEQUENCE: 25

Cys Asp Leu Pro Gln Thr His Ser Leu Gly Ser Arg Arg Thr Leu Met
1               5                   10                  15

Leu Leu Ala Gln Met Arg Arg Ile Ser Leu Phe Ser Cys Leu Lys Asp
            20                  25                  30

Arg His Asp Phe Gly Phe Pro Gln Glu Glu Phe Gly Asn Gln Phe Gln
        35                  40                  45

Lys Ala Glu Thr Ile Pro Val Leu His Glu Met Ile Gln Gln Ile Phe
    50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

```
Ala Cys Val Ile Gln Gly Val Gly Val Thr Glu Thr Pro Leu Met Asn
                100             105             110

Glu Asp Ser Ile Leu Ala Val Arg Lys Tyr Phe Gln Arg Ile Thr Leu
            115             120             125

Tyr Leu Lys Glu Lys Tyr Ser Pro Cys Ala Trp Glu Val Val Arg
        130             135             140

Ala Glu Ile Met Arg Ser Phe Ser Leu Ser Thr Asn Leu Gln Glu Ser
145             150             155             160

Leu Arg Ser Lys Glu Gly Gly Ser Gly Gly Ser Gly Gly Ser
            165             170             175

Gly Ser Glu Ser Gly Gly Gly Ser Thr Ser Gly Thr Gly
            180             185             190

Ser Glu Thr Glu Ser Pro Gly Gly Ser Gly Ser Glu Ser Gly Ser Gly
            195             200             205

Gly Pro Ser Ser Ala Gly Ser Gly Gly Ser Gly Ser Glu Ser Gly Ser
            210             215             220

Gly Gly Ser Gly Ser Ser Gly Pro Gly Ser Thr Gly Gly Gly Ser Gly
225             230             235             240

Ser Glu Ser Gly Ser Gly Gly Pro Gly Ser Ser Gly Thr Gly Thr
            245             250             255

Ala Thr Gly Gly Ser Gly Ser Glu Ser Gly Ser Gly Gly Pro Gly Ser
            260             265             270

Ser Gly Pro Gly Ser Thr Gly Ser Gly Gly Gly Ser Glu Ser Gly
            275             280             285

Ser Gly Gly Ser Gly Ser Gly Thr Gly Ser Thr Gly Gly Gly Ser
            290             295             300

Gly Ser Glu Ser Gly Ser Gly Pro Gly Ser Pro Arg Pro Gly Ser
305             310             315             320

Thr Gly Thr Gly Gly Ser Gly Ser Glu Ser Gly Ser Gly Gly Pro Gly
            325             330             335

Ser Ser Glu Arg Gly Ser Ala Gly Gly Gly Ser Gly Ser Glu Ser Gly
            340             345             350

Ser Gly Gly Thr Ser Glu Ser Ser Ala Ser Gly Ser Thr Gly Gly Gly
            355             360             365

Ser Gly Ser Glu Ser Gly Ser Gly Gly Ser Glu Ser Gly Ser Gly Gly
            370             375             380

Ser Gly Ser Glu Ser Gly Ser Gly Gly Pro Glu Ser Pro Gly Ser Gly
385             390             395             400

Gly Gly Ser Gly Ser Glu Ser Gly Ser Gly Gly Thr Ser Gly Ser Thr
            405             410             415

Gly Gly Ser Gly Ser Glu Ser Gly Ser Gly Gly Gly Ser Gly Gly
            420             425             430

Gly Ser Gly Gly Gly Ala Ser Ser Gly Val Arg Leu Trp Ala Thr Arg
            435             440             445

Gln Ala Met Leu Gly Gln Val His Glu Val Pro Glu Gly Trp Leu Ile
            450             455             460

Phe Val Ala Glu Gln Glu Glu Leu Tyr Val Arg Val Gln Asn Gly Phe
465             470             475             480

Arg Lys Val Gln Leu Glu Ala Arg Thr Pro Leu Pro Arg Gly
            485             490

<210> SEQ ID NO 26
<211> LENGTH: 550
```

```
<212> TYPE: PRT
<213> ORGANISM: Artificial Sequence
<220> FEATURE:
<223> OTHER INFORMATION: synthesized

<400> SEQUENCE: 26

Leu Pro Ala Gln Val Ala Phe Thr Pro Tyr Ala Pro Glu Pro Gly Ser
 1               5                  10                  15

Thr Cys Arg Leu Arg Glu Tyr Tyr Asp Gln Thr Ala Gln Met Cys Cys
             20                  25                  30

Ser Lys Cys Ser Pro Gly Gln His Ala Lys Val Phe Cys Thr Lys Thr
         35                  40                  45

Ser Asp Thr Val Cys Asp Ser Cys Glu Asp Ser Thr Tyr Thr Gln Leu
     50                  55                  60

Trp Asn Trp Val Pro Glu Cys Leu Ser Cys Gly Ser Arg Cys Ser Ser
 65                  70                  75                  80

Asp Gln Val Glu Thr Gln Ala Cys Thr Arg Glu Gln Asn Arg Ile Cys
                 85                  90                  95

Thr Cys Arg Pro Gly Trp Tyr Cys Ala Leu Ser Lys Gln Glu Gly Cys
            100                 105                 110

Arg Leu Cys Ala Pro Leu Arg Lys Cys Arg Pro Gly Phe Gly Val Ala
        115                 120                 125

Arg Pro Gly Thr Glu Thr Ser Asp Val Val Cys Lys Pro Cys Ala Pro
    130                 135                 140

Gly Thr Phe Ser Asn Thr Thr Ser Ser Thr Asp Ile Cys Arg Pro His
145                 150                 155                 160

Gln Ile Cys Asn Val Val Ala Ile Pro Gly Asn Ala Ser Met Asp Ala
                165                 170                 175

Val Cys Thr Ser Thr Ser Pro Thr Arg Ser Met Ala Pro Gly Ala Val
            180                 185                 190

His Leu Pro Gln Pro Val Ser Thr Arg Ser Gln His Thr Gln Pro Thr
        195                 200                 205

Pro Glu Pro Ser Thr Ala Pro Ser Thr Ser Phe Leu Leu Pro Met Gly
    210                 215                 220

Pro Ser Pro Pro Ala Glu Gly Ser Thr Gly Asp Gly Gly Ser Gly Gly
225                 230                 235                 240

Gly Gly Ser Gly Gly Gly Gly Ala Ser Ser Gly Val Arg Leu Trp Ala
                245                 250                 255

Thr Arg Gln Ala Met Leu Gly Gln Val His Glu Val Pro Glu Gly Trp
            260                 265                 270

Leu Ile Phe Val Ala Glu Gln Glu Leu Tyr Val Arg Val Gln Asn
        275                 280                 285

Gly Phe Arg Lys Val Gln Leu Glu Ala Arg Thr Pro Leu Pro Arg Gly
    290                 295                 300

Gly Gly Gly Ser Gly Gly Ser Gly Ser Gly Ser Glu Ser Gly Ser
305                 310                 315                 320

Gly Gly Gly Ser Thr Ser Ser Gly Thr Gly Ser Glu Thr Glu Ser Pro
            325                 330                 335

Gly Ser Gly Ser Glu Ser Gly Ser Pro Ser Ser Ala Gly Ser Gly
        340                 345                 350

Ser Gly Ser Glu Ser Gly Ser Gly Ser Ser Gly Pro Gly Ser
    355                 360                 365

Thr Gly Gly Ser Gly Ser Glu Ser Gly Ser Pro Gly Ser Ser Gly
    370                 375                 380
```

```
Thr Gly Gly Thr Ala Thr Gly Ser Gly Ser Glu Ser Gly Ser Gly Pro
385                 390                 395                 400

Gly Ser Ser Gly Pro Gly Ser Thr Gly Ser Gly Ser Gly Ser Glu Ser
                405                 410                 415

Gly Ser Gly Ser Gly Ser Ser Gly Thr Gly Ser Thr Gly Gly Ser Gly
                420                 425                 430

Ser Glu Ser Gly Ser Gly Pro Gly Ser Pro Arg Pro Gly Ser Thr Gly
            435                 440                 445

Thr Gly Ser Gly Ser Glu Ser Gly Ser Gly Pro Gly Ser Ser Glu Arg
            450                 455                 460

Gly Ser Ala Gly Gly Ser Gly Ser Glu Ser Gly Ser Gly Thr Ser Glu
465                 470                 475                 480

Ser Ser Ala Ser Gly Ser Thr Gly Gly Ser Gly Ser Glu Ser Gly Ser
                485                 490                 495

Gly Ser Glu Ser Gly Ser Gly Ser Ser Glu Ser Gly Ser Gly Gly Pro
                500                 505                 510

Glu Ser Pro Gly Ser Gly Gly Ser Gly Ser Glu Ser Gly Ser Gly Thr
            515                 520                 525

Ser Gly Ser Thr Gly Ser Gly Ser Glu Ser Gly Ser Gly Gly Gly Ser
            530                 535                 540

Gly Gly Gly Ser Gly Gly
545                 550

<210> SEQ ID NO 27
<211> LENGTH: 575
<212> TYPE: PRT
<213> ORGANISM: Artificial Sequence
<220> FEATURE:
<223> OTHER INFORMATION: synthesized

<400> SEQUENCE: 27

Leu Pro Ala Gln Val Ala Phe Thr Pro Tyr Ala Pro Glu Pro Gly Ser
1               5                   10                  15

Thr Cys Arg Leu Arg Glu Tyr Tyr Asp Gln Thr Ala Gln Met Cys Cys
            20                  25                  30

Ser Lys Cys Ser Pro Gly Gln His Ala Lys Val Phe Cys Thr Lys Thr
        35                  40                  45

Ser Asp Thr Val Cys Asp Ser Cys Glu Asp Ser Thr Tyr Thr Gln Leu
    50                  55                  60

Trp Asn Trp Val Pro Glu Cys Leu Ser Cys Gly Ser Arg Cys Ser Ser
65              70                  75                  80

Asp Gln Val Glu Thr Gln Ala Cys Thr Arg Glu Gln Asn Arg Ile Cys
            85                  90                  95

Thr Cys Arg Pro Gly Trp Tyr Cys Ala Leu Ser Lys Gln Glu Gly Cys
        100                 105                 110

Arg Leu Cys Ala Pro Leu Arg Lys Cys Arg Pro Gly Phe Gly Val Ala
    115                 120                 125

Arg Pro Gly Thr Glu Thr Ser Asp Val Val Cys Lys Pro Cys Ala Pro
130                 135                 140

Gly Thr Phe Ser Asn Thr Thr Ser Ser Thr Asp Ile Cys Arg Pro His
145                 150                 155                 160

Gln Ile Cys Asn Val Val Ala Ile Pro Gly Asn Ala Ser Met Asp Ala
            165                 170                 175

Val Cys Thr Ser Thr Ser Pro Thr Arg Ser Met Ala Pro Gly Ala Val
        180                 185                 190
```

His Leu Pro Gln Pro Val Ser Thr Arg Ser Gln His Thr Gln Pro Thr
            195                 200                 205

Pro Glu Pro Ser Thr Ala Pro Ser Thr Ser Phe Leu Leu Pro Met Gly
210                 215                 220

Pro Ser Pro Pro Ala Glu Gly Ser Thr Gly Asp Gly Gly Ser Gly
225                 230                 235                 240

Gly Gly Ser Gly Gly Gly Ala Ser Ser Gly Val Arg Leu Trp Ala
            245                 250                 255

Thr Arg Gln Ala Met Leu Gly Gln Val His Glu Val Pro Glu Gly Trp
            260                 265                 270

Leu Ile Phe Val Ala Glu Gln Glu Leu Tyr Val Arg Val Gln Asn
            275                 280                 285

Gly Phe Arg Lys Val Gln Leu Glu Ala Arg Thr Pro Leu Pro Arg Gly
            290                 295                 300

Gly Gly Gly Ser Gly Gly Gly Ser Gly Gly Ser Gly Ser Glu Ser Gly
305                 310                 315                 320

Ser Gly Gly Ser Thr Ser Ser Gly Thr Gly Ser Glu Thr Glu Ser
            325                 330                 335

Pro Gly Gly Ser Gly Ser Glu Ser Gly Ser Gly Gly Pro Ser Ser Ala
            340                 345                 350

Gly Ser Gly Gly Ser Gly Ser Glu Ser Gly Ser Gly Gly Ser Gly Ser
            355                 360                 365

Ser Gly Pro Gly Ser Thr Gly Gly Ser Gly Ser Glu Ser Gly Ser
            370                 375                 380

Gly Gly Pro Gly Ser Ser Gly Thr Gly Thr Ala Thr Gly Gly Ser
385                 390                 395                 400

Gly Ser Glu Ser Gly Ser Gly Gly Pro Gly Ser Ser Gly Pro Gly Ser
            405                 410                 415

Thr Gly Ser Gly Gly Ser Gly Ser Glu Ser Gly Ser Gly Gly Ser Gly
            420                 425                 430

Ser Ser Gly Thr Gly Ser Thr Gly Gly Ser Gly Ser Glu Ser Gly
            435                 440                 445

Ser Gly Gly Pro Gly Ser Pro Arg Pro Gly Ser Thr Gly Thr Gly Gly
450                 455                 460

Ser Gly Ser Glu Ser Gly Ser Gly Pro Gly Ser Ser Glu Arg Gly
465                 470                 475                 480

Ser Ala Gly Gly Gly Ser Gly Ser Glu Ser Gly Ser Gly Gly Thr Ser
            485                 490                 495

Glu Ser Ser Ala Ser Gly Ser Thr Gly Gly Ser Gly Ser Glu Ser
            500                 505                 510

Gly Ser Gly Gly Ser Glu Ser Gly Ser Gly Gly Ser Gly Ser Glu Ser
            515                 520                 525

Gly Ser Gly Gly Pro Glu Ser Pro Gly Ser Gly Gly Ser Gly Ser
            530                 535                 540

Glu Ser Gly Ser Gly Gly Thr Ser Gly Ser Thr Gly Ser Gly Ser
545                 550                 555                 560

Glu Ser Gly Ser Gly Gly Gly Ser Gly Gly Gly Ser Gly Gly
            565                 570                 575

<210> SEQ ID NO 28
<211> LENGTH: 518
<212> TYPE: PRT
<213> ORGANISM: Artificial Sequence
<220> FEATURE:
<223> OTHER INFORMATION: synthesized

<400> SEQUENCE: 28

```
Ser Asp Thr Gly Arg Pro Phe Val Glu Met Tyr Ser Glu Ile Pro Glu
1               5                   10                  15

Ile Ile His Met Thr Glu Gly Arg Glu Leu Val Ile Pro Cys Arg Val
            20                  25                  30

Thr Ser Pro Asn Ile Thr Val Thr Leu Lys Lys Phe Pro Leu Asp Thr
        35                  40                  45

Leu Ile Pro Asp Gly Lys Arg Ile Ile Trp Asp Ser Arg Lys Gly Phe
    50                  55                  60

Ile Ile Ser Asn Ala Thr Tyr Lys Glu Ile Gly Leu Leu Thr Cys Glu
65                  70                  75                  80

Ala Thr Val Asn Gly His Leu Tyr Lys Thr Asn Tyr Leu Thr His Arg
                85                  90                  95

Gln Thr Asn Thr Ile Ile Asp Val Val Leu Ser Pro Ser His Gly Ile
            100                 105                 110

Glu Leu Ser Val Gly Glu Lys Leu Val Leu Asn Cys Thr Ala Arg Thr
        115                 120                 125

Glu Leu Asn Val Gly Ile Asp Phe Asn Trp Glu Tyr Pro Ser Ser Lys
    130                 135                 140

His Gln His Lys Lys Leu Val Asn Arg Asp Leu Lys Thr Gln Ser Gly
145                 150                 155                 160

Ser Glu Met Lys Lys Phe Leu Ser Thr Leu Thr Ile Asp Gly Val Thr
                165                 170                 175

Arg Ser Asp Gln Gly Leu Tyr Thr Cys Ala Ala Ser Ser Gly Leu Met
            180                 185                 190

Thr Lys Lys Asn Ser Thr Phe Val Arg Val His Glu Gly Gly Ser
        195                 200                 205

Gly Gly Gly Ser Gly Gly Ala Ser Ser Gly Val Arg Leu Trp Ala
    210                 215                 220

Thr Arg Gln Ala Met Leu Gly Gln Val His Glu Val Pro Glu Gly Trp
225                 230                 235                 240

Leu Ile Phe Val Ala Glu Gln Glu Leu Tyr Val Arg Val Gln Asn
                245                 250                 255

Gly Phe Arg Lys Val Gln Leu Glu Ala Arg Thr Pro Leu Pro Arg Gly
            260                 265                 270

Gly Gly Gly Ser Gly Gly Gly Ser Gly Ser Gly Glu Ser Gly Ser
        275                 280                 285

Gly Gly Gly Ser Thr Ser Ser Gly Thr Gly Ser Glu Thr Glu Ser Pro
    290                 295                 300

Gly Ser Gly Ser Glu Ser Gly Ser Gly Pro Ser Ser Ala Gly Ser Gly
305                 310                 315                 320

Ser Gly Ser Glu Ser Gly Ser Gly Ser Ser Gly Pro Gly Ser
                325                 330                 335

Thr Gly Gly Ser Gly Ser Glu Gly Ser Gly Pro Gly Ser Ser Gly
            340                 345                 350

Thr Gly Thr Ala Thr Gly Ser Gly Ser Glu Ser Gly Ser Gly Pro
        355                 360                 365

Gly Ser Ser Gly Pro Gly Ser Thr Gly Ser Gly Ser Gly Ser Glu Ser
    370                 375                 380

Gly Ser Gly Ser Gly Ser Ser Gly Thr Gly Ser Thr Gly Gly Ser Gly
385                 390                 395                 400

Ser Glu Ser Gly Ser Gly Pro Gly Ser Pro Arg Pro Gly Ser Thr Gly
```

```
                    405                 410                 415
Thr Gly Ser Gly Ser Glu Ser Gly Pro Gly Ser Ser Glu Arg
            420                 425                 430

Gly Ser Ala Gly Gly Ser Gly Ser Glu Ser Gly Ser Gly Thr Ser Glu
            435                 440                 445

Ser Ser Ala Ser Gly Ser Thr Gly Gly Ser Gly Ser Glu Ser Gly Ser
            450                 455                 460

Gly Ser Glu Ser Gly Ser Gly Ser Gly Ser Glu Ser Gly Ser Gly Pro
465                 470                 475                 480

Glu Ser Pro Gly Ser Gly Ser Gly Ser Glu Ser Gly Ser Gly Ser Thr
            485                 490                 495

Ser Gly Ser Thr Gly Ser Gly Ser Glu Ser Gly Ser Gly Gly Gly Ser
            500                 505                 510

Gly Gly Gly Ser Gly Gly
            515

<210> SEQ ID NO 29
<211> LENGTH: 543
<212> TYPE: PRT
<213> ORGANISM: Artificial Sequence
<220> FEATURE:
<223> OTHER INFORMATION: synthesized

<400> SEQUENCE: 29

Ser Asp Thr Gly Arg Pro Phe Val Glu Met Tyr Ser Glu Ile Pro Glu
1               5                   10                  15

Ile Ile His Met Thr Glu Gly Arg Glu Leu Val Ile Pro Cys Arg Val
            20                  25                  30

Thr Ser Pro Asn Ile Thr Val Thr Leu Lys Lys Phe Pro Leu Asp Thr
        35                  40                  45

Leu Ile Pro Asp Gly Lys Arg Ile Ile Trp Asp Ser Arg Lys Gly Phe
    50                  55                  60

Ile Ile Ser Asn Ala Thr Tyr Lys Glu Ile Gly Leu Leu Thr Cys Glu
65                  70                  75                  80

Ala Thr Val Asn Gly His Leu Tyr Lys Thr Asn Tyr Leu Thr His Arg
                85                  90                  95

Gln Thr Asn Thr Ile Ile Asp Val Val Leu Ser Pro Ser His Gly Ile
            100                 105                 110

Glu Leu Ser Val Gly Glu Lys Leu Val Leu Asn Cys Thr Ala Arg Thr
        115                 120                 125

Glu Leu Asn Val Gly Ile Asp Phe Asn Trp Glu Tyr Pro Ser Ser Lys
    130                 135                 140

His Gln His Lys Lys Leu Val Asn Arg Asp Leu Lys Thr Gln Ser Gly
145                 150                 155                 160

Ser Glu Met Lys Lys Phe Leu Ser Thr Leu Thr Ile Asp Gly Val Thr
                165                 170                 175

Arg Ser Asp Gln Gly Leu Tyr Thr Cys Ala Ala Ser Ser Gly Leu Met
            180                 185                 190

Thr Lys Lys Asn Ser Thr Phe Val Arg Val His Glu Gly Gly Ser
        195                 200                 205

Gly Gly Gly Ser Gly Gly Ala Ser Ser Gly Val Arg Leu Trp Ala
    210                 215                 220

Thr Arg Gln Ala Met Leu Gly Gln Val His Glu Val Pro Glu Gly Trp
225                 230                 235                 240

Leu Ile Phe Val Ala Glu Gln Glu Glu Leu Tyr Val Arg Val Gln Asn
```

```
                        245                 250                 255
Gly Phe Arg Lys Val Gln Leu Glu Ala Arg Thr Pro Leu Pro Arg Gly
            260                 265                 270

Gly Gly Gly Ser Gly Gly Gly Ser Gly Ser Gly Ser Glu Ser Gly
        275                 280                 285

Ser Gly Gly Gly Ser Thr Ser Ser Gly Ser Glu Thr Glu Ser
        290                 295                 300

Pro Gly Gly Ser Gly Ser Glu Ser Gly Ser Gly Pro Ser Ser Ala
305                 310                 315                 320

Gly Ser Gly Gly Ser Gly Ser Glu Ser Gly Ser Gly Gly Ser Gly Ser
                325                 330                 335

Ser Gly Pro Gly Ser Thr Gly Gly Ser Gly Ser Glu Ser Gly Ser
            340                 345                 350

Gly Gly Pro Gly Ser Ser Gly Thr Gly Gly Thr Ala Thr Gly Gly Ser
                355                 360                 365

Gly Ser Glu Ser Gly Ser Gly Gly Pro Gly Ser Ser Gly Pro Gly Ser
    370                 375                 380

Thr Gly Ser Gly Gly Ser Gly Ser Glu Ser Gly Ser Gly Gly Ser Gly
385                 390                 395                 400

Ser Ser Gly Thr Gly Ser Thr Gly Gly Gly Ser Gly Ser Glu Ser Gly
            405                 410                 415

Ser Gly Gly Pro Gly Ser Pro Arg Pro Gly Ser Thr Gly Thr Gly Gly
            420                 425                 430

Ser Gly Ser Glu Ser Gly Ser Gly Gly Pro Gly Ser Ser Glu Arg Gly
            435                 440                 445

Ser Ala Gly Gly Gly Ser Gly Ser Glu Ser Gly Ser Gly Gly Thr Ser
    450                 455                 460

Glu Ser Ser Ala Ser Gly Ser Thr Gly Gly Ser Gly Ser Glu Ser
465                 470                 475                 480

Gly Ser Gly Gly Ser Glu Ser Gly Ser Gly Gly Ser Gly Ser Glu Ser
                485                 490                 495

Gly Ser Gly Gly Pro Glu Ser Pro Gly Ser Gly Gly Ser Gly Ser
            500                 505                 510

Glu Ser Gly Ser Gly Gly Thr Ser Gly Ser Thr Gly Gly Ser Gly Ser
            515                 520                 525

Glu Ser Gly Ser Gly Gly Gly Ser Gly Gly Gly Ser Gly Gly
            530                 535                 540

<210> SEQ ID NO 30
<211> LENGTH: 456
<212> TYPE: PRT
<213> ORGANISM: Artificial Sequence
<220> FEATURE:
<223> OTHER INFORMATION: synthesized

<400> SEQUENCE: 30

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser Gly Gly Gly Ser Gly Gly Gly Ser
        35                  40                  45

Gly Gly Gly Ser Gly Gly Gly Ser Gly Ser Gly Gly Ala Val Pro Pro
    50                  55                  60

Pro Thr Asp Leu Arg Phe Thr Asn Ile Gly Pro Asp Thr Met Arg Val
```

65                  70                  75                  80
Thr Trp Ala Pro Pro Ser Ile Asp Leu Thr Asn Phe Leu Val Arg
                    85                  90                  95
Tyr Ser Pro Val Lys Asn Glu Glu Asp Val Ala Glu Leu Ser Ile Ser
                100                 105                 110
Pro Ser Asp Asn Ala Val Val Leu Thr Asn Leu Leu Pro Gly Thr Glu
            115                 120                 125
Tyr Val Val Ser Val Ser Ser Val Tyr Glu Gln His Glu Ser Thr Pro
        130                 135                 140
Leu Arg Gly Arg Gln Lys Thr Gly Gly Gly Ser Gly Gly Gly Ser
145                 150                 155                 160
Gly Ser Gly Ser Glu Ser Gly Ser Gly Gly Ser Thr Ser Ser Gly
                165                 170                 175
Thr Gly Ser Glu Thr Glu Ser Pro Gly Ser Gly Ser Gly Ser Gly Ser
            180                 185                 190
Gly Pro Ser Ser Ala Gly Ser Gly Ser Glu Ser Gly Ser Gly
        195                 200                 205
Ser Gly Ser Ser Gly Pro Gly Ser Thr Gly Gly Ser Gly Ser Glu Ser
    210                 215                 220
Gly Ser Gly Pro Gly Ser Ser Gly Thr Gly Gly Thr Ala Thr Gly Ser
225                 230                 235                 240
Gly Ser Glu Ser Gly Ser Gly Pro Gly Ser Ser Gly Pro Gly Ser Thr
                245                 250                 255
Gly Ser Gly Ser Gly Ser Glu Ser Gly Ser Gly Ser Gly Ser Ser Gly
            260                 265                 270
Thr Gly Ser Thr Gly Gly Ser Gly Ser Glu Ser Gly Ser Gly Pro Gly
        275                 280                 285
Ser Pro Arg Pro Gly Ser Thr Gly Thr Gly Ser Gly Ser Glu Ser Gly
    290                 295                 300
Ser Gly Pro Gly Ser Ser Glu Arg Gly Ser Ala Gly Gly Ser Gly Ser
305                 310                 315                 320
Glu Ser Gly Ser Gly Thr Ser Glu Ser Ser Ala Ser Gly Ser Thr Gly
                325                 330                 335
Gly Ser Gly Ser Glu Ser Gly Ser Gly Ser Glu Ser Gly Ser Gly Ser
            340                 345                 350
Gly Ser Glu Ser Gly Ser Gly Pro Glu Ser Pro Gly Ser Gly Gly Ser
        355                 360                 365
Gly Ser Glu Ser Gly Ser Gly Thr Ser Gly Ser Thr Gly Ser Gly Ser
    370                 375                 380
Glu Ser Gly Ser Gly Gly Ser Gly Gly Ser Gly Gly Gly Ala
385                 390                 395                 400
Ser Ser Gly Val Arg Leu Trp Ala Thr Arg Gln Ala Met Leu Gly Gln
                405                 410                 415
Val His Glu Val Pro Glu Gly Trp Leu Ile Phe Val Ala Glu Gln Glu
                420                 425                 430
Glu Leu Tyr Val Arg Val Gln Asn Gly Phe Arg Lys Val Gln Leu Glu
            435                 440                 445
Ala Arg Thr Pro Leu Pro Arg Gly
        450                 455

<210> SEQ ID NO 31
<211> LENGTH: 481
<212> TYPE: PRT
<213> ORGANISM: Artificial Sequence
<220> FEATURE:
<223> OTHER INFORMATION: synthesized

<400> SEQUENCE: 31

```
His Gly Glu Gly Thr Phe Thr Ser Asp Leu Ser Lys Gln Met Glu
1               5                   10                  15

Glu Ala Val Arg Leu Phe Ile Glu Trp Leu Lys Asn Gly Pro Ser
            20                  25                  30

Ser Gly Ala Pro Pro Pro Ser Gly Gly Ser Gly Gly Gly Ser
            35                  40                  45

Gly Gly Gly Ser Gly Gly Gly Ser Gly Gly Ala Val Pro Pro
50                  55                  60

Pro Thr Asp Leu Arg Phe Thr Asn Ile Gly Pro Asp Thr Met Arg Val
65                  70                  75                  80

Thr Trp Ala Pro Pro Ser Ile Asp Leu Thr Asn Phe Leu Val Arg
                85                  90                  95

Tyr Ser Pro Val Lys Asn Glu Glu Asp Val Ala Glu Leu Ser Ile Ser
                100                 105                 110

Pro Ser Asp Asn Ala Val Val Leu Thr Asn Leu Leu Pro Gly Thr Glu
            115                 120                 125

Tyr Val Val Ser Val Ser Ser Val Tyr Glu Gln His Glu Ser Thr Pro
    130                 135                 140

Leu Arg Gly Arg Gln Lys Thr Gly Gly Gly Ser Gly Gly Gly Ser
145                 150                 155                 160

Gly Gly Ser Gly Ser Glu Ser Gly Ser Gly Gly Ser Thr Ser Ser
                165                 170                 175

Gly Thr Gly Ser Glu Thr Glu Ser Pro Gly Gly Ser Gly Ser Glu Ser
            180                 185                 190

Gly Ser Gly Gly Pro Ser Ser Ala Gly Ser Gly Gly Ser Gly Glu
            195                 200                 205

Ser Gly Ser Gly Ser Gly Ser Ser Gly Pro Gly Ser Thr Gly Gly
            210                 215                 220

Gly Ser Gly Ser Glu Ser Gly Ser Gly Pro Gly Ser Ser Gly Thr
225                 230                 235                 240

Gly Gly Thr Ala Thr Gly Gly Ser Gly Ser Glu Ser Gly Ser Gly Gly
                245                 250                 255

Pro Gly Ser Ser Gly Pro Gly Ser Thr Gly Ser Gly Ser Gly Ser
            260                 265                 270

Glu Ser Gly Ser Gly Gly Ser Gly Ser Ser Gly Thr Gly Ser Thr Gly
            275                 280                 285

Gly Gly Ser Gly Ser Glu Ser Gly Ser Gly Gly Pro Gly Ser Pro Arg
    290                 295                 300

Pro Gly Ser Thr Gly Thr Gly Ser Gly Ser Gly Glu Ser Gly Ser Gly
305                 310                 315                 320

Gly Pro Gly Ser Ser Glu Arg Gly Ser Ala Gly Gly Ser Gly Ser
            325                 330                 335

Glu Ser Gly Ser Gly Gly Thr Ser Glu Ser Ser Ala Ser Gly Ser Thr
            340                 345                 350

Gly Gly Gly Ser Gly Ser Glu Ser Gly Ser Gly Ser Glu Ser Gly
            355                 360                 365

Ser Gly Gly Ser Gly Ser Glu Ser Gly Ser Gly Gly Pro Glu Ser Pro
    370                 375                 380

Gly Ser Gly Gly Gly Ser Gly Ser Glu Ser Gly Ser Gly Gly Thr Ser
385                 390                 395                 400
```

Gly Ser Thr Gly Gly Ser Ser Glu Ser Gly Ser Gly Gly Gly
                405                 410                 415

Ser Gly Gly Gly Ser Gly Gly Ala Ser Ser Gly Val Arg Leu Trp
            420                 425                 430

Ala Thr Arg Gln Ala Met Leu Gly Gln Val His Glu Val Pro Glu Gly
            435                 440                 445

Trp Leu Ile Phe Val Ala Glu Gln Glu Leu Tyr Val Arg Val Gln
    450                 455                 460

Asn Gly Phe Arg Lys Val Gln Leu Glu Ala Arg Thr Pro Leu Pro Arg
465                 470                 475                 480

Gly

<210> SEQ ID NO 32
<211> LENGTH: 14
<212> TYPE: PRT
<213> ORGANISM: Homo Sapiens

<400> SEQUENCE: 32

Gly Ser Thr Ser Ser Gly Thr Gly Ser Glu Thr Glu Ser Pro
1               5                   10

<210> SEQ ID NO 33
<211> LENGTH: 6
<212> TYPE: PRT
<213> ORGANISM: Homo Sapiens

<400> SEQUENCE: 33

Pro Ser Ser Ala Gly Ser
1               5

<210> SEQ ID NO 34
<211> LENGTH: 10
<212> TYPE: PRT
<213> ORGANISM: Homo Sapiens

<400> SEQUENCE: 34

Ser Gly Ser Ser Gly Pro Gly Ser Thr Gly
1               5                   10

<210> SEQ ID NO 35
<211> LENGTH: 11
<212> TYPE: PRT
<213> ORGANISM: Homo Sapiens

<400> SEQUENCE: 35

Pro Gly Ser Ser Gly Thr Gly Gly Thr Ala Thr
1               5                   10

<210> SEQ ID NO 36
<211> LENGTH: 11
<212> TYPE: PRT
<213> ORGANISM: Homo Sapiens

<400> SEQUENCE: 36

Pro Gly Ser Ser Gly Pro Gly Ser Thr Gly Ser
1               5                   10

<210> SEQ ID NO 37
<211> LENGTH: 10
<212> TYPE: PRT
<213> ORGANISM: Homo Sapiens

```
<400> SEQUENCE: 37

Ser Gly Ser Ser Gly Thr Gly Ser Thr Gly
1               5                   10

<210> SEQ ID NO 38
<211> LENGTH: 12
<212> TYPE: PRT
<213> ORGANISM: Homo Sapiens

<400> SEQUENCE: 38

Pro Gly Ser Pro Ala Arg Pro Gly Ser Thr Gly Thr
1               5                   10

<210> SEQ ID NO 39
<211> LENGTH: 10
<212> TYPE: PRT
<213> ORGANISM: Homo Sapiens

<400> SEQUENCE: 39

Pro Gly Ser Ser Glu Ala Gly Ser Ala Gly
1               5                   10

<210> SEQ ID NO 40
<211> LENGTH: 11
<212> TYPE: PRT
<213> ORGANISM: Homo Sapiens

<400> SEQUENCE: 40

Thr Ser Gly Ser Ser Ala Ser Gly Ser Thr Gly
1               5                   10

<210> SEQ ID NO 41
<211> LENGTH: 5
<212> TYPE: PRT
<213> ORGANISM: Homo Sapiens

<400> SEQUENCE: 41

Ser Glu Ser Gly Ser
1               5

<210> SEQ ID NO 42
<211> LENGTH: 7
<212> TYPE: PRT
<213> ORGANISM: Homo Sapiens

<400> SEQUENCE: 42

Pro Gly Ser Pro Gly Ser Gly
1               5

<210> SEQ ID NO 43
<211> LENGTH: 5
<212> TYPE: PRT
<213> ORGANISM: Homo Sapiens

<400> SEQUENCE: 43

Thr Ser Gly Ser Thr
1               5

<210> SEQ ID NO 44
<211> LENGTH: 5
<212> TYPE: PRT
<213> ORGANISM: Artificial Sequence
<220> FEATURE:
<223> OTHER INFORMATION: synthesized
```

```
<400> SEQUENCE: 44

Gly Ser Glu Ser Gly
1               5

<210> SEQ ID NO 45
<211> LENGTH: 5
<212> TYPE: PRT
<213> ORGANISM: Artificial Sequence
<220> FEATURE:
<223> OTHER INFORMATION: synthesized

<400> SEQUENCE: 45

Gly Ser Gly Ser Gly
1               5

<210> SEQ ID NO 46
<211> LENGTH: 5
<212> TYPE: PRT
<213> ORGANISM: Artificial Sequence
<220> FEATURE:
<223> OTHER INFORMATION: synthesized

<400> SEQUENCE: 46

Gly Ser Pro Ser Gly
1               5

<210> SEQ ID NO 47
<211> LENGTH: 5
<212> TYPE: PRT
<213> ORGANISM: Artificial Sequence
<220> FEATURE:
<223> OTHER INFORMATION: synthesized

<400> SEQUENCE: 47

Gly Ser Thr Ser Gly
1               5

<210> SEQ ID NO 48
<211> LENGTH: 7
<212> TYPE: PRT
<213> ORGANISM: Artificial Sequence
<220> FEATURE:
<223> OTHER INFORMATION: synthesized

<400> SEQUENCE: 48

Gly Ser Gly Ser Glu Ser Gly
1               5

<210> SEQ ID NO 49
<211> LENGTH: 7
<212> TYPE: PRT
<213> ORGANISM: Artificial Sequence
<220> FEATURE:
<223> OTHER INFORMATION: synthesized

<400> SEQUENCE: 49

Gly Ser Glu Ser Gly Ser Gly
1               5

<210> SEQ ID NO 50
<211> LENGTH: 7
<212> TYPE: PRT
<213> ORGANISM: Artificial Sequence
<220> FEATURE:
<223> OTHER INFORMATION: synthesized

<400> SEQUENCE: 50
```

```
Gly Ser Thr Ser Glu Ser Gly
1               5

<210> SEQ ID NO 51
<211> LENGTH: 7
<212> TYPE: PRT
<213> ORGANISM: Artificial Sequence
<220> FEATURE:
<223> OTHER INFORMATION: synthesized

<400> SEQUENCE: 51

Gly Ser Glu Ser Thr Ser Gly
1               5

<210> SEQ ID NO 52
<211> LENGTH: 7
<212> TYPE: PRT
<213> ORGANISM: Artificial Sequence
<220> FEATURE:
<223> OTHER INFORMATION: synthesized

<400> SEQUENCE: 52

Gly Ser Pro Ser Glu Ser Gly
1               5

<210> SEQ ID NO 53
<211> LENGTH: 7
<212> TYPE: PRT
<213> ORGANISM: Artificial Sequence
<220> FEATURE:
<223> OTHER INFORMATION: synthesized

<400> SEQUENCE: 53

Gly Ser Glu Ser Pro Ser Gly
1               5

<210> SEQ ID NO 54
<211> LENGTH: 7
<212> TYPE: PRT
<213> ORGANISM: Artificial Sequence
<220> FEATURE:
<223> OTHER INFORMATION: synthesized

<400> SEQUENCE: 54

Gly Ser Gly Glu Gly Ser Gly
1               5

<210> SEQ ID NO 55
<211> LENGTH: 7
<212> TYPE: PRT
<213> ORGANISM: Artificial Sequence
<220> FEATURE:
<223> OTHER INFORMATION: synthesized

<400> SEQUENCE: 55

Gly Ser Gly Thr Gly Ser Gly
1               5

<210> SEQ ID NO 56
<211> LENGTH: 7
<212> TYPE: PRT
<213> ORGANISM: Artificial Sequence
<220> FEATURE:
<223> OTHER INFORMATION: synthesized

<400> SEQUENCE: 56
```

Gly Ser Gly Pro Gly Ser Gly
1               5

<210> SEQ ID NO 57
<211> LENGTH: 9
<212> TYPE: PRT
<213> ORGANISM: Artificial Sequence
<220> FEATURE:
<223> OTHER INFORMATION: synthesized

<400> SEQUENCE: 57

Gly Ser Pro Ser Glu Ser Gly Ser Gly
1               5

<210> SEQ ID NO 58
<211> LENGTH: 9
<212> TYPE: PRT
<213> ORGANISM: Artificial Sequence
<220> FEATURE:
<223> OTHER INFORMATION: synthesized

<400> SEQUENCE: 58

Gly Ser Pro Ser Gly Ser Glu Ser Gly
1               5

<210> SEQ ID NO 59
<211> LENGTH: 9
<212> TYPE: PRT
<213> ORGANISM: Artificial Sequence
<220> FEATURE:
<223> OTHER INFORMATION: synthesized

<400> SEQUENCE: 59

Gly Ser Glu Ser Pro Ser Gly Ser Gly
1               5

<210> SEQ ID NO 60
<211> LENGTH: 9
<212> TYPE: PRT
<213> ORGANISM: Artificial Sequence
<220> FEATURE:
<223> OTHER INFORMATION: synthesized

<400> SEQUENCE: 60

Gly Ser Glu Ser Gly Ser Pro Ser Gly
1               5

<210> SEQ ID NO 61
<211> LENGTH: 9
<212> TYPE: PRT
<213> ORGANISM: Artificial Sequence
<220> FEATURE:
<223> OTHER INFORMATION: synthesized

<400> SEQUENCE: 61

Gly Ser Gly Ser Pro Ser Glu Ser Gly
1               5

<210> SEQ ID NO 62
<211> LENGTH: 9
<212> TYPE: PRT
<213> ORGANISM: Artificial Sequence
<220> FEATURE:
<223> OTHER INFORMATION: synthesized

<400> SEQUENCE: 62

Gly Ser Gly Ser Glu Ser Pro Ser Gly

```
1               5

<210> SEQ ID NO 63
<211> LENGTH: 9
<212> TYPE: PRT
<213> ORGANISM: Artificial Sequence
<220> FEATURE:
<223> OTHER INFORMATION: synthesized

<400> SEQUENCE: 63

Gly Ser Thr Ser Glu Ser Gly Ser Gly
1               5

<210> SEQ ID NO 64
<211> LENGTH: 9
<212> TYPE: PRT
<213> ORGANISM: Artificial Sequence
<220> FEATURE:
<223> OTHER INFORMATION: synthesized

<400> SEQUENCE: 64

Gly Ser Thr Ser Gly Ser Glu Ser Gly
1               5

<210> SEQ ID NO 65
<211> LENGTH: 9
<212> TYPE: PRT
<213> ORGANISM: Artificial Sequence
<220> FEATURE:
<223> OTHER INFORMATION: synthesized

<400> SEQUENCE: 65

Gly Ser Glu Ser Thr Ser Gly Ser Gly
1               5

<210> SEQ ID NO 66
<211> LENGTH: 9
<212> TYPE: PRT
<213> ORGANISM: Artificial Sequence
<220> FEATURE:
<223> OTHER INFORMATION: synthesized

<400> SEQUENCE: 66

Gly Ser Glu Ser Gly Ser Thr Ser Gly
1               5

<210> SEQ ID NO 67
<211> LENGTH: 9
<212> TYPE: PRT
<213> ORGANISM: Artificial Sequence
<220> FEATURE:
<223> OTHER INFORMATION: synthesized

<400> SEQUENCE: 67

Gly Ser Gly Ser Thr Ser Glu Ser Gly
1               5

<210> SEQ ID NO 68
<211> LENGTH: 9
<212> TYPE: PRT
<213> ORGANISM: Artificial Sequence
<220> FEATURE:
<223> OTHER INFORMATION: synthesized

<400> SEQUENCE: 68

Gly Ser Gly Ser Glu Ser Thr Ser Gly
1               5
```

<210> SEQ ID NO 69
<211> LENGTH: 9
<212> TYPE: PRT
<213> ORGANISM: Artificial Sequence
<220> FEATURE:
<223> OTHER INFORMATION: synthesized

<400> SEQUENCE: 69

Gly Ser Gly Ser Glu Ser Gly Ser Gly
1               5

<210> SEQ ID NO 70
<211> LENGTH: 9
<212> TYPE: PRT
<213> ORGANISM: Artificial Sequence
<220> FEATURE:
<223> OTHER INFORMATION: synthesized

<400> SEQUENCE: 70

Gly Gly Ser Gly Glu Gly Ser Gly Gly
1               5

<210> SEQ ID NO 71
<211> LENGTH: 9
<212> TYPE: PRT
<213> ORGANISM: Artificial Sequence
<220> FEATURE:
<223> OTHER INFORMATION: synthesized

<400> SEQUENCE: 71

Gly Ser Gly Gly Glu Gly Gly Ser Gly
1               5

<210> SEQ ID NO 72
<211> LENGTH: 9
<212> TYPE: PRT
<213> ORGANISM: Artificial Sequence
<220> FEATURE:
<223> OTHER INFORMATION: synthesized

<400> SEQUENCE: 72

Gly Gly Ser Gly Glu Ser Gly Ser Gly
1               5

<210> SEQ ID NO 73
<211> LENGTH: 9
<212> TYPE: PRT
<213> ORGANISM: Artificial Sequence
<220> FEATURE:
<223> OTHER INFORMATION: synthesized

<400> SEQUENCE: 73

Gly Ser Gly Ser Glu Gly Ser Gly Gly
1               5

<210> SEQ ID NO 74
<211> LENGTH: 11
<212> TYPE: PRT
<213> ORGANISM: Artificial Sequence
<220> FEATURE:
<223> OTHER INFORMATION: synthesized

<400> SEQUENCE: 74

Gly Gly Ser Gly Ser Glu Ser Gly Ser Gly Gly
1               5                   10

<210> SEQ ID NO 75
<211> LENGTH: 9
<212> TYPE: PRT
<213> ORGANISM: Artificial Sequence
<220> FEATURE:
<223> OTHER INFORMATION: synthesized

<400> SEQUENCE: 75

Gly Gly Ser Gly Gly Gly Ser Gly Gly
1               5

<210> SEQ ID NO 76
<211> LENGTH: 7
<212> TYPE: PRT
<213> ORGANISM: Artificial Sequence
<220> FEATURE:
<223> OTHER INFORMATION: synthesized

<400> SEQUENCE: 76

Gly Gly Gly Gly Ser Gly Gly
1               5

<210> SEQ ID NO 77
<211> LENGTH: 8
<212> TYPE: PRT
<213> ORGANISM: Artificial Sequence
<220> FEATURE:
<223> OTHER INFORMATION: synthesized

<400> SEQUENCE: 77

Gly Gly Gly Ser Gly Gly Gly Gly
1               5

<210> SEQ ID NO 78
<211> LENGTH: 35
<212> TYPE: DNA
<213> ORGANISM: Artificial Sequence
<220> FEATURE:
<223> OTHER INFORMATION: synthesized

<400> SEQUENCE: 78
cgggatccgg tggcggcgcc tcctcagggg tgagg                               35

<210> SEQ ID NO 79
<211> LENGTH: 40
<212> TYPE: DNA
<213> ORGANISM: Artificial Sequence
<220> FEATURE:
<223> OTHER INFORMATION: synthesized

<400> SEQUENCE: 79
ccgctcgagt taccctcgtg ggagtggtgt ccgggcctcc                          40

<210> SEQ ID NO 80
<211> LENGTH: 163
<212> TYPE: DNA
<213> ORGANISM: Artificial Sequence
<220> FEATURE:
<223> OTHER INFORMATION: synthesized

<400> SEQUENCE: 80
ggaattccat atgcatgccg aagggacttt taccagtgat gtaagttctt atttggaagg    60
tcaagctgca aaagaattca ttgcttggct ggtgaaaggc cgtggtggtg gcggctctgg   120
tggcggtggc acaccattgt ctccaccaac aaacttgcat ctg                     163

<210> SEQ ID NO 81
<211> LENGTH: 51
<212> TYPE: DNA
<213> ORGANISM: Artificial Sequence
<220> FEATURE:
<223> OTHER INFORMATION: synthesized

<400> SEQUENCE: 81
cgggatccac caccagctgg gatgatggta tcagagatag ggacactttc c                 51

<210> SEQ ID NO 82
<211> LENGTH: 163
<212> TYPE: DNA
<213> ORGANISM: Artificial Sequence
<220> FEATURE:
<223> OTHER INFORMATION: synthesized

<400> SEQUENCE: 82
ggaattccat atgcatgccg aagggacttt taccagtgat gtaagttctt atttggaagg        60
tcaagctgca aagaattca ttgcttggct ggtgaaaggc cgtggtggtg gcggctctgg        120
tggcggtggc tctgctgttc ctcctcccac tgacctgcga ttc                         163

<210> SEQ ID NO 83
<211> LENGTH: 46
<212> TYPE: DNA
<213> ORGANISM: Artificial Sequence
<220> FEATURE:
<223> OTHER INFORMATION: synthesized

<400> SEQUENCE: 83
cgggatccac caccacctgt tttctgtctt cctctaagag gtgtgc                       46

<210> SEQ ID NO 84
<211> LENGTH: 84
<212> TYPE: DNA
<213> ORGANISM: Artificial Sequence
<220> FEATURE:
<223> OTHER INFORMATION: synthesized

<400> SEQUENCE: 84
ggaattccat atgcatggcg aagggacttt taccagtgat gtaagttctt atttggaaga        60
gcaagctgca aagaattca ttgc                                                84

<210> SEQ ID NO 85
<211> LENGTH: 40
<212> TYPE: DNA
<213> ORGANISM: Artificial Sequence
<220> FEATURE:
<223> OTHER INFORMATION: synthesized

<400> SEQUENCE: 85
ccgctcgagt taccctcgtg ggagtggtgt ccgggcctcc                              40

<210> SEQ ID NO 86
<211> LENGTH: 8
<212> TYPE: PRT
<213> ORGANISM: Artificial Sequence
<220> FEATURE:
<223> OTHER INFORMATION: synthesized

<400> SEQUENCE: 86

Gly Gly Gly Ser Gly Gly Gly Ser
1               5

<210> SEQ ID NO 87
<211> LENGTH: 10
<212> TYPE: PRT
<213> ORGANISM: Artificial Sequence
<220> FEATURE:
<223> OTHER INFORMATION: synthesized

<400> SEQUENCE: 87

```
Gly Gly Gly Ser Gly Gly Gly Ser Gly Ser
1               5                   10
```

<210> SEQ ID NO 88
<211> LENGTH: 866
<212> TYPE: PRT
<213> ORGANISM: Homo Sapiens

<400> SEQUENCE: 88

```
Met Phe Ser Met Arg Ile Val Cys Leu Val Leu Ser Val Val Gly Thr
1               5                   10                  15

Ala Trp Thr Ala Asp Ser Gly Glu Gly Asp Phe Leu Ala Glu Gly Gly
                20                  25                  30

Gly Val Arg Gly Pro Arg Val Val Glu Arg His Gln Ser Ala Cys Lys
            35                  40                  45

Asp Ser Asp Trp Pro Phe Cys Ser Asp Glu Asp Trp Asn Tyr Lys Cys
        50                  55                  60

Pro Ser Gly Cys Arg Met Lys Gly Leu Ile Asp Glu Val Asn Gln Asp
65                  70                  75                  80

Phe Thr Asn Arg Ile Asn Lys Leu Lys Asn Ser Leu Phe Glu Tyr Gln
                85                  90                  95

Lys Asn Asn Lys Asp Ser His Ser Leu Thr Thr Asn Ile Met Glu Ile
            100                 105                 110

Leu Arg Gly Asp Phe Ser Ser Ala Asn Asn Arg Asp Asn Thr Tyr Asn
        115                 120                 125

Arg Val Ser Glu Asp Leu Arg Ser Arg Ile Glu Val Leu Lys Arg Lys
    130                 135                 140

Val Ile Glu Lys Val Gln His Ile Gln Leu Leu Gln Lys Asn Val Arg
145                 150                 155                 160

Ala Gln Leu Val Asp Met Lys Arg Leu Glu Val Asp Ile Asp Ile Lys
                165                 170                 175

Ile Arg Ser Cys Arg Gly Ser Cys Ser Arg Ala Leu Ala Arg Glu Val
            180                 185                 190

Asp Leu Lys Asp Tyr Glu Asp Gln Gln Lys Gln Leu Glu Gln Val Ile
        195                 200                 205

Ala Lys Asp Leu Leu Pro Ser Arg Asp Arg Gln His Leu Pro Leu Ile
    210                 215                 220

Lys Met Lys Pro Val Pro Asp Leu Val Pro Gly Asn Phe Lys Ser Gln
225                 230                 235                 240

Leu Gln Lys Val Pro Pro Glu Trp Lys Ala Leu Thr Asp Met Pro Gln
                245                 250                 255

Met Arg Met Glu Leu Glu Arg Pro Gly Gly Asn Glu Ile Thr Arg Gly
            260                 265                 270

Gly Ser Thr Ser Tyr Gly Thr Gly Ser Glu Thr Glu Ser Pro Arg Asn
        275                 280                 285

Pro Ser Ser Ala Gly Ser Trp Asn Ser Gly Ser Ser Gly Pro Gly Ser
    290                 295                 300

Thr Gly Asn Arg Asn Pro Gly Ser Ser Gly Thr Gly Gly Thr Ala Thr
```

```
              305                 310                 315                 320
        Trp Lys Pro Gly Ser Ser Gly Pro Gly Ser Thr Gly Ser Trp Asn Ser
                        325                 330                 335

Gly Ser Ser Gly Thr Gly Ser Thr Gly Asn Gln Asn Pro Gly Ser Pro
                        340                 345                 350

Arg Pro Gly Ser Thr Gly Thr Trp Asn Pro Gly Ser Ser Glu Arg Gly
                        355                 360                 365

Ser Ala Gly His Trp Thr Ser Glu Ser Ser Val Ser Gly Ser Thr Gly
                        370                 375                 380

Gln Trp His Ser Glu Ser Gly Ser Phe Arg Pro Asp Ser Pro Gly Ser
        385                 390                 395                 400

Gly Asn Ala Arg Pro Asn Asn Pro Asp Trp Gly Thr Phe Glu Glu Val
                        405                 410                 415

Ser Gly Asn Val Ser Pro Gly Thr Arg Arg Glu Tyr His Thr Glu Lys
                        420                 425                 430

Leu Val Thr Ser Lys Gly Asp Lys Glu Leu Arg Thr Gly Lys Glu Lys
                        435                 440                 445

Val Thr Ser Gly Ser Thr Thr Thr Arg Arg Ser Cys Ser Lys Thr
                        450                 455                 460

Val Thr Lys Thr Val Ile Gly Pro Asp Gly His Lys Glu Val Thr Lys
        465                 470                 475                 480

Glu Val Val Thr Ser Glu Asp Gly Ser Asp Cys Pro Glu Ala Met Asp
                        485                 490                 495

Leu Gly Thr Leu Ser Gly Ile Gly Thr Leu Asp Gly Phe Arg His Arg
                        500                 505                 510

His Pro Asp Glu Ala Ala Phe Phe Asp Thr Ala Ser Thr Gly Lys Thr
                        515                 520                 525

Phe Pro Gly Phe Phe Ser Pro Met Leu Gly Glu Phe Val Ser Glu Thr
                        530                 535                 540

Glu Ser Arg Gly Ser Glu Ser Gly Ile Phe Thr Asn Thr Lys Glu Ser
        545                 550                 555                 560

Ser Ser His His Pro Gly Ile Ala Glu Phe Pro Ser Arg Gly Lys Ser
                        565                 570                 575

Ser Ser Tyr Ser Lys Gln Phe Thr Ser Ser Thr Ser Tyr Asn Arg Gly
                        580                 585                 590

Asp Ser Thr Phe Glu Ser Lys Ser Tyr Lys Met Ala Asp Glu Ala Gly
                        595                 600                 605

Ser Glu Ala Asp His Glu Gly Thr His Ser Thr Lys Arg Gly His Ala
                        610                 615                 620

Lys Ser Arg Pro Val Arg Asp Cys Asp Asp Val Leu Gln Thr His Pro
        625                 630                 635                 640

Ser Gly Thr Gln Ser Gly Ile Phe Asn Ile Lys Leu Pro Gly Ser Ser
                        645                 650                 655

Lys Ile Phe Ser Val Tyr Cys Asp Gln Glu Thr Ser Leu Gly Gly Trp
                        660                 665                 670

Leu Leu Ile Gln Gln Arg Met Asp Gly Ser Leu Asn Phe Asn Arg Thr
                        675                 680                 685

Trp Gln Asp Tyr Lys Arg Gly Phe Gly Ser Leu Asn Asp Glu Gly Glu
                        690                 695                 700

Gly Glu Phe Trp Leu Gly Asn Asp Tyr Leu His Leu Thr Gln Arg
        705                 710                 715                 720

Gly Ser Val Leu Arg Val Glu Leu Glu Asp Trp Ala Gly Asn Glu Ala
                        725                 730                 735
```

```
Tyr Ala Glu Tyr His Phe Arg Val Gly Ser Glu Ala Glu Gly Tyr Ala
            740                 745                 750

Leu Gln Val Ser Ser Tyr Glu Thr Ala Gly Asp Ala Leu Ile Glu
        755                 760                 765

Gly Ser Val Glu Glu Gly Ala Glu Tyr Thr Ser His Asn Asn Met Gln
770                 775                 780

Phe Ser Thr Phe Asp Arg Asp Ala Asp Gln Trp Glu Asn Cys Ala
785                 790                 795                 800

Glu Val Tyr Gly Gly Gly Trp Trp Tyr Asn Asn Cys Gln Ala Ala Asn
                805                 810                 815

Leu Asn Gly Ile Tyr Tyr Pro Gly Gly Ser Tyr Asp Pro Arg Asn Asn
            820                 825                 830

Ser Pro Tyr Glu Ile Glu Asn Gly Val Val Trp Val Ser Phe Arg Gly
        835                 840                 845

Ala Asp Tyr Ser Leu Arg Ala Val Arg Met Lys Ile Arg Pro Leu Val
    850                 855                 860

Thr Gln
865

<210> SEQ ID NO 89
<211> LENGTH: 6
<212> TYPE: PRT
<213> ORGANISM: Artificial Sequence
<220> FEATURE:
<223> OTHER INFORMATION: synthesized

<400> SEQUENCE: 89

Gly Gly Gly Ser Gly Gly
1               5

<210> SEQ ID NO 90
<211> LENGTH: 9
<212> TYPE: PRT
<213> ORGANISM: Artificial Sequence
<220> FEATURE:
<223> OTHER INFORMATION: synthesized

<400> SEQUENCE: 90

Gly Gly Gly Ser Gly Gly Gly Gly Ser
1               5

<210> SEQ ID NO 91
<211> LENGTH: 12
<212> TYPE: PRT
<213> ORGANISM: Artificial Sequence
<220> FEATURE:
<223> OTHER INFORMATION: synthesized

<400> SEQUENCE: 91

Gly Leu Tyr Gly Leu Tyr Gly Leu Tyr Ser Glu Arg
1               5                   10

<210> SEQ ID NO 92
<211> LENGTH: 15
<212> TYPE: PRT
<213> ORGANISM: Artificial Sequence
<220> FEATURE:
<223> OTHER INFORMATION: synthesized

<400> SEQUENCE: 92

Gly Leu Tyr Gly Leu Tyr Gly Leu Tyr Gly Leu Tyr Ser Glu Arg
1               5                   10                  15
```

<210> SEQ ID NO 93
<211> LENGTH: 18
<212> TYPE: PRT
<213> ORGANISM: Artificial Sequence
<220> FEATURE:
<223> OTHER INFORMATION: synthesized

<400> SEQUENCE: 93

Gly Leu Tyr Gly Leu Tyr Gly Leu Tyr Gly Leu Tyr Gly Leu Tyr Ser
1               5                   10                  15

Glu Arg

<210> SEQ ID NO 94
<211> LENGTH: 12
<212> TYPE: PRT
<213> ORGANISM: Artificial Sequence
<220> FEATURE:
<223> OTHER INFORMATION: synthesized

<400> SEQUENCE: 94

Gly Leu Tyr Gly Leu Tyr Ser Glu Arg Ser Glu Arg
1               5                   10

<210> SEQ ID NO 95
<211> LENGTH: 12
<212> TYPE: PRT
<213> ORGANISM: Artificial Sequence
<220> FEATURE:
<223> OTHER INFORMATION: synthesized

<400> SEQUENCE: 95

Gly Leu Tyr Ser Glu Arg Ser Glu Arg Ser Glu Arg
1               5                   10

<210> SEQ ID NO 96
<211> LENGTH: 12
<212> TYPE: PRT
<213> ORGANISM: Artificial Sequence
<220> FEATURE:
<223> OTHER INFORMATION: synthesized

<400> SEQUENCE: 96

Ser Glu Arg Ser Glu Arg Ser Glu Arg Gly Leu Tyr
1               5                   10

<210> SEQ ID NO 97
<211> LENGTH: 15
<212> TYPE: PRT
<213> ORGANISM: Artificial Sequence
<220> FEATURE:
<223> OTHER INFORMATION: synthesized

<400> SEQUENCE: 97

Ser Glu Arg Ser Glu Arg Ser Glu Arg Ser Glu Arg Gly Leu Tyr
1               5                   10                  15

<210> SEQ ID NO 98
<211> LENGTH: 18
<212> TYPE: PRT
<213> ORGANISM: Artificial Sequence
<220> FEATURE:
<223> OTHER INFORMATION: synthesized

<400> SEQUENCE: 98

Ser Glu Arg Ser Glu Arg Ser Glu Arg Ser Glu Arg Ser Glu Arg Gly

```
1               5                   10                  15
Leu Tyr

<210> SEQ ID NO 99
<211> LENGTH: 12
<212> TYPE: PRT
<213> ORGANISM: Artificial Sequence
<220> FEATURE:
<223> OTHER INFORMATION: synthesized

<400> SEQUENCE: 99

Ser Glu Arg Ser Glu Arg Gly Leu Tyr Gly Leu Tyr
1               5                   10

<210> SEQ ID NO 100
<211> LENGTH: 12
<212> TYPE: PRT
<213> ORGANISM: Artificial Sequence
<220> FEATURE:
<223> OTHER INFORMATION: synthesized

<400> SEQUENCE: 100

Ser Glu Arg Gly Leu Tyr Gly Leu Tyr Gly Leu Tyr
1               5                   10

<210> SEQ ID NO 101
<211> LENGTH: 12
<212> TYPE: PRT
<213> ORGANISM: Artificial Sequence
<220> FEATURE:
<223> OTHER INFORMATION: synthesized

<400> SEQUENCE: 101

Gly Leu Tyr Ser Glu Arg Gly Leu Tyr Gly Leu Tyr
1               5                   10

<210> SEQ ID NO 102
<211> LENGTH: 21
<212> TYPE: PRT
<213> ORGANISM: Artificial Sequence
<220> FEATURE:
<223> OTHER INFORMATION: synthesized

<400> SEQUENCE: 102

Gly Leu Tyr Gly Leu Tyr Gly Leu Tyr Ser Glu Arg Gly Leu Tyr Gly
1               5                   10                  15

Leu Tyr Gly Leu Tyr
            20

<210> SEQ ID NO 103
<211> LENGTH: 24
<212> TYPE: PRT
<213> ORGANISM: Artificial Sequence
<220> FEATURE:
<223> OTHER INFORMATION: synthesized

<400> SEQUENCE: 103

Gly Leu Tyr Gly Leu Tyr Gly Leu Tyr Gly Leu Tyr Ser Glu Arg Gly
1               5                   10                  15

Leu Tyr Gly Leu Tyr Gly Leu Tyr
            20

<210> SEQ ID NO 104
<211> LENGTH: 60
<212> TYPE: PRT
```

```
<213> ORGANISM: Artificial Sequence
<220> FEATURE:
<223> OTHER INFORMATION: synthesized

<400> SEQUENCE: 104

Gly Leu Tyr Gly Leu Tyr Gly Leu Tyr Gly Leu Tyr Ser Glu Arg Gly
1               5                   10                  15

Leu Tyr Gly Leu Tyr Gly Leu Tyr Gly Leu Tyr Ser Glu Arg Gly Leu
            20                  25                  30

Tyr Gly Leu Tyr Gly Leu Tyr Gly Leu Tyr Ser Glu Arg Gly Leu Tyr
        35                  40                  45

Gly Leu Tyr Gly Leu Tyr Gly Leu Tyr Ser Glu Arg
    50                  55                  60

<210> SEQ ID NO 105
<211> LENGTH: 89
<212> TYPE: PRT
<213> ORGANISM: Artificial Sequence
<220> FEATURE:
<223> OTHER INFORMATION: synthesized

<400> SEQUENCE: 105

Gly Gly Leu Tyr Gly Leu Tyr Gly Leu Tyr Gly Leu Tyr Ser Glu Arg
1               5                   10                  15

Gly Leu Tyr Gly Leu Tyr Gly Leu Tyr Gly Leu Tyr Ser Glu Arg Ala
            20                  25                  30

Leu Ala Ser Glu Arg Ser Glu Arg Ala Leu Ala Ser Glu Arg Thr His
        35                  40                  45

Arg Gly Leu Tyr Gly Leu Tyr Pro Ser Glu Arg Gly Leu Tyr Gly Leu
    50                  55                  60

Tyr Gly Leu Tyr Gly Leu Tyr Ser Glu Arg Gly Leu Tyr Gly Leu Tyr
65                  70                  75                  80

Gly Leu Tyr Gly Leu Tyr Ser Glu Arg
            85

<210> SEQ ID NO 106
<211> LENGTH: 158
<212> TYPE: PRT
<213> ORGANISM: Artificial Sequence
<220> FEATURE:
<223> OTHER INFORMATION: synthesized

<400> SEQUENCE: 106

Gly Leu Tyr Gly Leu Tyr Gly Leu Tyr Gly Leu Tyr Ser Glu Arg Gly
1               5                   10                  15

Leu Tyr Gly Leu Tyr Gly Leu Tyr Gly Leu Tyr Ser Glu Arg Thr His
            20                  25                  30

Arg Ala Leu Ala Ser Glu Arg Ser Glu Arg Ala Leu Ala Ser Glu Arg
        35                  40                  45

Thr His Arg Gly Leu Tyr Gly Leu Tyr Pro Ser Glu Arg Gly Leu Tyr
        50                  55                  60

Gly Leu Tyr Gly Leu Tyr Gly Leu Tyr Ser Glu Arg Gly Leu Tyr Gly
65                  70                  75                  80

Leu Tyr Gly Leu Tyr Gly Leu Tyr Ser Glu Arg Ala Leu Ala Pro Ser
            85                  90                  95

Glu Arg Ser Glu Arg Gly Leu Tyr Ser Glu Arg Thr His Arg Ser Glu
            100                 105                 110

Arg Gly Leu Tyr Gly Leu Tyr Thr His Arg Ala Leu Ala Ala Leu Ala
        115                 120                 125
```

```
Gly Leu Tyr Gly Leu Tyr Gly Leu Tyr Gly Leu Tyr Ser Glu Arg Gly
        130                 135                 140

Leu Tyr Gly Leu Tyr Gly Leu Tyr Gly Leu Tyr Ser Glu Arg
145                 150                 155

<210> SEQ ID NO 107
<211> LENGTH: 176
<212> TYPE: PRT
<213> ORGANISM: Artificial Sequence
<220> FEATURE:
<223> OTHER INFORMATION: synthesized

<400> SEQUENCE: 107

Gly Leu Tyr Gly Leu Tyr Gly Leu Tyr Ser Glu Arg Gly Leu Tyr Gly
1               5                   10                  15

Leu Tyr Gly Leu Tyr Ser Glu Arg Gly Leu Tyr Gly Leu Tyr Gly Leu
            20                  25                  30

Tyr Ser Glu Arg Thr His Arg Ala Leu Ala Ser Glu Arg Ser Glu Arg
        35                  40                  45

Ala Leu Ala Ser Glu Arg Thr His Arg Leu Tyr Ser Gly Leu Tyr Pro
    50                  55                  60

Ser Glu Arg Gly Leu Tyr Gly Leu Tyr Gly Leu Tyr Ser Glu Arg Gly
65                  70                  75                  80

Leu Tyr Gly Leu Tyr Gly Leu Tyr Ser Glu Arg Gly Leu Tyr Gly Leu
            85                  90                  95

Tyr Gly Leu Tyr Ser Glu Arg Ala Leu Ala Pro Ser Glu Arg Ser Glu
            100                 105                 110

Arg Leu Tyr Ser Ser Glu Arg Thr His Arg Ser Glu Arg Gly Leu Tyr
        115                 120                 125

Gly Leu Tyr Thr His Arg Ala Leu Ala Ala Leu Ala Gly Leu Tyr Gly
        130                 135                 140

Leu Tyr Gly Leu Tyr Ser Glu Arg Gly Leu Tyr Gly Leu Tyr Gly Leu
145                 150                 155                 160

Tyr Ser Glu Arg Gly Leu Tyr Gly Leu Tyr Gly Leu Tyr Ser Glu Arg
                165                 170                 175
```